(12) United States Patent
Schlingensiepen et al.

(10) Patent No.: US 8,476,246 B2
(45) Date of Patent: Jul. 2, 2013

(54) COMBINATION OF A CHEMOTHERAPEUTIC AGENT AND AN INHIBITOR OF THE TGF-BETA SYSTEM

(75) Inventors: Karl-Hermann Schlingensiepen, Donaustauf (DE); Frank Jaschinski, Obertraubling (DE); Tanja Rothammer-Hampl, Haibach (DE); Anneliese Schneider, Feldafing (DE)

(73) Assignee: Antisense Pharma GmbH, Regensburg (DE)

( * ) Notice: Subject to any disclaimer, the term of this patent is extended or adjusted under 35 U.S.C. 154(b) by 0 days.

(21) Appl. No.: 13/059,623

(22) PCT Filed: Jul. 30, 2010

(86) PCT No.: PCT/EP2010/061152
§ 371 (c)(1),
(2), (4) Date: May 13, 2011

(87) PCT Pub. No.: WO2011/012713
PCT Pub. Date: Feb. 3, 2011

(65) Prior Publication Data
US 2012/0027873 A1 Feb. 2, 2012

(30) Foreign Application Priority Data
Jul. 30, 2009 (EP) .................... 09166893

(51) Int. Cl.
| *A01N 43/04* | (2006.01) |
| *C12N 15/63* | (2006.01) |
| *C12Q 1/68* | (2006.01) |
| *C07H 21/02* | (2006.01) |
| *C07H 21/04* | (2006.01) |

(52) U.S. Cl.
USPC ............. 514/44; 435/6; 435/91.1; 435/91.31; 435/455; 435/458; 514/1; 514/2; 536/23.1; 536/24.5

(58) Field of Classification Search
USPC ........... 435/6, 91.1, 91.31, 455, 458; 514/1.2, 514/44; 536/23.1, 24.5; 424/9.1
See application file for complete search history.

(56) References Cited

U.S. PATENT DOCUMENTS

| 6,972,171 B1 * | 12/2005 | Schlingensiepen et al. . 435/6.14 |
| 2005/0272644 A1 * | 12/2005 | Chung .............................. 514/9 |
| 2006/0015952 A1 * | 1/2006 | Filvaroff ........................ 800/10 |
| 2007/0196269 A1 | 8/2007 | Schlingensiepen et al. |
| 2011/0024929 A1 * | 2/2011 | Nakamura et al. ............. 264/4.1 |

FOREIGN PATENT DOCUMENTS
WO   WO-2005/059133   6/2005

OTHER PUBLICATIONS

International Search Report for PCT/EP2010/061152, mailed on Oct. 27, 2010, 6 pages.

\* cited by examiner

*Primary Examiner* — Jane Zara
(74) *Attorney, Agent, or Firm* — Morrison & Foerster LLP

(57) ABSTRACT

Pharmaceutical composition comprising a chemotherapeutic agent and a TGF-beta antisense oligonucleotide, wherein the antisense oligonucleotide reduces the sensitivity and $IC_{50}$, respectively, of the cytotoxicity of the chemotherapeutic agent. Preferably, the antisense oligonucleotide is a TGF-beta 1, 2, and/or 3 antisense oligonucleotide and the chemotherapeutic agent is preferably gemcitabine, 5-fluorouracil, temozolomide, dacarbacine, docetaxel, cisplatin, oxaliplatin, tamoxifen, or irinotecan.

8 Claims, 5 Drawing Sheets

Figure 1:
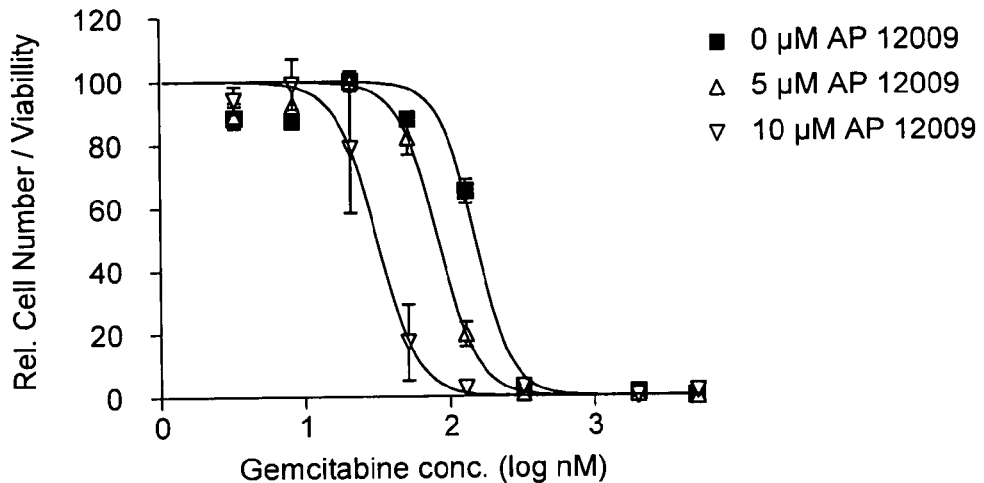

COMBINATION OF A CHEMOTHERAPEUTIC AGENT AND AN INHIBITOR OF THE TGF-BETA SYSTEM

CROSS-REFERENCE TO RELATED APPLICATIONS

This application is the national phase of PCT application PCT/EP2010/061152 having an international filing date of 30 Jul. 2010, which claims benefit of European application No. 09166893.9 filed 30 Jul. 2009. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 313632011600Seqlist.txt | Apr. 11, 2011 | 91,236 bytes |

FIELD OF THE INVENTION

This invention refers to a pharmaceutical composition comprising a chemotherapeutic agent and an antisense oligonucleotide, preferably a TGF-beta antisense oligonucleotide, or any inhibitor of the TGF-beta system, wherein the antisense oligonucleotide or the inhibitor reduces the $IC_{50}$ of the chemotherapeutic agent's cytotoxicity, and thus, increases the efficiency of the chemotherapeutic agent. The invention is further directed to the use of the pharmaceutical composition for the preparation of a medicament for treating a neoplastic disease such as cancer, preferably pancreatic cancer, bladder cancer, glioma, astrocytoma, melanoma, renal carcinoma, lung cancer, breast cancer, ovary cancer, prostate cancer, colorectal cancer, gastric cancer, endometrial cancer, and osteosarcoma as well as to methods for production of such pharmaceutical composition.

The use of a chemotherapeutic agent for the preparation of a medicament or radiation is the most common means, beside surgery, for the treatment of neoplastic diseases. Such a chemotherapeutic agent is for example an alkylating agent, an antimetabolite or an alkaloid derived from a plant. The effect of these chemotherapeutic agents and radiation is the unspecific inhibition of the cell proliferation and the unspecific induction of cell death, respectively, leading to numerous severe side effects. A chemotherapeutic agent or radiation inhibits for example proliferation of rapidly growing cells, other than tumor cells, such as hair follicle, colon mucosa cells or immune cells, e.g., T-lymphocytes, B-lymphocytes, natural killer cells, granulocytes, macrophages, microglia cells as well as the respective precursor cells of the bone marrow. In many cases the use of chemotherapeutic agents for the preparation of a medicament for treating cancer and/or the use of radiation do not lead to a sufficient result in the prolongation of the survival of a patient, in particular the median survival, which is sometimes enforced by the severe side effects of the chemotherapeutic agent and/or radiation.

Muramaki et al., 2008, describe a chemosensitization of gemcitabine-resistant human bladder cancer cells by administration of a clusterin antisense oligonucleotide. It is known that the administration of gemcitabine upregulates the clusterin expression, i.e., the expression of sCLU-2 expression levels in a time dependent manner, which tends to result in resistance of the cell against gemcitabine. The sCLU-2 antisense oligonucleotide reduced the increased sCLU-2 expression level and chemosensitized the resistant cells to gemcitabine that the concentration of gemcitabine that reduces the effect by 50% ($IC_{50}$) is decresed from 100 nM to 10 nM.

Combinations of chemotherapeutic agents and antisense oligonucleotides were further described by Alberts et al., 2004. Alberts et al. investigated the effect of gemcitabine and ISIS-2503, an H-ras phosphorothioate antisense oligonucleotide, on patients with locally advanced or metastatic pancreatic adenocarcinoma, wherein H-ras is a known oncogene.

WO 2005/059133 A2 refers to pharmaceutical compositions comprising an antineoplastic chemotherapeutic agent and a stimulator of the immune system, which led to an increased cytocytoxicity of lymphokine activated killer cells (LAK cells) on glioma cells in comparison to a stimulator of the immune system alone.

Paz-Ares et al., 2006, disclose the use of a combination of gemcitabine, cisplatin, and a protein kinase C-alpha antisense oligonucleotide for the preparation of a medicament for treating non-small-cell lung cancer. However, the use of the combination of these chemotherapeutic agents with the antisense oligonucleotide did not enhance the survival or show any other positive effect for the patient suffering from non-small-cell lung cancer. An alternative combination of gemcitabine and 5-fluorouracil for treating pancreatic carcinoma, which is described by Bellone et al., 2006, did likewise fail.

WO 02/17852 A2 describes the combination of a bcl-2 antisense oligonucleotide with a chemoagent in specific administration doses, wherein the bcl-2 antisense oligonucleotide is administered to the patient at high doses for a short period of time, i.e., 14 days. Bcl-2 is an inhibitor of apoptosis since the chemotherapeutic agents described are inducers of apoptosis. Tumor cells become resistant to the chemotherapeutic agents by upregulating bcl-2.

Hence, the objective problem underlying the present invention is improvement of efficiency of chemotherapeutic agents and pharmaceutical compositions comprising such chemotherapeutic agent, respectively, in the treatment of neoplastic diseases, in particular in non-resistant cells.

SUMMARY OF THE INVENTION

The present invention refers in one embodiment to a pharmaceutical composition comprising a chemotherapeutic agent and an inhibitor of the TGF-beta system, preferably an antisense oligonucleotide, e.g., an antitumoral antisense oligonucleotide, wherein the antisense oligonucleotide surprisingly leads to a reduction of the $IC_{50}$ of the cytotoxicity of the chemotherapeutic agent in a dose-dependent manner on the chemotherapeutic agent's cytotoxicity. A preferred antisense oligonucleotide is a TGF-beta antisense oligonucleotide like a TGF-beta 1, TGF-beta 2, or TGF-beta 3 antisense oligonucleotide, or combinations thereof, which hybridise with an area of the messenger RNA (m-RNA) and/or DNA encoding TGF-beta 1, -2 and/or -3, or hybridise with m-RNA and/or DNA encoding a TGF-beta 1, -2, and/or -3 receptor.

Furthermore, the inhibitor of the TGF-beta system is for example selected from the group consisting of TGF-beta binding proteins that are no antibodies, TGF-beta binding receptors, parts of TGF-beta binding receptors, TGF-beta specific peptides and low molecular substances binding TGF-beta or any of their proteins, receptors, part of receptor protein or low molecular substance inhibiting the function of TGF-beta.

The inhibitor of the TGF-beta system, e.g., the antisense oligonucleotide results in a reduction of the $IC_{50}$ of the chemotherapeutic agent's cytotoxicity in a resistant or a non-resistant cell, i.e., a cell, which is resistant or non-resistant to the chemotherapeutic agent.

The pharmaceutical composition of this invention is in particular for treating neoplastic diseases like cancer and for the treatment of autoimmune diseases. Preferably, the pharmaceutical composition is used for the preparation of a medicament for treating a neoplastic disease, preferably cancer. The pharmaceutical composition and/or its compounds are prepared in any dosage form and are administered in any route of administration known in the art.

The pharmaceutical composition is suitable as a first line treatment of a neoplastic disease like cancer, or as a second, third etc. line treatment before, after or in combination with therapeutic treatments such as radiation.

The chemotherapeutic agent and the inhibitor of the TGF-beta system of the pharmaceutical composition, preferably an antisense oligonucleotide are administered either separately or together in one formulation. If more than one chemotherapeutic agent and/or more than one inhibitor of the TGF-beta system, e.g., an antisense oligonucleotide is administered, the chemotherapeutic agent and/or inhibitors of the TGF-beta system such as an antisense oligonucleotide are administered separately or together in one formulation.

In preferred embodiments, the administration of the inhibitor of the TGF-beta system such as an antisense oligonucleotide, follows or preceeds the administration of the chemotherapeutic agent, or the inhibitor of the TGF-beta system and the chemotherapeutic are administered concurrently.

Due to the reduced $IC_{50}$ of the cytotoxicity of the chemotherapeutic agent, the effectivity of the chemotherapeutic agent is increased, and in a preferred embodiment the amount and dose, respectively, of the chemotherapeutic agent is reduced resulting advantageously in reduced severe negative side effects of the chemotherapeutic agent.

In a further preferred embodiment the combination of the chemotherapeutic agent and the inhibitor of the TGF-beta system, for example the antisense oligonucleotide, in the present pharmaceutical composition leads to an advantageous extension of the patient's life time based on the supraadditive and synergistic, respectively, antitumoral effect of the compounds.

Preferably, the chemotherapeutic agent does not negatively effect the interaction of the inhibitor of the TGF-beta system, e.g., an antisense oligonucleotide with its target.

The present invention further relates to methods for the production of the pharmaceutical composition.

FIGURES

FIG. 1 presents the reductive effect of a TGF-beta 2 antisense oligonucleotide, for example SEQ ID No. 30, on the $IC_{50}$ regarding gemcitabine's cytotoxicity in a dose dependent manner after data normalization. Gemcitabine was added to Hup-T3 cells, a pancreatic carcinoma cell line in concentrations of 5 µM, 2 µM, 800 nM, 320 nM, 128 nM, 51.2 nM, 20.5 nM, 8.2 nM, or 3.3 nM in combination with the TGF-beta 2 antisense oligonucleotide in concentrations of 0 µM (■), 5 µM (Δ), or 10 µM (∇). 10 µM of the TGF-beta 2 antisense oligonucleotide reduce the $IC_{50}$ of gemcitabine about 4 to 5× in comparison to 0 µM TGF-beta 2 antisense oligonucleotide.

Figure 2:
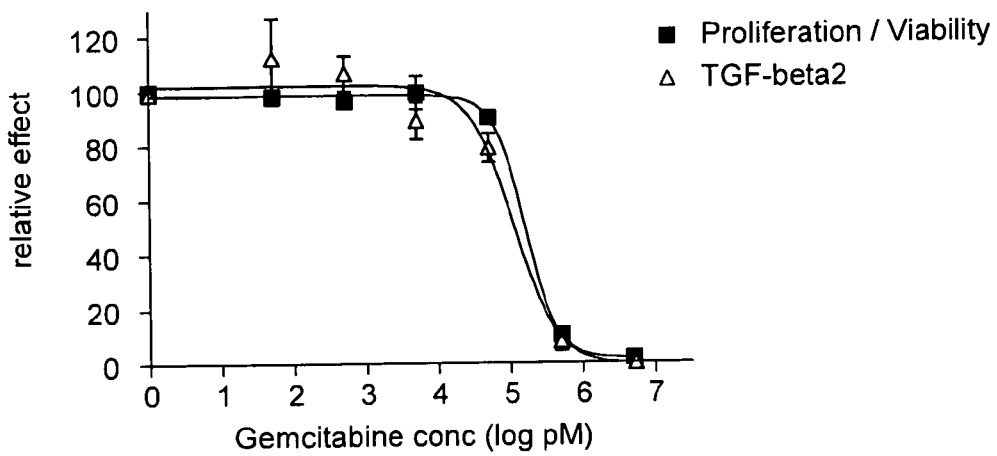

FIG. 2 shows the effect of gemcitabine on proliferation and viability, respectively, of Hup-T3 cells and the secretion of TGF-beta 2 after data normalization. Gemcitabine at 5 µM, 500 nM, 50 nM, 5 nM, 0.5 nM, or 0.05 nM has no specific influence, in particular no specific inhibitory and/or stimulatory effect, on TGF-beta 2 secretion. The decrease of TGF-beta 2 secretion (■) correlates to the proliferation and viability, respectively, of the cells, which decreases at higher gemcitabine concentrations (▲) due to the cytotoxic effect of gemcitabine.

Figure 3:
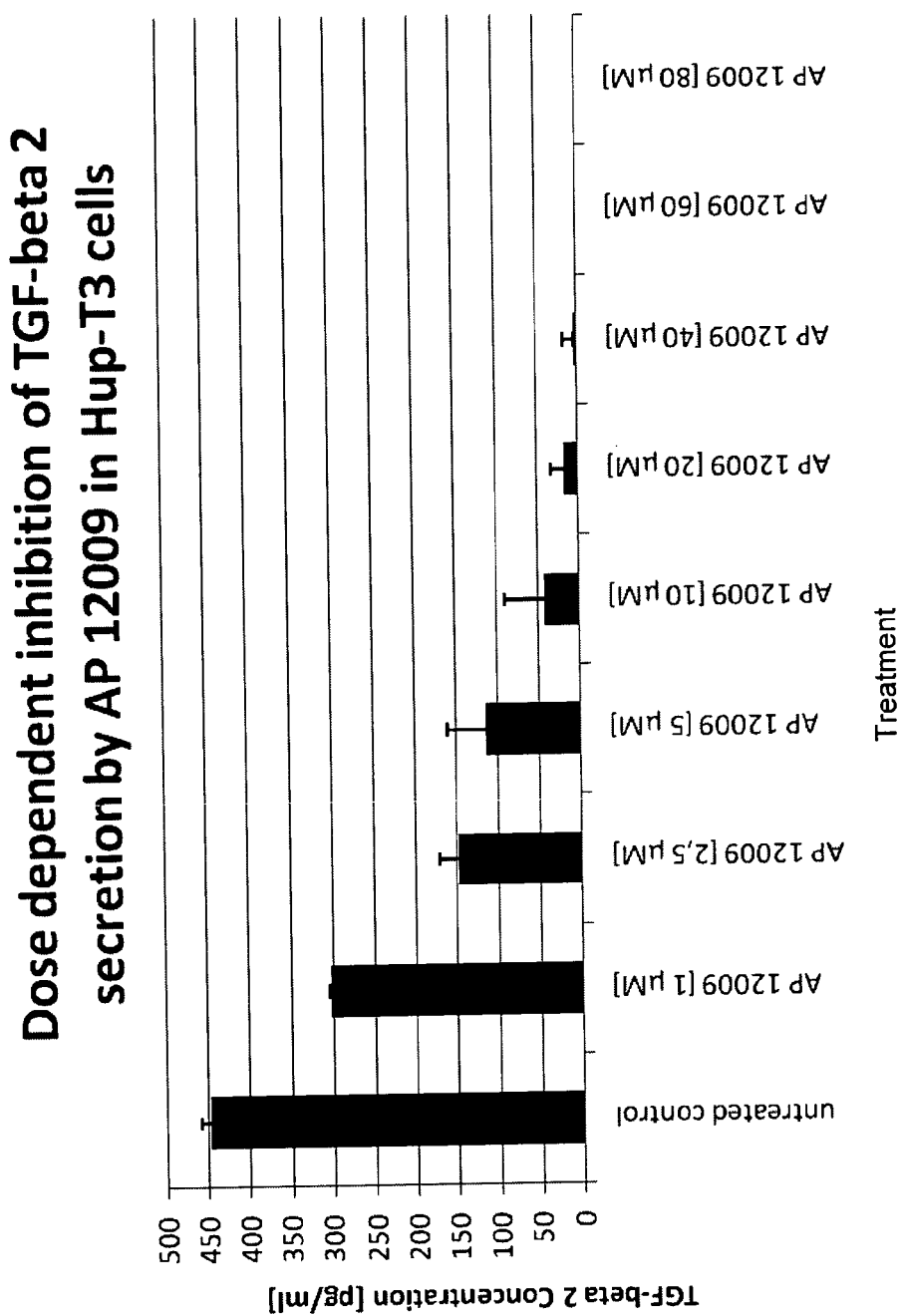

FIG. 3 presents the dose dependent inhibitory effect of TGF-beta 2 antisense oligonucleotide on TGF-beta 2 secretion. TGF-beta 2 antisense oligonucleotide, for example SEQ ID No. 30, was administered to Hup-T3 cells in concentrations of 0 µM (control), 1 µM, 2.5 µM, 5 µM, 10 µM, 20 µM, 40 µM, 60 µM, or 80 µM. No gemcitabine was added to the cells.

Figure 4:
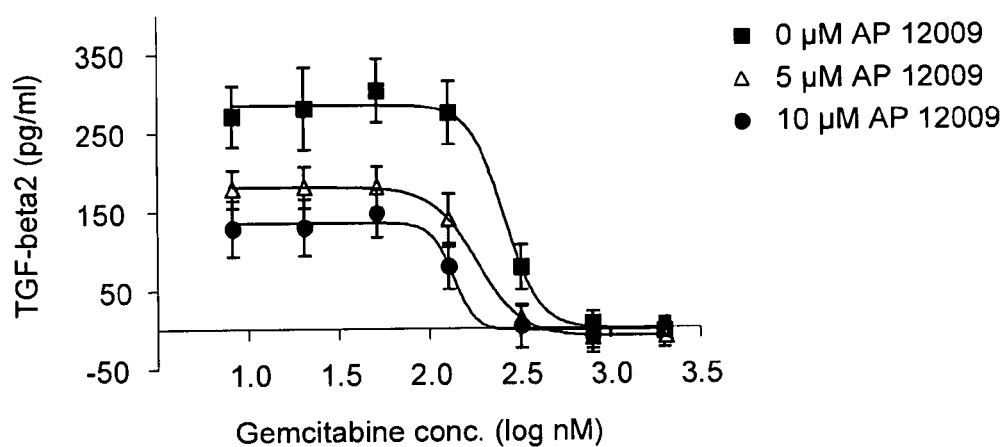

FIG. 4 demonstrates that gemcitabine does not affect the interaction of the TGF-beta 2 antisense oligonucleotide with its target, and thus, does not affect the inhibitory effect of the antisense oligonucleotide on its target. The antisense oligonucleotide inhibited TGF-beta 2 secretion in a dose dependent manner (0 µM (■), 5 µM (Δ), or 10 µM (•) TGF-beta 2 antisense oligonucleotide) in the presence of gemcitabine (2 µM, 800 nM, 320 nM, 128 nM, 51.2 nM, 20.5 nM, 8.2 nM). At higher gemcitabine concentrations the proliferation and viability, respectively, of Hup-T3 cells decreased and gemcitabine indirectly influenced TGF-beta 2 secretion via reduction of proliferation and viability, respectively, of the cells, which decreases at higher gemcitabine concentrations due to the cytotoxic effect of gemcitabine.

Figure 5:
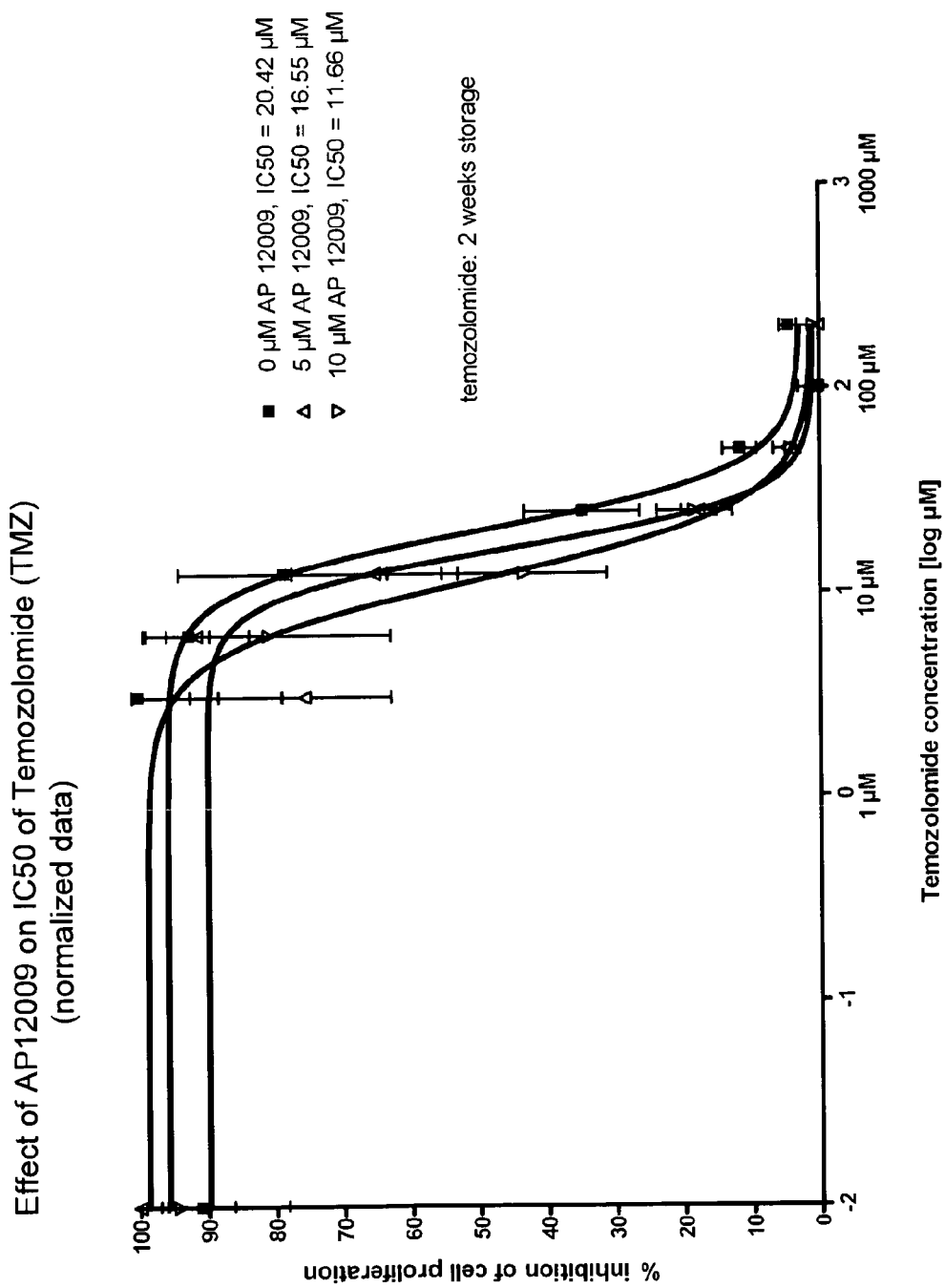

FIG. 5 shows the reductive effect of a TGF-beta 2 antisense oligonucleotide, for example SEQ ID No. 30, on the $IC_{50}$ regarding temozolomide's cytotoxicity in a dose dependent manner after data normalization. Temozolomide was added to MEL-Juso cells, a melanoma cell line, in concentrations of 200 µM, 100 µM, 50 µM, 25 µM, 12.5 µM, 6.25 µM, 3.125 µM, or 0 µM in combination with the TGF-beta 2 antisense oligonucleotide in concentrations of 0 µM (■), 5 µM (▲), or 10 µM (▼). 10 µM of the TGF-beta 2 antisense oligonucleotide reduced the $IC_{50}$ of temozolomide about 2× in comparison to 0 µM TGF-beta 2 antisense oligonucleotide.

Figure 6:
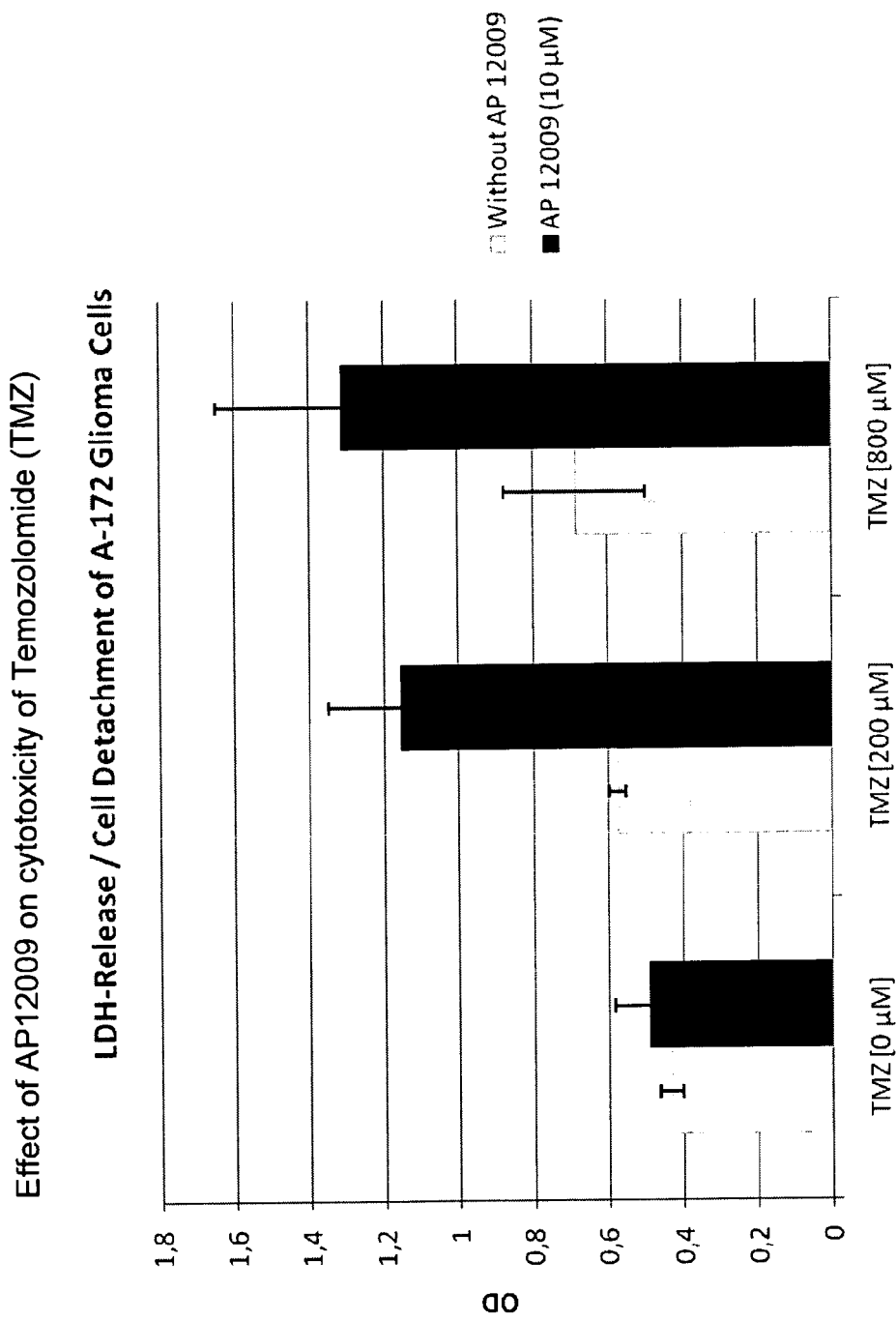

FIG. 6 demonstrates the effect of a TGF-beta 2 antisense oligonucleotide on the cytotoxicity of temozolomide. Temozolomide was administered to A-172 cells, a glioma cell line, in concentrations of 200 µM and 800 µM, respectively, either alone or in combination with 10 µM of a TGF-beta 2 antisense oligonucleotide, for example SEQ ID No. 30. The combination of temozolomide with the TGF-beta 2 antisense oligonucleotide increased the cytotoxic effect of temozolomide significantly, about 2 to 3× in comparison to temozolomide alone.

DETAILED DESCRIPTION OF THE INVENTION

In the present invention, an inhibitor of the TGF-beta system such as an antisense oligonucleotide, in particular a TGF-beta 1 antisense oligonucleotide, TGF-beta 2 antisense oligonucleotide, and/or TGF-beta 3 antisense oligonucleotide, increases the efficiency of a chemotherapeutic agent in a cell, a tissue, and/or an organ of a subject. In a preferred embodiment, such antisense oligonucleotide is part of a pharmaceutical composition together with a chemotherapeutic agent, wherein the chemotherpeutic is for example gemcitabine, 5-fluorouracil, temozolomide, dacarbacine, docetaxel, cisplatin, oxaliplatin, tamoxifen, or irinotecan.

The pharmaceutical composition of the present invention is applicable for treating a neoplastic disease in any mammal. Examples of mammal include laboratory animals, including rodents such as mice, rats and guinea pigs; farm animals such as cows, sheep, pigs and oats; pet animals such as dogs and cats; and primates such as monkeys, apes and humans. The pharmaceutical composition is most preferably applied in human clinical situations, particularly for treating neoplastic diseases.

In one embodiment of this invention one or more chemotherapeutic agents and one or more antisense oligonucleotides and/or one or more inhibitors of the TGF-beta system inhibiting the cell proliferation, form a mixture comprising at least two of these components, wherein the components are either in a pure form or together with a pharmaceutically acceptable carrier, filler, lubricant, diluent, excipient, disintegrate, and/or adjuvant.

In another embodiment of this invention, the one or more chemotherapeutic agents and the one or more inhibitors such as an antisense oligonucleotide, are separate in one pharmaceutical composition. The pharmaceutical composition comprises each of these components in a pure form or together with a pharmaceutically acceptable carrier, filler, lubricant, diluent, excipient, disintegrate, and/or adjuvant, wherein the pharmaceutically acceptable carrier, lubricant, diluent, excipient, disintegrate and/or adjuvant.

The antisense oligonucleotide is preferably any TGF-beta antisense oligonucleotide, which reduces the $IC_{50}$ of the cytotoxicity of the chemotherapeutic agent, and thus, increases the sensitivity of the cell, tissue, and/or organ to the chemotherapeutic agent in vitro, ex vivo, or in vivo. Such antisense oligonucleotides are for example directed against prostaglandine E2 (PGE, e.g., SEQ ID NO. 79-89), VEGF (e.g., SEQ ID NO. 90-126), or IL-10 (e.g., 127-146), and preferably against TGF-beta 1 (e.g., SEQ ID NO. 1-21), TGF-beta 2 (e.g., SEQ ID NO. 22-48), TGF-beta 3 (e.g., SEQ ID NO. 49-78).

The antitumoral antisense oligonucleotide is an oligonucleotide affecting a tumor, wherein the antitumoral antisense oligonucleotide affects a tumor directly or indirectly. In a direct way, the antisense oligonucleotide blocks the transcription and expression, respectively, of a protein or peptide, which is for example a biological factor in the tumor, e.g., the production of TGF-beta, in particular of TGF beta 2. In an indirect way, the antisense oligonucleotide affects the transcription and/or expression of a protein or peptide, for example a factor inducing the function of an immune cell and/or the immune system and in consequence reducing or inhibiting the tumor cell growth and/or inducing cell death of a cancer cell.

In an alternative embodiment, the inhibitor of the TGF-beta system such as an antisense oligonucleotide, in particluar the antitumoral antisense oligonucleotide, influences the signal transduction, i.e., leads to an increase or decrease of the signal transduction, of factors involved in tumor formation and/or persistance such as capillary formation in the tumor.

Immune cells are for example lymphoid cells, such as T cells, B cells, NK cells (natural killer cells), NK T cells (natural killer T cells), granulocytes, such as neutrophils, eosinophils, basophils, and mononuclear cells such as monocytes, macrophages, dendritic cells and mast cells.

In the context of this invention a TGF-beta inhibitor is any substance, e.g., a protein, peptide, small molecule, inhibiting the function of TGF-beta in that any effect that is induced by TGF-beta is inhibited.

In a preferred embodiment a TGF-beta inhibitor is a substance inhibiting the production of TGF-beta, a substance binding TGF-beta and/or a substance inhibiting the function of TGF-beta downstream its activation cascade. For more details about TGF-beta antagonists see also Wojtowicz-Praga (2003).

In particular, an inhibitor of the TGF-beta system is any substance able to inhibit the expression or function of TGF-beta, in particular TGF-beta 1, -2, and/or -3. The inhibitor is for example selected from the group consisting of TGF-beta binding proteins that are no antibodies, TGF-beta antibodies, TGF-beta binding receptors, parts of TGF-beta binding receptors, TGF-beta specific peptides and low molecular substances binding TGF-beta or any of their proteins, receptors, part of receptor protein or low molecular substance inhibiting the expression and/or the function of TGF-beta. Preferably, an inhibitor of the TGF-beta system has a molecular weight of less than about 10 kDa and more than about 1 Da of organic or inorganic origin inhibiting the TGF-beta system.

In yet another embodiment the substance inhibiting the production of TGF-beta is a peptide, a peptide of less than 100 kDa, peptides being part of TGF-beta, a protein, a protein that is not an antibody, and/or a small molecule, e.g. tranilast (N-[3,4-dimethoxycinnamoyl]-anthranilic acid) (Wilkenson, K. A. 2000).

In one embodiment the peptides being part of TGF-beta are sequences of those given in example 9. Example 9 presents the amino acid sequences of TGF-beta 1, TGF-beta 2 and TGF-beta 3 also published in Mittl (1996).

In one preferred embodiment peptides comprise the 112 amino acids counted from the end of the TGF-beta 1, TGF-beta 2 or TGF-beta 3 peptide as described in example 9. The start of those peptides is after the RXXR motif, ending 113 amino acids before the end of the TGF-beta 1, TGF-beta 2 or TGF-beta 3 peptide, in which R is the amino acid Arginin and XX represents any amino acid or is even no amino acid.

In one embodiment peptides being part of TGF-beta are parts of the sequences presented in example 9 comprising one to all amino acids of this peptide, in other embodiments preferred peptides comprise about 1-100 amino acids, about 2-50 amino acids, about 3-30 amino acids or about 5-20 amino acids of those peptides.

In yet other embodiments preferred amino acids are those presented in example 7 for TGF-beta 1, TGF-beta 2 and TGF-beta 3 with the respective numbers 1-78.

Further preferred embodiments are parts of amino acids which are described above comprising or consisting of about 1-50 amino acids, about 1-40, about 2-30, about 3-25, about 4-18, about 5-15 or about 6-12 amino acids.

In yet other embodiments of the peptides described above at least one of the basic amino acid selected from the group of Histidin (H), Lysin (K) and/or Arginin (R) is substituted by another basic amino acid selected from this group without loosing its TGF-beta antagonizing effects.

In yet other embodiments of the peptides described above at least one of the acid amino acid selected from the group of glutaminic acid (E) and/or asparaginic acid (D) is substituted by its counterpart of this group without loosing its TGF-beta antagonizing effects.

The peptides that are part of TGF-beta wherein some amino acids are replaced conservatively compared to their sequences presented in example 9 are also referred to as analogs of TGF-beta 1, TGf-beta 2 and/or TGF-beta 3.

In some embodiments in the analogs of TGF beta 1, TGF-beta 2 and TGF-beta 3 about 1% to about 30%, about 2% to about 20%, about 3% to about 15%, 4% to about 12% or about 5% to about 10% of the amino acids are replaced conservatively.

Amino acid replaced conservatively, also referred to as conservative analogs or active derivatives of peptides in the context of this invention means replacing at least one amino acid of a peptide or protein. Preferably at least one acid amino acid (glutaminic acid (E), asparaginic acid (D)) is replaced by the respective other acid amino acid, accordingly at least one basic amino acid is replaced by another basic amino acid, at least one amino acid with a polar group (—OH, —SH, —$CONH_2$) is replaced by another amino acid with a polar group and/or amino acids with pure carbon side chains are replaced by another amino acid with pure carbone side chain. Peptides and/or proteins conservatively replaced with amino acids are still in the scope of this invention.

In another embodiment the peptides described above are single and not in the combination with a chemotherapeutic agent. In yet another embodiment these peptides are used for preparing a pharmaceutical composition with a pharmaceutically acceptable carrier. In yet another embodiment these peptides are comprised by a pharmaceutical composition for the treatment of neoplastic diseases and in yet another embodiment these peptides are used for a method treating neoplastic diseases or used for the preparation of a medicament for treating a neoplastic disease according to this invention. The neoplastic disease is in particular a cancer or a tumor such as pancreatic cancer, bladder cancer, brain tumor, melanoma, renal carcinoma, lung cancer, breast cancer, ovary cancer, prostate cancer, colorectal cancer, gastric cancer, endometrial cancer, osteosarcoma, Myosarcoma, blood born tumors, leukemias, tumor metastasis, hemangiomas, acoustic neuromas, neurofibromas, trachomas, pyogenic, granulomas, psoriasis, astracytoma, acoustic neuroma, blastoma, Ewing's tumor, craniopharyngloma, ependymoma, medulloblastoma, glioma, hemangloblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, cystadenocarcinome, embrional carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostata cancer, small intestine carcinoma, prostate carcinoma, rectal cancer, renal cell carcinoma, skin cancer, small-cell bronchogenic/lung carcinoma, squamous cell carcinoma, sebaceous gland carcinoma, testicular carcinoma, and uterine cancer. The brain tumor is in particular an oligodendroglioma, an anaplastic oligoastrozytoma, a glioblastoma, a brain metastasis, a myeloma, a plasmocytoma, a glioma, or an astrocytoma.

In yet another embodiment TGF-beta inhibitors are receptors and/or parts of it, or an antibody and/or parts of it binding TGF-beta, or a protein and/or peptide binding to TGF-beta and in that way inhibiting the function of TGF-beta. The antibodies are for example commercially available, see e.g. R & D Systems, Inc. The production of those antibodies is well known in the art. Animals such as e.g. chicken, mice, rabbits, goats, are immunized with purified human TGF-beta, and the animals produce an antibody against TGF-beta. The antibodies (e.g., IgY) are purified with e.g. affinity chromatography as described for example by Cooper, H. M. (1995) and are optionally further modified e.g., biotinylated. In a more preferred embodiment the TGF-beta antibodies are humanized antibodies as described for example by Carrington (1998). Preferred embodiments of the peptides are e.g. Latency-associated peptides, which inhibit one or more or all three isoforms of TGF-beta (TGF-beta 1, TGF-beta 2 and TGF-beta 3).

In another embodiment the TGF-beta inhibitor is a protein, peptide or a small molecule inhibiting the function of the TGF-beta receptor, acting extracellularly or intracellularly. Peptides and proteins are for example produced according to classical methods of peptide and protein synthesis such as Merrifield synthesis or Fmoc synthesis.

In an alternative embodiment, an antisense oligonucleotide, preferably an antitumoral antisense oligonucleotide hybridizes with its target messenger RNA (mRNA) and/or DNA. The target mRNA and/or DNA is any mRNA and/or DNA that is directly or indirectly involved in the formation of a neoplastic disease such as cancer. In a preferred embodiment, the antisense oligonucleotide is a TGF-beta antisense oligonucleotide, for example a TGF-beta 1, TGF-beta 2, and/or TGF-beta 3, or its derivative, which hybridises with an area of the mRNA of TGF-beta and/or the DNA encoding TGF-beta, and thus, inhibit the production of TGF-beta.

The terms "nucleic acid" and "oligonucleotide" refer to multiple nucleotides (i.e. molecules comprising a sugar, e.g. ribose or deoxyribose) linked to a phosphate group and to a variable organic base, which is either a substituted pyrimidine, e.g. cytosine (C), thymine (T) or uracil (U) or a substituted purine, e.g. adenine (A) or guanine (G) or a modification thereof. As used herein, the terms refer to oligoribonucleotides as well as oligodeoxyribonucleotides. The terms shall also include oligonucleosides (i.e., a oligonucleotide without the phosphate) and any other organic base-containing polymer. The nucleic acids are double-stranded or single-stranded. Double-stranded molecules are more stable in vivo, while single-stranded molecules have increased activity. In one embodiment the nucleotides have lengths between about 6 and about 100 nucleotides in yet another embodiment the nucleotides have lengths of about 8 to about 40 nucleotides respectively from about 12 to about 32 nucleotides.

As used herein with respect to linked units of a nucleic acid, "linked" or "linkage" means two entities are bound to one another by any physicochemical means. Any linkage known to those of ordinary skill in the art, covalent or noncovalent, is embraced. Natural linkages, which are those ordinarily found in nature connecting the individual units of a nucleic acid, are most common. The individual units of a nucleic acid are linked, however, by synthetic or modified linkages.

In one embodiment the respective ends of this linear polymeric structure are further joined to form a circular structure. However, open linear structures are generally preferred. Within the oligonucleotides structure, the phosphate groups are commonly referred to as forming the internucleoside backbone of the oligonucleotide. The normal linkage or backbone of RNA and DNA is a 3' to 5' phosphodiester linkage.

Antisense oligonucleotides or antitumoral antisense oligonucleotides include oligonucleotides having non-naturally occurring portions with similar function. Such modified or substituted oligonucleotides are often preferred over native forms because of desirable properties such as, for example, enhanced cellular uptake, enhanced affinity for nucleic acid target (e.g. protein), altered intracellular localization and increased stability in the presence of nucleases. Modifications of the oligonucleotides as used herein comprise any chemical modifications of the sugar, the base moiety and/or the internucleoside linkage.

In one embodiment oligonucleotides or antitumoral antisense oligonucleotides with a covalently modified base and/or sugar include for example oligonucleotides having backbone sugars which are covalently attached to low molecular weight organic groups other than a hydroxyl group at the 3' and/or 2' position and other than a phosphate group at the 5' position. Thus, modified oligonucleotides include for example a 2'-O-alkylated ribose group. In yet another embodiment modified oligonucleotides include sugars such as arabinose instead of ribose. Thus, the antisense oligonucleotide, in particular the antitumoral antisense oligonucleotide, is heterogeneous in the backbone composition comprising or containing any possible combination of polymer units linked together such as peptide-nucleic acids (which have amino acid backbone with nucleic acid bases). In some embodiments the oligonucleotides are homogeneous in the backbone composition.

The substituted purines and pyrimidines of the oligonucleotides include standard purines and pyrimidines such as cytosine as well as base analogs such as substituted bases (Wagner et al. 1996). Purines and pyrimidines include, but are not limited to adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties.

The single nucleotides in each oligonucleotide or polynucleotide polymer contain the same modifications, contain combinations of these modifications, or combine these modifications with phosphodiester linkages. Methods of rendering oligonucleotide or polynucleotide polymers nuclease resistant include, but are not limited to, covalently modifying the purine or pyrimidine bases. For example, bases are methylated, hydroxymethylated, or otherwise substituted (e.g., glycosylated) such that the oligonucleotides or polynucleotides are rendered substantially acid and nuclease resistant.

In a preferred embodiment, at least one end-block on the oligonucleotide is a biotin, biotin analog, avidin, or avidin analog. These molecules have the ability to block the degradation of the protected oligonucleotide or polynucleotide and provide means for high affinity attachment of the modified oligonucleotides to the solid support. Avidin and biotin derivatives which are for example used to prepare the reagents of this invention include streptavidin, succinylated avidin, monomeric avidin, biocytin (biotin-epsilon-N-lysine), biocytin hydrazide, amine or sulfhydryl derivatives of 2-iminobiotin and biotinyl-epsilon-aminocaproic acid hydrazide. Additional biotin derivatives, such as biotin-N-hydroxysuccinimide ester, biotinyl-epsilon-aminocaproic acid-N-hydroxysuccinimide ester, sulfosuccinimidyl 6-(biotin amido)hexanoate, N-hydroxysuccinimideiminobiotin, biotinbromoacetylhydrazide, p-diazobenzoyl biocytin and 3-(N-maleimidopropionyl)biocytin, can also be used as end-blocking groups on the polynucleotides of the present invention.

In another embodiment the ring structure of the ribose group of the nucleotides in the modified oligonucleotide has an oxygen in the ring structure substituted with N—H, N—R (with R being an alkyl or aryl substituent), S and/or methylene.

In yet another embodiment the base units are maintained for hybridization with an appropriate nucleic acid target compound. One such oligomeric compound, an oligonucleotide mimetic that has been shown to have excellent hybridization properties, is for example a peptide nucleic acid (PNA). In PNA compounds, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (1991).

Further modified oligonucleotide backbones include, for example, phosphorothioates, chiral phosphorothioates, phosphorodithioates, phosphorotriesters, aminoalkylphosphorotriesters, methyl- and other alky-phosphonates including 3'-alkylene phophonates and chiral phosphonates, phosphinates, phosphoramidates, including 3'-aminophosphoramidate and aminoalkylphosphoramidates, thionophosphoramidates, thionoalkylphosphonates, thionoalkylphosphotriesters, and boranophosphates having norm 3'-5' linkages, 2'-5 linked analogs of these, and those having inverted polarity wherein the adjacent pairs of nucleoside units are linked 3'-5' to 5'-3' or 2'-5' to 5'-2'. Various salts, mixed salts, and free acid forms are also included.

In a further embodiment at least one nucleotide of an oligonucleotide is modified as described in one of the modifications above. The modifications cover either the oligonucleotide continuously or irregularly.

In yet another embodiment at least two modifications as described above are combined within one oligonucleotide.

In another embodiment the 1 to about 12 or 1 to about 8 or 1 to about 4 or 1 to about 2 oligonucleotides and/or nucleotide linkages at the 3' and/or 5' end of the oligonucleotide are modified as described above.

In one embodiment the antisense oligonucleotides of this invention are hybridizing with a target, e.g. TGF-beta or its subtypes TGF-beta 1, TGF-beta 2, TGF-beta 3, or VEGF, IL-10, or PGE.

Antisense oligonucleotides of the sequence listing that comprise additional nucleotides for example about 1 to about 1000 nucleotides, from about 1 to about 500, from about 1 to about 100, from about 1 to about 50, from about 1 to about 20, from about 1 to about 10, from about 1 to about 5 or from about 1 to about 2 nucleotides bound to at least one of the 3' and/or 5' end, in a preferred embodiment on at least one of the 2' and/or 5' end, are still within the scope of this invention.

The antisense oligonucleotides are synthesized de novo using any of a number of procedures well known in the art resulting in "synthetic antisense oligonucleotides". Such procedures are for example, the b-cyanoethyl phosphoramidite method (Beaucage et al. 1981), or the nucleoside H-phosphonate method (Garegg et al. 1986, Froehler et al. 1986, Garegg et al. 1986, Gaffney et al. 1988). These antisense oligonucleotides are performed by a variety of automated oligonucleotide synthesizers available on the market.

Alternatively, antisense oligonucleotides are produced in a large scale in plasmids, (see, e.g., Sambrook, et al. 1989) and separated into smaller pieces or administered as a whole. Antisense oligonucleotides are prepared from existing nucleic acid sequences (e.g., genomic or cDNA) using known techniques, such as those employing restriction enzymes, exonucleases or endonucleases. Antisense oligonucleotides prepared in this manner are referred to as isolated nucleic acids. Antisense oligonucleotides and antitumoral antisense oligonucleotide, respectively, encompass both synthetic and isolated antisense oligonucleotides.

Antisense oligonucleotides having a modified backbone, e.g., phosphorothioate bonds, are synthesized using automated techniques employing, for example, phosphoramidate or H-phosphonate chemistries. Aryl- and alkyl-phosphonates are made, e.g., as described in U.S. Pat. No. 4,469,863. Alkyiphosphotriesters, in which the charged oxygen moiety is alkylated as described in U.S. Pat. No. 5,023,243 and European Patent No. 092,574, are prepared by automated solid phase synthesis using commercially available reagents. Methods for producing further backbone modifications of the antisense oligonucleotide and substitutions have been described (Uhlmann et al. 1990, Goodchild 1990).

Alternatively, phosphorothioates are synthesized using automated techniques employing either phosphoramidate or H-phosphonate chemistries. Aryl- and alkyl-phosphonates are made, e.g., as described in U.S. Pat. No. 4,469,863; and alkylphosphotriesters (in which the charged oxygen moiety is alkylated as described in U.S. Pat. No. 5,023,243 and European Patent No. 092,574) are prepared by automated solid phase synthesis using commercially available reagents. Methods for making other DNA backbone modifications and substitutions have been described (Uhlmann, E. et al. 1990, Goodchild, J. 1990).

The term "neoplastic disease" according to the present invention refers to a proliferative disorder caused or characterized by the proliferation of cells, which have lost susceptibility to normal growth control. The term "cancer" according to the present invention includes benigne and maligne tumors and any other proliferative disorders for example the formation of metastases. Cancers of the same tissue type in general originate from the same tissue, and are for example divided into different subtypes based on their biological characteristics. Four general categories of cancers are carcinoma, sarcoma, leukemia, and lymphoma. Over 200 different types of cancers are known, and every organ or tissue of the body can be affected. Specific examples of cancers that do not limit the definition of cancer includes solid tumors, blood born tumors such as leukemias, acute or chronic myelotic or lymphoblastic leukemia; tumor metastasis; benign tumors, for example hemangiomas, acoustic neuromas, neurofibromas, trachomas, and pyogenic granulomas; pre-malignant tumors; astrocytoma, comprising pilocyt. astrocytoma WHO I, astrocytoma WHO II, astrocytoma WHO III, blastoma, breast cancer, chordoma, craniopharyngioma, endometrial cancer, ependymoma, Ewing's tumor, gastric cancer, germinoma, glioma, glioblastoma, hemangioblastoma, hemangiopericatioma, Hodgkins lymphoma, medulloblastoma, leukaemia, mesothelioma, neuroblastoma, non-Hodgkins lymphoma, pinealoma, retinoblastoma, sarcoma (including angiosarcoma, chondrosarcoma, endothelial sarcoma, fibrosarcoma, leiomyosarcoma, liposarcoma, lymphangioandotheliosarcoma, lyphangiosarcoma, medulloblastoma, melanoma, meningioma, myosarcoma, neurinoma, oligodendroglioma, osteogenic sarcoma, osteosarcoma), seminoma, subependymoma, Wilm's tumor, or is selected from the group of bile duct carcinoma, bladder carcinoma, brain tumor, breast carcinoma, bronchogenic carcinoma, carcinoma of the kidney, cervical carcinoma, choriocarcinoma, cystadenocarcinome, embryonal carcinoma, epithelial carcinoma, esophageal carcinoma, cervical carcinoma, colon carcinoma, colorectal carcinoma, endometrial carcinoma, gallbladder carcinoma, gastric carcinoma, head and neck carcinoma, liver carcinoma, lung carcinoma, medullary carcinoma, non-small cell bronchogenic/lung carcinoma, lung cancer, ovarian carcinoma, pancreas carcinoma, papillary carcinoma, papillary adenocarcinoma, prostate carcinoma, small intestine carcinoma, rectal carcinoma, renal cell carcinoma, skin carcinoma, small-cell bronchogenic/lung carcinoma, squamous cell carcinoma, sebaceous gland carcinoma, testicular carcinoma, osteosarcoma, ovary cancer, or uterine carcinoma.

In a preferred embodiment the formation of metastasis refers to the formation of liver, lung, brain, lymphoma node and/or visceral metastasis. Each of these metastasis is treatable by use of the pharmaceutical composition of the present-invention.

A chemotherapeutic agent according to the present invention is a substance inhibiting cell proliferation and/or inducing cell death and in a preferred embodiment further inhibits the formation of metastases. The term chemotherapeutic agent comprises, but is not limited to a chemotherapeutic agent, chemotherapeutic agent supplementary potentiating agents and radioactive agents. Examples for this group are given herein.

In one embodiment a chemotherapeutic agent is selected from the group of gemcitabine, telozolomid, nitrosoureas, Vinca alkaloids, antagonists of purine and pyrimidines bases, cytostatic antibiotics, camphotecine derivatives, anti-estrogenes, anti-androgens and analogs of gonadotropin releasing hormon.

In a preferred embodiment the group of nitrosoureas comprises ACNU, BCNU, CCNU, and/or HCNU. In another embodiment the antineoplastic chemotherapeutic agent agent is selected from the group of nitrosoureas, e.g. ACNU, BCNU, HCNU and/or CCNU, cytotoxic active antibiotics, e.g. doxorubicin, pegylated liposomal doxorubicin (Caelyx®), 5-fluorodeoxyuridine, 5-fluorouracil, 5-fluorouridine, gemcitabine, procarbazine, taxol, taxotere, temozolomide, vinblastine, vincristine. Synonyms for ACNU are 3-[(-4-Amino-2-methyl-5-pyrimidinyl)methyl]-1-(2-chloroethyl)-1-nitrosourea hydrochloride, CS-439 HCl, Nidran hydrochloride, Nimustine Hydrochloride, NSC-245382. BCNU is Bischloroethylnitrosourea, the chemical name is N,N'-bis(2-chlorethyl)-N-nitroso-urea, other names are BiCNU, carmustine. CCNU is 1-(2-Chloroethy)-3-cyclohexyl-1-nitrosourea. Synonyms are N-(2-chloroethyl)-N'-cyclohexyl-N-nitroso-urea, Belustine, Cee NU, Chloroethylcyclohexylnitrosourea, ICIG 1109, Lomustine, NSC 79037. One chemical name for temozolomide is 3,4-dihydro-3-methyl-4-oxoimidazo->5,1d'1,2,3,4-tetrazin-8-carboximide. Other names for temozolomide are Temodal, Temodar, methazolastone, CCRG81045, SCH52365, NSC362856, M&B39836.

Synonyms for teniposide are 4'-Demethylepipodophyllotoxin, 9-(4,6-O-2-thenylidene-b-D-glucopyranoside), Epipodophyllotoxin, EPT, Teniposide VM-26, VM 26, 5,8,8a,9-Tetrahydro-5-(4-hydroxy-3,5-dimethoxyphenyl)-9-{[4,6-O-(2-thienylmethylene)-b-D-glucopyranosyl]oxy}furo[3',4':6,7]naphtho[2,3-d]-1,3-dioxol-6(5aH)-one.

In one embodiment the Vinca alkaloids comprise vincristine, vinblastine, vindesine and their active derivatives.

In one embodiment the antagonist of the purine and pyrimidine bases is selected from the group of 5-fluorouracile, 5-fluorodeoxiuridine, cytarabine and gemcitabine.

In other embodiments the chemotherapeutic agent is selected from the group of doxorubicine and liposomal PEGylated doxorubicin, the camphthotecine derivative is selected from the group of irinotecane and topotecane, the anti estrogenes are selected from the group of tamoxifen, exemestane, anastrozole and fulvestrant, the antiandrogens are selected from the group of flutamide and bicalutamide, the antprogesterons are selected from the group of mifepriston, the analogs of gonadotropin releasing hormon are selected from the group of leuprolide and gosereline.

In other embodiments the at least one antisense oligonucleotide, preferably an antisense oligonucleotide selected from the group consisting of TGF-beta 1, TGF-beta 2, and TGF-beta 3, and/or inhibitor if the TGF-beta inhibitor is combined with at least one chemotherapeutic selected from the following group: Acivicin; Aclarubicin; Acodazole Hydrochloride; Acronine; Adozelesin; Adriamycin; Aldesleukin; Altretamine; Ambomycin; Ametantrone Acetate; Aminoglutethimide; Amsacrine; Anastrozole; Anthramycin; Asparaginase; Asperlin; Avastin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Cetuximab; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl] acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Erlotinib; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; 5-Fluorouracil; 5-FdUMP; Flurocitabine; Fosquidone; Fostriecin Sodium; Gefitinib; Gemcitabine; Gemcitabine Hydrochloride; Gold Au 198; Hydroxyurea; Idarubicin Hydrochloride; Ifosfamide; Ilmofosine; Imatinib mesylate; Interferon Alfa-2a; Interferon Alfa-2b ; Interferon Alfa-n1; Interferon Alfa-n3; Interferon Beta-I a; Interferon Gamma-I b; Iproplatin; Iressa; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxaliplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Safinol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Tamoxifen; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyade-nosine; 2-chloro-2'-deoxyadenosine; anisomycin; trichostatin A; hPRL-G129R; CEP-751; linomide.

Other chemotherapeutic agents include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones including desoxyepothilones (A, R.dbd.H; B, R.dbd.Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons;interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticarcinoma agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Chemotherapeutic agent supplementary potentiating agents are for example tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); Ca.sup.++ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor. An antiproliferative agent is for example Piritrexim Isethionate.

Example of Radioactive agents are Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125 Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Active derivatives of the chemotherapeutic agents as well as prodrugs are also part of this invention.

Since a common but tolerable side effect of chemotherapeutic agents is nausea and vomiting, it is obvious to someone skilled in the art that these effects are avelliatably by administering an anti-emetic in conjunction with the chemotherapeutic agent inducing nausea and/or vomiting. E.g. Ondansetron may be given p.o. in a dose of about 8 mg about 30 minutes before the nausea/vomiting inducing antineoplastic agent is administered. Of course other anti-emtics such as Hasaldol, Benadryl, and Ativan may also be used as needed. Therefore, in an alternative embodiment, the pharmaceutical composition of the present invention comprises further compounds to decrease side effects of the chemotherapeutic agent or the inhibitor of the TGF-beta system.

Radiation is applied in dosages of about 1 Gy to about 100 Gy, more preferred from about 20 to about 80 Gy and most preferred, e.g. for the treatment of astrocytomas, glioblastomas and gliomas from about 40 to about 60 Gy.

The dosage in preferred embodiments is fractionated which means that, from about 0.1 to about 10 Gy or from about 1 Gy to about 5 Gy or from about 1 Gy to about 2 Gy are applied in one session which is repeated several times during about 1 to about 20 weeks, about 2 to about 10 weeks or 4 to about 8 weeks. The chemotherapeutic agent and/or the inhibitor of the TGF-beta system, e.g., an antisense oligonucleotide is administered before, after or together with the radiation.

One cycle of radiation therapy as well as several cycles of radiation are possible, dependent of the reduction of tumor size.

The radiation usually is performed with $^{60}$Co. Radiation with neutrons, protons, negative pimesones or neutrone capture is applicable as well. It is clear to someone skilled in the art that the dosage is further dependant on the size of the tumor, the build of the patient and the kind of radiation applied. In special embodiments the dosage is about 2 to about 100 fold higher or lower as described above also dependant from the number of fractions the dosage is applied with.

In another embodiment the pharmaceutical composition comprising at least one chemotherapeutic agent and at least one inhibitor of the TGF-beta system such as an antisense oligonucleotide is used in combination with other procedures for the treatment of diseases. For example, a tumor may be treated conventionally with surgery and/or radiation and then the composition comprising the chemotherapeutic agent and at least one antisense oligonucleotide and/or at least one inhibitor of the TGF-beta system according to this invention is subsequently administered to the patient to extend the dormancy of micrometastases and to stabilize respectively reduce any residual neoplastic disease, i.e., a tumor.

In a preferred embodiment, the pharmaceutical composition comprising at least one chemotherapeutic agent and at least one inhibitor of the TGF-beta system, for example an antisesne oligonucleotide is administered to a site likely to harbor a metastatic lesion (that may or may not be clinically discernible at the time). A sustained release formulation implanted specifically at the site (or the tissue) where the metastatic lesion is likely to be is suitable in these latter instances.

The embodiments of the pharmaceutical composition comprising at least one chemotherapeutic agent and at least one inhibitor of the TGF-beta system such as an antisense oligonucleotide, for example a TGF-beta 2 antisense oligonucleotide such as SEQ ID No. 30 administered in an effective amount. In general, the term "effective amount" of a pharmaceutical composition, a chemotherapeutic agent, and an inhibitor of the TGF-beta system, respectively, refers to the amount necessary or sufficient to realize a desired biologic effect. This depends amongst others on the mode of delivery (e.g., local or systemic), time period of the dosage, age, weight, general health, sex and diet of the subject receiving the pharmaceutical composition. Specifically, the effective amount is that amount that reduces the rate or inhibits altogether formation of neoplastis diseases. For instance, when the subject bears a tumor, an effective amount is that amount which decreases or eliminates the neoplastic disease. Additionally, an effective amount may be that amount which prevents an increase or causes a decrease in new neoplastic diseases. The effective amount varies depending upon whether the composition is used in single or multiple dosages. Dosages given in this writing are for adults. It is quite clear to someone skilled in the art that these dosages have to be adapted if the human being is a child, a person stressed by a further illness or other circumstances.

In one embodiment subject doses of the compounds described herein typically range from about 0.1 µg to about 10 mg per administration, which depending on the application could be given hourly, daily, weekly, or monthly and any other amount of time therebetween. In yet another embodiment the doses range from about 10 µg to about 5 mg per administration or from about 100 µg to about 1 mg, with 1-10 administrations being spaced hours, days or weeks apart. In some embodiments, however, doses may be used in a range even 2 to 100 fold higher or lower than the typical doses described above. These doses are mainly referring to the treatment of adults; in case of the treatment of a child, the doses have to be reduced as known by a skilled person.

The effect of a compound is indicated for example by its $IC_{50}$, the half maximal inhibitory concentration, which represents the concentration of an inhibitor that is required for 50% inhibition of its target, i.e., it measures how much of a particular substance/molecule is needed to inhibit some biological process by 50%. According to the present invention, the $IC_{50}$ of the chemotherapeutic agent describes the concentration of the chemotherapeutic agent that results in 50% cytotoxicity. The $IC_{50}$ describes the efficiency of a compound, the lower the $IC_{50}$ of a compound, the more effective the compound. In a preferred embodiment, the antisense oligonucleotide, in particular the antitumoral antisense oligonucleotide such as TGF-beta 1, -2, or -3 leads to a 1.5×, 2×, 2.5×, 5×, 5.5×, 6×, 6.5×, 7×, 7.5×, 8×, 8.5×, 9×, 9.5×, 10×, 15×, 20×, 25×, 30×, 35×, 40×, 45×, 50×, 55×, 60×, 65×, 70×, 75×, 80×, 85×, 90×, 95×, or 99× reduction of the $IC_{50}$ of the chemotherapeutic agent, preferably gemcitabine. Preferably, the $IC_{50}$ of the chemotherapeutic agent such as gemcitabine or temozolomide is 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% reduced by the antisense oligonuclotide, e.g., a TGF-beta 1, -2, and/or -3 antisense oligonucleotide, and/or an inhibitor of the TGF-beta system in comparison to gemcitabine without an antisense oligonucleotide, particularly a TGF-beta 1, -2, and/or -3 antisense oligonucleotide. The reduction of the $IC_{50}$ of the chemotherapeutic agent allows reaching the same cytotoxic effect with a lower concentration of the chemotherapeutic agent, or an increased cytotoxic effect with the same concentration of the chemotherapeutic agent. In a preferred embodiment, the inhibitor of the TGF-beta system reduces the $IC_{50}$ of the chemotherapeutic agent in a dose dependent manner.

Surprisingly, the chemotherapeutic agent does neither influence the expression or activity of the target of the inhibitor of the TGF-beta system such as the antisense oligonucleotide, which lead to the $IC_{50}$ reduction of the chemotherapeutic agent, nor the interaction of the the inhibitor of the TGF-beta system, e.g., the antisense oligonucleotide with the target. The chemotherapeutic agent even supports and increases the interaction of the inhibitor of the TGF-beta system, e.g., the antisense oligonucleotide, with the target. A preferred target of the antisense oligonucleotide is TGF-beta 1, -2, and/or -3.

In one embodiment of this invention the at least one inhibitor of the TGF-beta system, in particular the TGF-beta 1, -2, or -3 antisense oligonucleotide is administered in a dose range from about 1 µg/kg/day to about 100 mg/kg/day or from about 10 µg/kg/day to about 10 mg/kg/day or from about 100 µg/kg/day to about 1 mg/kg/day.

In a further preferred embodiment, the pharmaceutical composition is administered with a catheter directly into the tumor. The concentrations of the antinsense oligonucleotides are from about 0.1 µM/L to about 1 M/L, more preferred from about 1 µM/L to about 500 µM/L and even more preferred from about 10 to about 200 µM/L or from about 50 µM/L to about 150 µM/L in a steril aqueous solution. In yet another preferred embodiment this solution is administered with a flow of about 0.1 µL/min to about 50 µL/min or about 2 µL/min to about 12 µL/min or about 3 µL/min to about 10 µL/min into the tumor.

In yet another embodiment the at least one chemotherapeutic agent is selected from the group of nitrosourea, more preferred BCNU, CCNU and/or ACNU in combination with at least an inhibitor of the TGF-beta system, e.g., an antisense oligonucleotide such as TGF-beta1, -beta2- or -beta3 antisense oligonucleotide. The chemotherapeutic agent such as gemcitabine or temozolomid is for example administered in a dose range from about 1 mg/m$^2$ to about 1000 mg/m$^2$, more preferred in a dose of about 50 mg/m$^2$ to about 500 mg/m$^2$ and most preferred in a single dose of about 150 mg/m$^2$ to 200 mg/m$^2$ intravenously every 6 weeks. It may be given as a single dose or divided into daily injections such as about 75 mg/m$^2$ to about 100 mg/m$^2$ on two successive days.

In yet another embodiment in the treatment of neoplastic diseases the chemotherapeutic agent is gemcitabine and is administered with at least an inhibitor of the TGF-beta system such as an antisense oligonucleotide, and/or radiation at a dosage of about 10 mg/m$^2$ to about 10 g/m$^2$, more preferred from about 100 mg to about 5 g/m$^2$ and most preferred from about 500 mg/m$^2$ to about 2000 mg/m$^2$.

Gemcitabine is preferably administered within about 10 min to about 120 min, more preferred within about 15 min to about 60 min and most preferred within about 20 min to about 40 min. before or after administration of the antisense oligonucleotides. In a most preferred embodiment, gemcitabine is coadministered with one or more antisense oligonucleotides at the same time, wherein gemcitabine and the antisense oligonucleotide such as SEQ ID No. 30 are administered separately or in combination. In a preferred embodiment a single dose of the chemotherapeutic agent such as gemcitabine is administered repeatedly within about 4 to about 10 days, respectively about 5 to about 8 days and most preferred within about 7 days. About 1 to about 8, more preferred about 2 to about 6 most preferred about 3 to about 4 single doses are administered within about 4 to about 10 days, respectively about 5 to about 8 days and most preferred within about 7 days. After this a therapy free interval of about 2 to about 60 days, more preferred about 5 to about 30 days and most preferred from about 10 to about 20 days is applied. Several repetitions of these cycles are possible, e.g., 1 to 10, 2 to 10, 3 to 10, 4 to 10, 5 to 10, 6 to 10, 7 to 10, 8 to 10, or 9 or 10.

In yet another embodiment at least one chemotherapeutic agent is temozolomide and is administered with a total dose of about 500 to about 1200 mg/m$^2$, over a period from about 2 to about 28 consecutive days, more preferable over a period of from about 4 to about 7 consecutive days, and most preferably over a period of about 5 consecutive days. Thus, if the total dose is to be about 1000 mg/m$^2$ administered over a period of about 5 days, the daily dose for this period is about 200 mg/m$^2$/day. Temozolomide is administered at least once per day. Preferably dosing regimes would be twice per day, three times per day or four times per day. After a period of about 28 to about 42 days, or about 28 to about 35 days, or more preferably 28 days, from the first day of temozolomide administration, another administration cycle may be started.

In yet another embodiment the temozolomide may be administered for a much longer period at reduced dosage. For example, the temozolomide is administered more than once daily for up to six weeks at a daily dosage of about 50 mg/m$^2$/day to about 150 mg/m$^2$, of about 50 mg/m$^2$/day to about 75 mg/m$^2$/day, most preferably of about 75 mg/m$^2$/day. More preferred these daily doses are split about evenly into two or more doses to be administered two or more times per day.

In yet another embodiment vinblastin is administered at a dosage of about 0.1 mg/m$^2$ to about 50 mg/m$^2$ more preferred in a dose of about 1 mg/m$^2$ to about 10 mg/m$^2$ and even more preferred at about 4 mg/m$^2$ to about 8 mg/m$^2$.

In a further embodiment vincristin is administered at a dose of about 0.1 mg/m$^2$ to 10 mg/m$^2$ more preferred in a dose of about 0.5 mg/m$^2$ to about 5 mg/m$^2$ and more preferred at about 0.8 mg/m$^2$ to about 2 mg/m$^2$ about once a week whereas the neurotoxicity is the dosage limiting factor. Most commonly solution of vincristin sulfate from about 0.1 mg/mL to about 10 mg/mL are administered with single doses of about 0.1 mg/m$^2$ to about 50 mg/m$^2$ more preferred in a dose of about 0.5 mg/m$^2$ to about 10 mg/m$^2$ and even more preferred from about 1 mg/m$^2$ to about 5.0 mg/m$^2$.

In one embodiment, a pharmaceutical composition for the treatment of pancreas carcinoma, glioblastoma and/or anaplastic astrocytoma comprises a combination of at least one antisense oligonucleotide, e.g., a TGF-beta 1, -2, and/or -3 antisense oligonucleotide, preferably a TGF-beta antisense oligonucleotide of SEQ ID NO. 1 to 78, and a chemotherapeutic agent preferably selected from the group consisting of temozolomide, ACNU, BCNU, CCNU, vinblastine, vincristine, vindesine and their active derivatives, 5-fluorouracile, 5-fluorodeoxiuridine, cytarabine, gemicitabine, liposomal pegylated doxorubicine, procarbazine and vincristin.

In another embodiment the chemotherapeutic agents procarbazine, CCNU and vincristin are administered together with an antisense oligonucleotide identified in the sequence listing under SEQ ID NO. 1-127 and even more preferred in SEQ ID NO. 22-48, and/or an inhibitor of the TGF-beta system. The dosage in this embodiment is about 40 mg/m$^2$ to about 80 mg/m$^2$ of procarbazine p.o. (days about 8 to about 21 from the beginning of administration), about 80 to about 120 mg/m$^2$ CCNU, p.o. (about day 1 of administration), vincristine from about 1.2 mg/m$^2$ to about 1.8 mg/m$^2$ p.o. (day 1 of administration) with a maximum of about 2 mg/m$^2$ i.v. at about day 8, and about day 29 (from the beginning of administration). The antisense oligonucleotide and/or the inhibitor of the TGF-beta system is given before, with or after the administration of the chemotherapeutic agent, i.e., in general the compounds of the pharmaceutical composition of the present invention are administered at the same time, timely overlapping, or timely distinct. In another embodiment this cycle is repeated after about 6 to about 8 weeks once or several times.

In a further preferred embodiment the at least one antisense oligonucleotide, even more preferred an antisense oligonucleotid of TGF-beta 1, -2, or -3, and most preferred, an antisense oligonucleotide identified in the sequence listing under SEQ ID NO. 1-127 and even more preferred the sequences with SEQ ID NO. 22-48 and telozolomide are the parts of the pharmaceutical composition. In this case the dosage of temozolomide for the treatment of a neoplastic disease, more preferred cancer such as pancreatic carcinoma, glioma, glioblastoma and/or anaplastic astrocytoma is from about 120 to about 180 mg/m$^2$, p.o. on day 1 to 5 of a cycle. In a more preferred embodiment the antisense oligonucleotide is administered from about 1 µg/kg/day to about 50 mg/kg/day. The cycle is repeated after about 3 to 5 weeks.

In a further preferred embodiment for the treatment of glioma, radiation is further administered according to standard schedules as described above. In one embodiment the radiation is applied together with the administration of the combination as described above. In other embodiments the radiation is applied before or after the administration of the pharmaceutical compositions according to this invention.

In one embodiment of pharmaceutical compositions for the treatment of neoplastic diseases, more preferred pancreatic neoplasms at least one chemotherapeutic agent inhibiting cell proliferation and/or inducing cell death is selected from the group of cisplatin, carboplatin, cyclophosphamid, docetaxel, PEG-liposomal doxorubicin, etoposid, folinicc acid, 5-fluorouracil, mitoxantrone, paclitaxel, topotecan and/or treosulfan.

In more preferred embodiments for the treatment of neoplastic diseases the chemotherapeutic agents paclitaxel or carboplatin are the at least one part of a pharmaceutical composition according to this invention. Paclitaxel from about 100 mg/m$^2$ to about 200 mg/m$^2$ more preferred about 175 mg/m$^2$ or carboplatin administered i.v. at day 1 of a cycle. This cycle is repeated after about 20 to about 30 days.

In yet another embodiment for the treatment of neoplastic diseases such as pancreatic carcinoma the at least one chemotherapeutic agent of a pharmaceutical composition according to this invention is gemcitabine. Gemcitabine is administered in dosages of about 800 mg/m$^2$ to about 1200 mg/m$^2$, more preferred about 1000 mg/m$^2$ i.v. within about 10 min to about 60 min, more preferred within about 12 min to about 20 min. This application is repeated for about 5 to about 10 days.

In yet other embodiments paclitaxel together with carboplatin, docetaxel together with carboplatin, carboplatin together with cyclophosphamid, cisplatin together with treosulfan, etoposid, mitoxantron together with folin acid and 5-fluorouracil, topotect, or PEG-liposomal doxorubicin are the at least one chemotherapeutic agent of a pharamaceutical composition according to this invention for the treatment of pancreatic cancer.

In a more preferred embodiment of the above mentioned embodiments for the treatment of pancreatic cancer the antisense oligonucleotide is an oligonucleotide identified in the sequence listing under SEQ ID NO. 1-127 and even more preferred the sequence with SEQ ID NO. 22-48.

In a further preferred embodiment, the antisense oliogonucleotide is administered in a dose of 1, 5, 10, 15, 20, 25, 30, 35, 40, 45, 50, 55, 60, 65, 70, 75, 80, 85, 90, 95, or 100 μM.

In another embodiment further to the adminstration of these pharmaceutical compositions, radiotherapy is applied according to standard schedules as described above.

Alternatively, to the local administration of the pharmaceutical composition of the present invention, the composition is administered systemically in a preferred embodiment.

The pharmaceutical composition of the present invention preferably comprises at least one chemotherapeutic agent such as gemcitabine or temozolomide and at least one inhibitor of the TGF-beta system such as a TGF-beta 2 antisense oligonucleotide, for example SEQ ID No. 30, forming the components of the pharmaceutical composition. These components are either in pure form mixed together, or together with a pharmaceutically acceptable carrier, lubricant, diluent, excipient, disintegrate, and/or adjuvant mixed together. In an alternative embodiment the components of the pharmaceutical composition are separate, either in pure form, or together with a pharmaceutically acceptable carrier, lubricant, diluent, excipient, disintegrate, and/or adjuvant. In a preferred embodiment, the pharmaceutically acceptable carrier, lubricant, diluent, excipient, disintegrate, and/or adjuvant of the components is identical or different.

"Administering" the pharmaceutical compositions of the present invention is accomplished by any means known to a person skilled in the art. Routes of administration include but are not limited to oral, intranasal, intratracheal, ocular, pulmonal, vaginal, rectal, parenteral (e.g. intramuscular, intradermal, intravenous, intratumoral or subcutaneous or direct injection), depo injection, implantation, time-release mode, intracranial, intraperitoneal, intravesical, subconjunctival, topical, transdermal, or sublingual.

In one embodiment of a pharmaceutical composition for the treatment of neoplastic diseases forming a tumor such as cancer, the combination of at least one chemotherapeutic agent and the at least one inhibitor of the TGF-beta system such as an antisense oligonucleotide are preferably delivered by means of a biodegradable, polymeric implant or implanted catheter.

The term "pharmaceutical composition" refers to compositions comprising the components in solid and/or liquid form, wherein the components are in pure form and/or together with a pharmaceutically acceptable carrier, filler, lubricant, diluent, excipient, disintegrate, and/or adjuvant.

Pharmaceutical acceptable carrier, filler, lubricant, diluent, excipient, disintegrate, and/or adjuvant according to the present invention is any substance suitable for administration to a subject, which are of organic or inorganic origin, natural or synthetic origin, and with which a component of the pharmaceutical composition is for example combined to facilitate the application, or to increase the efficiency of the component. Preferably, a carrier, filler, lubricant, diluent, excipient, disintegrate, and/or adjuvant enables the components of the pharmaceutical composition or the pharmaceutical composition to be formulated as tablet, coated tablet, evervescent tablet, granules, lozenge, powder, pill, dragee, (micro)capsule, liquid, gel, syrup, slurry, suspension, emulsion and the like, for oral ingestion by a subject to be treated.

The pharmaceutical compositions also include granules, powders, tablets, coated tablets, (micro)capsules, suppositories, syrups, emulsions, suspensions, creams, drops, coated onto microscopic gold particles or preparations with protracted release of the components, in whose preparation excipients and additives and/or auxiliaries such as disintegrants, binders, coating agents, swelling agents, lubricants, flavorings, sweeteners or solubilizers are customarily used as described above. For a brief review of present methods for drug delivery, see Langer (1990).

In one embodiment pharmaceutical preparations for oral use are obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

In yet another embodiment disintegrating agents are added, such as the cross-linked polyvinyl pyrrolidone, agar, or alginic acid or a salt thereof such as sodium alginate. Optionally the oral formulations may also be formulated in saline or buffers for neutralizing internal acid conditions.

In yet another embodiment dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures.

In yet another embodiment dyestuffs or pigments are added to the tablets or dragee coatings for identification or to characterize different combinations of active compound doses. In another embodiment pharmaceutical preparations, which can be used orally "vegicaps" include push-fit capsules made of gelatin, as well as soft, sealed capsules made of gelatin and a plasticizer, such as glycerol or sorbitol. In one embodiment the push-fit capsules containes the active ingredient in a mixture with filler such as lactose, binders such as starches, and/or lubricants such as talc or magnesium stearate and, optionally, stabilizers. In another embodiment of the soft capsules, the active compounds are dissolved or suspended in suitable liquids, such as fatty oils, liquid paraffin, or liquid polyethylene glycols. In addition, stabilizers may be added. In yet another embodiment microspheres formulated for oral administration are used, wellknown to someone skilled in the art. The formulations for oral administration are in dosages suitable for such administration.

In yet another embodiment for buccal administration, the compositions take for example the form of tablets or lozenges formulated in conventional manner.

In yet another embodiment for the administration by inhalation, the compounds for use according to the present invention may be conveniently delivered in the form of an aerosol spray, from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Suitable pharmaceutical carriers are, for example, aqueous or saline solutions for inhalation, microencapsulated, encochleated, contained in liposomes, nebulized, aerosols.

In yet another embodiment the pharmaceutical acceptable carriers of the compounds, e.g., for oral, intravenous, intracaranial, intraperitoneal, intravesicel, topical, transdermal, subconjunctival, sublingual, parenteral, depo injection, time-release mode, intrathecal, intraventricular or intratumoral administration include sterile aqueous solutions which may also contain buffers, diluents and other suitable additives such as, but not limited to, penetration enhancers, carrier compounds and other pharmaceutical acceptable carriers, fillers, lubricants, diluents, excipients, disintegrates, and/or adjuvants.

In yet another embodiment for the systemic delivery of the pharmaceutical composition or its components, they are for example together with a pharmaceutical carrier, filler, lubricant, diluent, excipient, disintegrate, and/or adjuvant for parenteral administration by injection (e.g., by bolus injection or continuous infusion). Formulations for injection are for example presented in unit dosage form, e.g., in ampoules or in multi-dose containers, with an added preservative. Prefreably, the pharmaceutical compositions take such forms amongst others as suspensions, solutions or emulsions in oily or aqueous vehicles, and contain formulatory agents such as suspending, stabilizing and/or dispersing agents. In one embodiment pharmaceutical carriers, fillers, lubricants, diluents, excipients, disintegrates, and/or adjuvants for parenteral administration include aqueous solutions of the active compounds in water-soluble form.

In yet another embodiment a suspension of one or more components of the pharmaceutcal composition of the invention is prepared as appropriate oily injection suspension. Suitable lipophilic solvents or vehicles include fatty oils such as sesame oil, or synthetic fatty acid esters, such as ethyl oleate or triglycerides, or liposomes. Aqueous injection suspensions comprise substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

In yet another embodiment the chemotherapeutic agent and/or the inhibitor of the TFG-beta system, e.g., an antisense oligonucleotide is in powder form for constitution with a suitable vehicle, e.g., sterile pyrogen-free water, before use or dried onto a sharp object to be scratched into the skin.

In yet another embodiment the compounds are formulated in rectal or vaginal compositions such as suppositories or retention enemas or tablets, e.g., containing conventional suppository bases such as cocoa butter or other glycerides.

In yet another embodiment the compounds are formulated as a depot preparation. In one embodiment such long acting formulations are formulated with suitable polymeric or hydrophobic materials (for example as an emulsion in an acceptable oil) or ion exchange resins, or as sparingly soluble derivatives, for example as a sparingly soluble salt. In other embodiments delivery systems include time-release, delayed release or sustained release delivery systems. Such systems can avoid repeated administrations of the compounds, increasing convenience to the subject and the physician. Many types of release delivery systems are available and known to those of ordinary skill in the art. In an alternative embodiment the delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109.

In another embodiment the delivery systems include non-polymer systems that are e.g. lipids including sterols such as cholesterol, cholesterol esters and fatty acids or neutral fats such as mono-, di- and triglycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, preferably pump-based hardware delivery systems are used, some of which are adapted for implantation.

In a further embodiment, the chemotherapeutic agent and/or the antisense oligonucleotide and/or the inhibitor of the TGF-beta system is formulated with GELFOAM®, a commercial product consisting of modified collagen fibers that degrade slowly. Moreover, the pharmaceutical compositions also comprise for example suitable solid or gel phase carriers, fillers, lubricants, diluents, excipients, disintegrates, and/or adjuvants. Examples of such carriers, fillers, lubricants, diluents, excipients, disintegrates, and/or adjuvants include, but are not limited to calcium carbonate, calcium phosphate, various sugars, starches, cellulose derivatives, gelatin, and polymers such as polyethylene glycols.

Preferably the chemotherapeutic agent and/or the antisense oligonucleotide and/or the inhibitor of the TGF-beta system is administered neat or in the form of a pharmaceutical acceptable salt. The salts have to be pharmaceutical acceptable, but non-pharmaceutical acceptable salts may conveniently be used to prepare pharmaceutical acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

In one embodiment suitable buffering agents include but are not limited to: acetic acid and a salt (1-2% w/v); citric acid and a salt (1-3% w/v); boric acid and a salt (0.5-2.5% w/v);

and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

In one embodiment the pharmaceutically acceptable carrier for topical administration for the at least two components of a pharmaceutical composition according to this invention include transdermal patches, ointments, lotions, creams, gels, drops, suppositories, sprays, liquids and powders. Conventional pharmaceutical carriers, aqueous, powder or oily bases, thickeners and the like may be necessary or desirable. In yet another embodiment coated condoms, gloves and the like are useful. In yet another embodiment the pharmaceutical compositions include penetration enhancers in order to enhance the alimentary delivery. Penetration enhancers may be classified as belonging to one of five broad categories, i.e., fatty acids, bile salts, chelating agents, surfactants and non-surfactants (Lee et al. 1991, Muranishi 1990). Preferably, one or more penetration enhancers from one or more of these broad categories are included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al. 1991, Muranishi 1990, El-Hariri et al. 1992). Examples of some presently preferred fatty acids are sodium caprate and sodium laurate, used singly or in combination at concentrations of 0.5 to 5%. The physiological roles of bile include the facilitation of dispersion and absorption of lipids and fat-soluble vitamins (Brunton 1996). Various natural bile salts, and their synthetic derivatives, act as penetration enhancers. Thus, the term "bile salt" includes any of the naturally occurring components of bile as well as any of their synthetic derivatives. A presently preferred bile salt is chenodeoxycholic acid (CDCA) (Sigma Chemical Company, St. Louis, Mo.), generally used at concentrations of 0.5 to 2%. In a preferred ambodiment, complex formulations comprising one or more penetration enhancers are used. For example, bile salts are used in combination with fatty acids to make complex formulations. Preferred combinations include CDCA combined with sodium caprate or sodium laurate (generally 0.5 to 5%).

In one embodiment additionally chelating agents are used that include, but are not limited to, disodium ethylenediaminetetraacetate (EDTA), citric acid, salicylates (e.g., sodium salicylate, 5-methoxysalicylate and homovanillate), N-acyl derivatives of collagen, laureth-9 and N-amino acyl derivatives of beta-diketones (enamines) (Lee et al. 1991; Muranishi 1990; Buur et al. 1990). Chelating agents have the added advantage of also serving as DNase inhibitors.

In yet another embodiment additionally surfactants are used. Sufactants include, for example, sodium lauryl sulfate, polyoxyethylene-9-lauryl ether and polyoxyethylene-20-cetyl ether (Lee et al. 1991); and perfluorochemical emulsions, such as FC-43 (Takahashi et al. 1988). Non-surfactants include, for example, unsaturated cyclic ureas, 1-alkyl- and 1-alkenylazacyclo-alkanone derivatives (Lee et al. 1991); and non-steroidal anti-inflammatory agents such as diclofenac sodium, indomethacin and phenylbutazone (Yamashita et al. 1987).

In one embodiment the pharmaceutical compositions of the present invention additionally contain other adjunct components conventionally found in pharmaceutical compositions, at their art-established usage levels. Thus, for example, the compositions may contain additional compatible pharmaceutically active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

EXAMPLES

The present invention is demonstrated in the following examples, however, the invention is not limited to these examples.

Example 1

TGF-Beta 2 Antisense Oligonucleotide Reducing the $IC_{50}$ of Gemcitabine (FIG. 1)

In a 96-well tissue culture plate 4000 cells/well of a human pancreatic tumor cell line Hup-T3 (German Collection of Microorganisms and Cell Cultures GmbH, Braunschweig, Germany) were seeded. The Hup-T3 cell line is not resistant to gemcitabine. One day after seeding, cells were co-treated with eight different gemcitabine concentrations, i.e., 5 µM, 2 µM, 800 nM, 320 nM, 128 nM, 51.2 nM, 20.5 nM, 8.2 nM, 3.3 nM and 0 nM gemcitabine, respectively, in combination with 0 µM (■), 5 µM (Δ) or 10 µM (∇) TGF-beta 2 antisense oligonucleotide, for example SEQ ID No. 30, for 5 h. Thereafter the first treatment solution comprising gemcitabine and the TGF-beta 2 antisense oligonucleotide was removed and replaced by a second treatment solution containing the TGF-beta 2 antisense oligonucleotide, but no gemcitabine. The treatment solution was optionally replaced after 3 days.

After 7 days of total treatment, cell supernatants were removed and the TGF-beta 2 concentration was analyzed (see Example 4, and FIG. 4).

The proliferation/viability of the Hup-T3 cells was analyzed using the EZ4U method according to the manufacturer's instructions (Biozol Diagnostca Vertrieb GmbH), and the OD was measured after an incubation time of 75 min with EZ4U solution using the plate reader "Fluostar-Optima" (BMG LABTECH GmbH). The results show an unexpected increase in the inhibition of cell proliferation by gemcitabine, when gemcitabine was administered in combination with the TGF-beta 2 antisense oligonucleotide. Thus, the TGF-beta 2 antisense oligonucleotide surprisingly reduced the $IC_{50}$ of gemcitabine in a dose dependent manner (FIG. 1).

Example 2

Effect of Gemcitabine on TGF-Beta 2 Secretion (FIG. 2)

The effect of gemcitabine on TGF-beta 2 expression and secretion, respectively, was investigated on Hup-T3 cells. Gemcitabine was administered to the Hup-T3 cells in following concentrations: 5 µM, 0.5 µM, 50 nM, 5 nM, 0.5 nM, 0.05 nM or 0 nM, and the cells were incubated for 5 h according to Example 1. The treatment solution was optionally replaced after 3 days.

After 7 days of treatment, cell supernatants were removed for the analysis of TGF-beta 2 concentration. The TGF-beta 2 secretion (Δ) was quantified by a standard TGF-beta 2-ELISA Kit (R&D Systems, Minneapolis, USA) according to the manufacturer's instructions.

The proliferation/viability of the Hup-T3 cells (■) was analyzed using the EZ4U method according to the manufacturer's instructions (Biozol Diagnostca Vertrieb GmbH), and the OD was measured after an incubation time of 75 min with EZ4U solution using the plate reader "Fluostar-Optima" (BMG LABTECH GmbH).

The decrease of TGF-beta 2 secretion (Δ) correlates to the proliferation and viability (■), respectively, of the cells, which decreases at higher gemcitabine concentrations due to the cytotoxic effect of gemcitabine. This is shown by the overlapping curves of FIG. 2. Surprisingly, gemcitabine has a cytotoxic effect, but does not specifically influence the TGF-beta 2 secretion of Hup-T3 cells (Δ) (see FIG. 2).

Example 3

Effect of the TGF-Beta 2 Antisense Oligonucleotide on TGF-Beta 2 Secretion (FIG. 3)

In a further experiment the effect of the TGF-beta 2 antisense oligonucleotide on the expression and secretion, respectively, of TGF-beta 2 was investigated on Hup-T3 cells. The TGF-beta 2 antisense oligonucleotide, for example SEQ ID No. 30, was administered to the Hup-T3 cells as described in Example 1 (0 μM, 1 μM, 2.5 μM, 5 μM, 10 μM, 20 μM, 40 μM, 60 μM, or 80 μM TGF-beta 2 antisense oligonucleotide). The cells were incubated according to Example 1 and after 7 days of treatment, the cell supernatants were removed for the analysis of TGF-beta 2 concentration using the TGF-beta 2-ELISA Kit of R&D Systems.

As expected, the TGF-beta 2 antisense oligonucleotide inhibited the TGF-beta 2 expression and secretion, respectively, in a dose dependent manner (see FIG. 3).

Example 4

Effect of Gemcitabine on the Suppression of TGF-Beta 2 Secretion by TGF-Beta 2 Antisense Oligonucleotide (FIG. 4)

Hup-T3 cells were incubated with different concentrations of gemcitabine (2 μM, 800 nM, 320 nM, 128 nM, 51.2 nM, 20.5 nM, 8.2 nM, and 0 nM) and TGF-beta 2 antisense oligonucleotide according to Example 1 (0 μM (■), 5 μM (Δ), or 10 μM (•) TGF-beta 2 antisense oligonucleotide) and the cell supernatants were removed after 7 days of treatment for the analysis of TGF-beta 2 concentration using the TGF-beta 2-ELISA Kit of R&D Systems.

Surprisingly, gemcitabine does not negatively influence the interaction of TGF-beta 2 antisense oligonucleotide with its TGF-beta 2 target, i.e., gemcitabine does not impair the suppression of TGF-beta 2 secretion via the TGF-beta 2 antisense oligonucleotide.

Example 5

TGF-Beta 2 Antisense Oligonucleotide Reducing the $IC_{50}$ of Temozolomide (FIG. 5)

In a 48-well tissue culture plate 10 000 cells/well of a human melanoma cell line MEL-Juso (CLS—Cell Lines Service, Eppelheim, Germany) were seeded. The MEL-Juso cell line is not resistant to temozolomide. Six hours after seeding, cells were co-treated with eight different temozolomid concentrations, i.e., 200 μM, 100 μM, 50 μM, 25 μM, 12.5 μM, 6.25 μM, 3.125 μM, and 0 μM temozolomide, respectively, in combination with 0 μM (■), 5 μM (Δ) or 10 μM (▽) TGF-beta 2 antisense oligonucleotide, for example SEQ ID No. 30, for 2 days. Substances (temozolomide and TGF-beta 2 antisense oligonucleotide) were prepared in aqueous solution, stored at 4° C. and were used for 4 weeks. Thereafter the first treatment solution comprising temozolomidee and the TGF-beta 2 antisense oligonucleotide was removed and replaced by a second treatment solution containing the TGF-beta 2 antisense oligonucleotide and temozolomide in the above mentioned concentrations for further 2 days. The treatment solution containing the TGF-beta 2 antisense oligonucleotide and temozolomide was removed, and fresh test solution was added to the cells for further 3 days.

After 7 days of total treatment, cell supernatants were removed and the TGF-beta 2 concentration was analyzed.

The proliferation/viability of the MEL-Juso cells was analyzed using the Cyquant method according to the manufacturer's instructions (Invitrogen), and the OD was measured after an incubation time of 60min with Cyquant solutions (detection reagent, direct nucleic acid stain, and direct nucleic acid background suppressor) using the plate reader "Fluostar-Optima" (BMG LABTECH GmbH). The results show an unexpected increase in the inhibition of cell proliferation by temozolomide, when temozolomide was administered in combination with the TGF-beta 2 antisense oligonucleotide. Thus, the TGF-beta 2 antisense oligonucleotide surprisingly reduced the $IC_{50}$ of temozolomide in a dose dependent manner (FIG. 5).

Example 6

TGF-Beta 2 Antisense Oligonucleotide Increasing Temozolomide's Cytotoxicity (FIG. 6)

A-172 cells (about 7000 cells/well) were seeded into 48-well plates, and 6 h after seeding 0 μM, 200 μM, or 800 μM temozolomide either alone (grey column) or in combination with 10 μM of a TGF-beta 2 antisense oligonuclotide (black column), for example SEQ ID No. 30, was added to the cells. After 2 d of incubation, the treatment solutions were replaced and cells were incubated for additional 3 d (total treatment time: 5 d). Thereafter, cell supernatants containing lactate dehydrogenase (LDH) from lysed cells and of cells floating in the supernatant, as a result of treatment induced stress, were removed from the wells. The cells of the supernatant were lysed by addition of lysis solution for example from the CytoToxicity Detection Kit Plus (Roche Diagnostics GmbH) and the LDH levels were determined for example according to the manual of the kit. The amount of released LDH significantly increased with the combination of temozolomide and the TGF-beta 2 antisense oligonucleotide (FIG. 6).

Example 7

Antisense m-RNA for the human transforming growth factor TGF-beta 1, -2, and -3:
Antisense m-RNA for the human TGF-beta 1:
(SEQ ID NO: 147)
CTGCAGCCTTGACCTCCCAGGATCAAGTGATCCTCCCACCTTAGCCT
CCAGAGTAGCTGGGACCACAGGTGTACATTTTTTAAAAGTGTTTTGT
AGAGATAGGGTCTCACTATGTTACCCAGGCTGGTCTCAAATGCCTGG
ATTCAAGTATCCTCCCATCTCTGCCTCCCAAAAGTGCTAGGATTACA
GGCGTGAGCACCCCGCCTGGCCTGAACTACTATCTTTTATTGTCTTC
TTCACTATCCCCCACTAAAGCAGGTTCCTGGTGGGCAGGAACTCCTC
CCTTAACCTCTCTGGGCTTTGTTTCCTCAACCTTTAAAATGGGTGTTA
TCAGAGTCCCTGCCATCTCAGAGTGTTGCTATGGTGACTGAATGAGT
TCATTAATGTAAGGCACTTCAACAGTGCCCAAGGTGCTCAATAAATA
GATCTAACTACAGTAGTGTTCCCCACTGGTCCCCTGTGCCTTGATGC
CGGGCAAAGGAATAGTGCAGACAGGCAGGAGGAGGCAGAGAGGGAGA
GAGAGGGAGTGGGAGTGGGGGAACGTCAGGGATGGAGACCCCAGGCA

```
GGCGCCCAATGACACAGAGATCCGCAGTCCTCCTCTCCATCTTTAATG
GGGCCCCAGGTGGGCTTGGGGCACGGTGTCCTTAAATACAGCCCCCA
TGGGCAAGGCAGCGGGGGCGGGGCGGGGTGGGGCCGGGCCTGCCGGG
GCGGGGCGGGGCGGGGCGGGACCTCAGCTGCACTTGCAGGAGCGCAC
GATCATGTTGGACAGCTGCTCCACCTTGGGCTTGCGGCCCACGTAGT
ACACGATGGGCAGCGGCTCCAGCGCCTGCGGCACGCAGCACGGCGCC
GCCGAGGCGCCCGGGTTATGCTGGTTGTACAGGGCCAGGACCTTGCT
GTACTGCGTGTCCAGGCTCCAAATGTAGGGGCAGGGCCCGAGGCAGA
AGTTGGCATGGTAGCCCTTGGGCTCGTGGATCCACTTCCAGCCGAGG
TCCTTGCGGAAGTCAATGTACAGCTGCCGCACGCAGCAGTTCTTCTC
CGTGGAGCTGAAGCAATAGTTGGTGTCCAGGGCTCGGCGGTGCCGGG
AGCTTTGCAGATGCTGGGCCCTCTCCAGCGGGGTGGCCATGAGAAGC
AGGAAAGGCCGGTTCATGCCATGAATGGTGGCCAGGTCACCTCGGCG
GCCGGTAGTGAACCCGTTGATGTCCACTTGCAGTGTGTTATCCCTGC
TGTCACAGGAGCAGTGGGCGCTAAGGCGAAAGCCCTCAATTTCCCCT
CCACGGCTCAACCACTGCCGCACAACTCCGGTGACATCAAAAGATAA
CCACTCTGGCGAGTCGCTGGGTGCCAGCAGCCGGTTGCTGAGGTATC
GCCAGGAATTGTTGCTGTATTTCTGGTACAGCTCCACGTGCTGCTCC
ACTTTTAACTTGAGCCTCCTCAGCAGACACAGCTCTGCCCGGGAGAG
CAACACGGGTTCAGGTACCGCTTCTCGGAGCTCTGATGTGTTGAAGA
ACATATATATGCTGTGTGTACTCTGCTTGAACTTGTCATAGATTTCG
TTGTGGGTTTCCACCATTAGCACGCGGGTGCTGCACTCTTCCCCGCCCACCC
GTCGGCCTCAGGCTCGGGCTGCGGTTCTGCACTCTCCCCGGCCACCC
GGTCGCGGGTGCTGTTGTACAGGGCGAGCACGGCCTCGGGCAGCGGG
CCGGGCGGCACCTCCCCCTGGCTCGGGGGGCTGGCGAGCCGCAGCTT
GGACAGGATCTGGCCGCGGATGGCCTCGATGCGCTTCCGCTTCACCA
GCTCCATGTCGATAGTCTTGCAGGTGGATAGTCCCGCGGCCGGCCGG
CCAGGCGTCAGCACCAGTAGCCACAGCAGCGGTAGCAGCAGCGGCAG
CAGCCGCAGCCCGGAGGGCGGCATGGGGAGGCGGCGCCCCCCGGCA
CTGCCGAGAGCGCGAACAGGGCTGGTGGTGGGGAGGCCCCGCCCC
TGCAGGGGCTGGGGGTCTCCCGGCAAAAGGTAGGAGGGCCTCGAGGG
AAAGCTGAGGCTCCTCAGGGAGAAGGGCGCAGTGGTGGAGGGGAGGC
TTGGACCGGGGGTGTCTCAGTATCCCACGGAAATAACCTAGATGGGC
GCGATCTGGTACCAGAAGGTGGGTGGTCTTGAATAGGGGATCTGTGG
CAGGTCGGAGAGAGATCCGTCTCCTGGAGGAGAAAAGGGTCTAGGATG
CGCGGGGGCTCAGGAGACAGGCCGGGGATGAAGGCGGCGTGCAGGGG
GTGCGCCCGAGGTCTGGGGAAAAGTCTTTGCGGGAGGCCGGGTCGGC
GACTCCCGAGGGCTGGTCCGGAATGGGGGCGCCTGAGGGACGCCGTG
TAGGGGGCAGGGAGGGAGCAAGCGTCCCCGGCGGCAAAGGGAGGCGG
TCTGGGGTCCCCAAGTCCTGCCTCCTCGCGGGGCAGCGTCGCGCCAA
GAGGTCCCCGCGCCTCCGCTCCCAGCGGCAACGGAAAAGTCTCAAAA
GTTTTTTTCCTCTTTCTCCCGACCAGCTCGTCCCTCCTCCCGCTCCT
CCTCCCCCTCCTCCCCGCAGTGCGGGGGCGGCGGCGGCTCGTCTCA
GACTCTGGGGCCTCAGGCTGCTCCTCGGCGACTCCTTCCTCCGCTCC
GGGCCGAGGCCGGCCCCGCGGGCGGCTCAGAGCCGGGGGGGTGCCC
CGGACGGGCGTCCCCCCTGCCCCCGCCGGGGCCCTCGCTGTCTGG
CTGCTCCGCGGAGGGAGGT

Antisense m-RNA of the human TGF-beta 2:
                                    (SEQ ID NO: 148)
TTTAAAAAAATTTGCTTCTTGTCTCTCTCACTTACAAAGTAGGTGAA
ATGTAGAATAAGGCCTTCAACTTTTTTTGTGTCAGATGCCAGTTTTA
ACAAACAGAACACAAACTTCCAAAGTGTCTGAACTAGTACCGCCTTT
TCAAAATTTTTTAACACTGATGAACCAAGGCTCTCTTATGTTTTCTT
GTTACAAGCATCATCGTTGTCGTCGTCATCATCATTATCATCATCAT
TGTCATTTTGGTCTTGCCACTTTTTCCAAGAATTTTAGCTGCATTTGC
AAGACTTTACAATCATATTAGAAAGCTGTTCAATCTTGGGTGTTTTG
CCAATGTAGTAGAGAATGGTTAGAGGTTCTAAATCTTGGGACACGCA
GCAAGGAGAAGCAGATGCTTCTGGATTTATGGTATTATATAAGCTCA
GGACCCTGCTGTGCTGAGTGTCTGAACTCCATAAATACGGGCATGCT
CCAGCACAGAAGTTGGCATTGTACCCTTTGGGTTCGTGTATCCATTT
CCACCCTAGATCCCTCTTGAAATCAATGTAAAGTGGACGTAGGCAGC
AATTATCCTGCACATTTCTAAAGCAATAGGCCGCATCCAAAGCACGC
TTCTTCCGCCGGTTGGTCTGTTGTGACTCAAGTCTGTAGGAGGGCAA
TAACATTAGCAGGAGATGTGGGGTCTTCCCACTGTTTTTTTTCCTAG
TGGACTTTATAGTTTTCTGATCACCACTGGTATATGTGGAGGTGCCA
TCAATACCTGCAAATCTTGCTTCTAGTTCTTCACTTTTATTTGGGAT
GATGTAATTATTAGATGGTACAAAAGTGCAGCAGGGACAGTGTAAGC
TTATTTAAATCCCAGGTTCCTGTCTTTATGGTGAAGCATTCATGA
ACAGCATCAGTTACATCAAGGAGAGCCATTCGCCTTCTGCTCTTGT
TTTCACAACTTTGCTGTCGATGTAGCGCTGGGTTGGAGATGTTAAAT
CTTTGGACTTGAACATCTGATATAGCTCAATCCGTTGTTCAGGCACT
CTGGCTTTTGGGTTCTGCAAACGAAAGACTCTGAACTCTGCTTTCAC
CAAATTGGAAGCATTCTTCTCCATTGCTGAGACGTCAAATCGAACAA
TTCTGAAGTAGGGTCTGTAGAAAGTGGGCGGGATGGCATTTTCGGAG
GGGAAGAAGGGCGGCATGTCTATTTTGTAAACCTCCTTGGCGTAGTA
CTCTTCGTCGCTCCTCGCGCTCGCAGGCGGCCGCCCTCCGGCTCG
CCTTCTCCTGGAGCAAGTCCCTGGTGCTGTTGTAGATGGAAATCACC
TCCGGGGGACTTCCTCGGGCTCAGGATAGTCTTCTGGGGGACTGGT
GAGCTTCAGCTTGCTCAGGATCTGCCCGCGGATCGCCTCGATCCTCT
TGCGCATGAACTGGTCCATATCGAGTGTGCTGCAGGGTAGACAGGCTG
AGCGCGACCGTGACCAGATGCAGGATCAGAAAAGCGCTCAGCACACA
GTAGTGCATTTTTTAAAAAGTGGAAAAAAAAAGTTGTTTTTAAAAGT
CAGAATAAAAAAAAGAAATCAACAATTCTCAAAGTATAGATCAAGG
AGAGTTGTTTGGTTTTTTGTTGTTGTTGTTTGTTTTTGATGCGAAAC
TTTTGCAAACAATCTAGTCAATGCCCAACAGAAAAACGTATCCTGCT
TG Antisense of m-RNA of the human TGF-beta 3
                                    (SEQ ID NO: 149)
CAGGATGCCCCAAAAATATTTATTTATACAAAGATTTTGAGAGTAAT
ATTCATACTTGTCTTTATACCTCAGTCTATGCGTCTGGGGCCAAGTC
ACTGTGTGGCACATGTCGAGCTTCCCGAATGCCTCACATGTTGTCG
CACCTGCTTCCAGGAACACCAAATGAACACAGGGTCTTGGAGGGGAA
GTGGGGGAAGAACCCATAATGCCCCAACCCTGCATGGAACCACAATC
CAGAAATGTGCATCCTGACCTGGAAGGCGTCTAACCAAGTGTCCAAG
GGGAAATATGATCGAGGGAGAGGTGAGAGGAGGGACCCAGAGGCAGA
CAGGAGAGGGTTGATTTCCACCCTTTCTTCTGCGTTCAGCATATCCA
AAAGGCCCAATACAGTTGATGGGCCAGGAACTGCATGACCTGGATTT
TCTCCCTGTAGTGACCCACGATGTTAATTGATGTAGAGGACAGTTTG
CAAAAGTAATAGATTTGCCCTTAATCCCAGACAGTATGAGATACAAT
TCTGGGACTTTGTCTTCGTAACCTGTCTTTAAAAAAAAAAAAAAATG
CTTGCTTGTATAACATAATCCAGATTCCCTAGAGCAGATGTGGTAC
AGCAATGAGCAAATCCAACCTCAGATCTGAAGTGTCTTCCAGTCTGG
CCCTGACCCAGCCATTCTCTGCCCTTCCTTCTCCCTTTAGGGTAGCC
CAAATCCCATTGCCACACAACATCTCAACTTACCATCCCTTTCCTCT
ATCCCCATCCCCTCTGTCTGCGTCACAGAAAGTCTGTGTGTTCTGAA
GAGTTCAGCCTTCCTCTAACCAAACCCACACTTTCTTTACCACCGTG
ATTCTCAGAGCCAGCAAGAAAGAAATGTTCCAAAAGGAAACCTCCAT
CTCAGCCATTTGCCCGGAGCCGAAGGTTGTGGGCTCCAGGCCTCTCA
GTGAGGTTTGTTGCTTGTGTGTTTCCCGAGGAGCGGGCAGTCAGGCA
GTGGTGGTTCTCTCTCCCCTCTCTCTGTCGCACGTGGGGTCTCAGCT
ACATTTACAAGACTTCACCACCATGTTGGAGAGCTGCTCCACTTTGG
GGGTCCTCCCAACATAGTACAGGATGGTCAGGGGCTCCAGGTCCTGG
GGCACGCAGCAAGGCGAGGCAGGTGCTTCAGGGTTCAGAGTGTTGTA
CAGTCCCAGCACCGTGCTGTGGGTTGTGTCTGCACTGCGGAGGTATG
GGCAAGGGCCTGAGCAGAAGTTGGCATAGTAGCCCTTAGGTTCATGG
ACCCACTTCCAGCCCAGATCCTGTCGGAAGTCAATGTAGAGGGGGCG
CACACAGCAGTTCTCCTCCAAGTTGCGGAAGCAGTAATTGGTGTCCA
AAGCCCGCTTCTTCCTCTGACCCCCCTGGCCCGGGTTGTCGAGCCGG
TGTGGGGAATCATCATGAGGATTAGATGAGGGTTGTGGTGATCCTT
CTGCTTCTTGAGGCGCCCCAGATCTCCACGGCCATGGTCATCCTCAT
TGTCCACGCCTTTGAATTTGATTTCCATCACCTCGTGAATGTTTTCC
AGGATATCTCCATTGGGCTGAAAGGTGTGACATGGACAGTGAATGCT
GATTTCTAGACCTAAGTTGGACTCTCTTCTCAACAGCCACTCACGCA
CAGTGTCAGTGACATCAAAGGACAGCCACTCGGCAGTGCCCCGTGTG
GGCAGATTCTTGCCACCGATATAGCGCTGTTTGGCAATGTGCTCATC
TGGCCGAAGGATCTGGAAGAGCTCGATCCTCTGCTCATTCCGCTTAG
AGCTGGGGTTGGGCACCCGCAAGACCCGGAATTCTGCTCGGAATAGG
TTGGTTCTACTCCACTGAGGACACATTGAAGCGGAAAACCTTGGAGG
TAATTCCTTTAGGGCAGACAGCCAGTTCGTTGTGCTCCGCCAGCCCC
TGGATCATGTCGAATTTATGATTTCTTTGGCATAGTATTCCGACTC
GGTGTTTTCCTGGGTGCAGCCTTCCTCCCTCTCCCCATGCATCTCCT
CCAGCAGCTCCCGGGTGCTGTTGTAAAGGGCCAGGACCTGATAGGGG
ACGTGGGTCATCACCGTTGGCTCAGGGGGCTGGTGAGCCTGAGCTT
GCTCAAGATCTGTCCCCTAATGGCTTCCACCCTCTTCTTCTTGATGT
GGCCGAAGTCCAAGGTGGTGCAAGTGGACAGAGAGAGGCTGACCGTG
GCAAAGTTCAGCAGGGCCAGGACCACCAGAGCCCTTTGCAAGTGCAT
CTTCATGTGTGAGCTGGGAAGAGAGGCCAGGGGGACGGCAAGGCCTG
GAGAGGAAGAGACCCCAGCAGACGTGCAGAAGGGAGGGAGGAAAACCA
GGCGGCCTCCCCAGATCCCAAAGACTGAGGCTTGGCAAGAAGGTGCA
TGAACTCACTGCACTGCGAGAGCTTCAGGACTTCCAGGAAGCGCTGG
CAACCCTGAGGACGAAGAAGCGGACTGTGTGCCTTGTAGCGCTGGGA
TTCTTGTCCATGTGTCTAAACAGGTTTTGCTGG Antisense of m-RNA of human Interleukin 10
(IL-10)
                                    (SEQ ID NO: 150)
TCACCCTATGGAAACAGCTTAAAAACAGGTGAAAATAATAAATATTG
AAAAAAATTATAATATTGGGCTTCTTTCTAAATCGTTCACAGAGAAG
CTCAGTAAATAAATAGAAATGGGGGTTGAGGTATCAGAGGTAATAAA
TATTCTATAAGAGAGGTACAATAAGGTTTCTCAAGGGGCTGGGTCAG
CTATCCCAGAGCCCCACAGATCCGATTTTGGAGACCTCTAATTTATGTC
CTAGAGTCTATAGAGTCGCCACCCTGATGTCTCAGTTTCGTATCTTC
ATTGTCATGTAGGCTTCTATGTAGTTGATGAAGATGTCAAACTCACT
CATGGCTTTGTAGATGCCTTTCTCTTGGAGCTTATTAAAGGCATTCT
TCACCTGCTCCACGGCCTTGCTCTTGTTTTCAAGGAGAAGAATCAA
TGACAGCGCCGTAGCCTCAGCCTGAGGGTCTTCAGGTTCTCCCCCAG
GGAGTTCACATGCGCCTTGATGTCTGGGTCTTGGTTCTCAGCTTGGG
GCATCACCTCCTCCAGGTAAAACTGGATCATCTCAGACAAGGCTTGG
CAACCCAGGTAACCCTTAAAGTCCTCCAGCAAGGACTCCTTTAACAA
CAAGTTGTCCAGCTGATCCTTCATTTGAAAGAAAGTCTTCACTCTGC
```

-continued
```
TGAAGGCATCTCGGAGATCTCGAAGCATGTTAGGCAGGTTGCCTGGG
AAGTGGGTGCAGCTGTTCTCAGACTGGGTGCCCTGGCCTGGGCTGGC
CCTCACCCCAGTCAGGAGGACCAGGCAACAGAGCAGTGCTGAGCTGT
GCATGCCTTCTTTTGCAAGTCTGTCTTGTGGTTTGGTTTTGCAAGAG
CAACCCCCTGATGTGTAGACCTTCACCTCTCTGTCCCCCTTTTATAT
TGTAAGCTCAGGGAGGCCTCTTCATTCATTAAAAAGCCACAATCAAG
GTTTCCCGGCACAGGATTTTTTCTGCTTAGAGCTCCTCCTTCTCTAA
CCTCTCTAATAAACTTAGTTTTCAATTTTTGCATCGTAAGCAAAAAT
GATTGGTTGAACATGAACTTCTGCATTACAGCTATTTTTAGGATGGG
CTACCTCTCTTAGAATAATTTTTTAGCTTCTCAATTAAAAAAAGTTG
ATTTCCTGGGGAGAACAGCTGTTCTGTCCGCAGAGGCCCTCAGCTGT
GGGTTCTCATTCGCGTGTTCCTAGGTCACAGTGACGTGGACAAATTG
CCCATTCCAGAATACAATGGGATTGAGAAATAATTGG
```

Antisense m-RNA of human Prostaglandin E2
Synthase
(SEQ ID NO: 151)
```
ttttttttttttttttttttttttttttttttttttttttttttttt
ttttttttttCCATGAGATGCCTGCCATGACAGGCGCCACAAACCTT
TCCTTTATTGCAAACATGTCCCAGTCCCGGGAGGCTTGGGAAGAGTG
GGAACCAGGGGAACCCAGGGATGGGATTCCACTGAAAACAAACCGTC
CTGCTGTCCTGTCGAGGGCCCCCACCCACAGGATGTAGCCATGGGAC
AGCCACTGAGGGTCCAGGAAGAGGGGCGGCAGAGCAGGGAGGCAGGG
ACAGGGAGGGGTCGCCCCAGGGCAGTGGCAGGGCTGGAACTCGTCCC
TAACATCCCTGAGCCCCAGCAGGTGCCCTGTGTTAGAAGCGAGAGGG
CTGGTGGGGGTGCGTGGACAAGGGGCAGAATGATCCTGCCCCCAACC
AGTATCGCCAGGCGCTGGCCCAGTGGCCCCAGGCCCTGGCAGCTGGC
GTCTTCCGCTGCCTTCCCTCTGCTCTGCGCGGGACATTCAGTGCGC
TGGGGAGGCCTCGGTGATGGCCCTCTCCACCCGCAGGTACCAGGGCT
GGATGTGCGTGTGCTGCATCAGGTCATCGAATGCATCCAGCCCCTCC
ATCACACGCAGCACGCCATACACCGCCAAATCAGCGAGATTCGGCTT
CTGGCCCCCCATGAAGGGCCGGTCCTTGCCCACAGCAGCCACCCACT
TGTCAGCAGCCTCATAGAGGTCCTCGCGCACGTTGTCCTGGAGGCGG
TGCCTGCTCTTGAGTCGCTTGCTGATGAGGTACATGGCCGCTGCACC
CATGTACTTGGCCACGGCACCCTCCACGGCTCCGAACCTTGCCCTCGC
GGACAATGTAGTCAAAGGACGCCAGAGCCTCGGTGGGCGTGCGGTAC
ACATTGGGGGAGATCAGGTGCACCAGCCAGTCGTCCGCCCACTGCCG
CCACTTCATCTCCTCCGTCCTGGCCTCCTTTCCCACCATACACTTGCT
GGGCCTCCTTCTCGTTGAGCATGAGCCAGTACTTATTGCCGAACTCG
GTCACCTCCTTGCCCTGCTCGTTCACAGCCTTCATGGCTGGGTAGTA
GGTGATGATCTCTTCCAGGGGCTGCCCCGACACCAGGTAGGTCTTGA
GGGCGCTGATGATGACAGAGGAGTCATTTAGTTGTTGCGAGCTTTCT
CCTTCCTGGGCCACCAGGATGGGCACCTTTCTGTAGGAGGAGAACTT
GATCTCAGCCCTCGCGCACAGGGTTCACCTCCACCACCTGGTAGGGCA
GGGCATGGAAGTCGAGGAAGGCTCGGACCTTGCTGCAGAAGGGACAC
GTCTTGTACTGGTACAGGGTCAGCTGCAGGCGGCTGGACAGGGAGAG
CTGCGCGGCTGAGCGCTCTGCGTGGAGGTCCTGGGCGCGCAGGTGCC
ACCGCGCCGTGTGGTACAGCCCCAGGGCTCCCCCCAGGGCCAGCGCC
GCAGCTCCCAGCAGCCGCGGGCTCCCCTTACGAGCTGCAGCCACGGG
GCTCGGGCCGCCCGCCGCCCCCGCGAAGCCAGCCCGGCTCTGCGTGG
GTAGCAGCGGCTGGGGGCGGCCTCCCAGCCTCCAGGCCAAGGCGCAC
CCACCAGGCCACAGCGCCGCACCACCCGCGCAGCCGGGTCCATGTT
CGCTCCGCCGGCGCGCGGGCGGGCGCGCGAAACGAAGACGCCGAGG
CACGCGCGGCGTTTAAAGGGCCAGGACTCTGGCGCCCCGCGGGTTGG
CCGGGGTGAGGGCGACGCTAAGGGAACCCTCAGCGCTCTCGGGACTG
GGCGTGTGCCCGGCGCCCAAGTTCGAAACGCCCGCC
```

Antisense m-RNA of human VEGF
(SEQ ID NO: 152)
```
CAGTGTGCTGGCGGCCGCGGTGTGTCTACAGGAATCCCAGAAATAAA
ACTCTCTAATCTTCCGGGCTCGGTGATTTAGCAGCAAGAAAAATAAA
ATGGCGAATCCAATTCCAAGAGGGACCGTGCTGGGTCACCCGCCCGG
GAATGCTTCCGCCGGAGTCTCGCCCTCCGGACCCAAAGTGCTCTGCG
CAGAGTCTCCTCTTCCTTCATTTCAGGTTTCTGGATTAAGGACTGTT
CTGTCGATGGTGATGGTGTGGTGGCGGCAGCGTGGTTCTGTATCGA
TCGTTCTGTATCAGTCTTTCCTGGTGAGAGATCTGGTTCCCGAAACC
CTGAGGGAGGCTCCTTCCTCCTGCCCGGCTCACCGCCTCGGCTTGTC
ACATCTGCAAGTACGTTCGTTTAACTCAAGCTGCCTCGCCTTGCAAC
GCGAGTCTGTGTTTTGCAGGAACATTTACACGTCTGCGGATCTTGT
ACAAACAAATGCTTTCTCCGCTCTGAGCAAGGCCCACAGGGATTTTC
TTGTCTTGCTCTATCTTTCTTTGGTCTGCATTCACATTTGTTGTGCT
GTAGGAAGCTCATCTCTCCTATGTGCTGGCCTTGGTGAGGTTTGATC
CGCATAATCTGCATGGTGATGTTGGACTCCTCAGTGGGCACACACTC
CAGGCCCTCGTCATTGCAGCAGCCCCCGCATCGCATCAGGGGCACAC
AGGATGGCTTGAAGATGTACTCGATCTCATCAGGGTACTCCTGGAAG
ATGTCACCAGGGTCTCGATTGGATGGCAGTAGCTGCGCTGATAGAC
ATCCATGAACTTCACCACTTCGTGATGATTCTGCCCTCCTCCTTCTG
CCATGGGTGCAGCCTGGGACCACTTGGCATGGTGGAGGTAGAGCAGC
AAGGCGAGGCTCCAATGCACCCAAGACAGCAGAAAGTTCATGGTTTC
GGAGGCCCGACCGGGGCCGGGCCGGCTCGCGCCGGGGCGCCAGCACA
CTG
```

Example 8

TGF-Beta Inhibitors
Small Molecules Inhibiting TGF-Beta
SB-431542 TBRI kinase inhibitor from GlaxoSmithKline (Callahan et al. 2002, Laping et al. 2002, Inman et al. 2002)
NPC30345 TBRI kinase inhibitor from Scios, Inc. (Dumont & Arteaga 2003)
SD-093 TBR-I kinase inhibitor (Subramanian, G. et al. 2003)
LY364947 TBRI kinase inhibitor from Lilly Inc. (Sawyer et al. 2003).
Decorin a small chondroitin-dermatan sulfate proteoglycan that binds various forms of active TGF-3 (Border et al. 1992).
Proteins Inhibiting TGF-Beta
Endoglin a TGF-β binding 95 kDa glycoprotein (Gougos et al. 1992).
Antibodies Binding TGF-Beta
CAT-192 humanized TGF-betal mAB from Genzyme/CAT (Benigni et al. 2003).
CAT-152 humanized TGF-beta2 mAB from Genzyme/CAT (Siriwardena et al. 2002).
1D11 TGF-beta1, 2, 3 mAB from Genzyme/CAT (Ananth et al. 1999).
2G7 TGF-beta1, 2, 3 monoclonal IgG2 from Genentech., (Arteaga et al. 1993).
Antibodies Against TGF-beta 1, -2, or -3 from R&D see e.g. catalog 614 R&D systems, McKinley Place Nebr., Minneapolis, Minn. USA 55413 rabbit anti-TGF-beta2 LAP: (Schlotzer-Schrehardt, U. et al. 2001).
Soluble Receptors
sTβRII:Fc (RII/Fc hu IgG1 fusion protein) from Biogen (Muraoka et al. 2002, Rowland-Goldsmith et al. 2001)
sTβRII:Fc (Yang, Y. A. et al. 2002)
Betaglycan (recombinant soluble TβRIII) (Bandyopadhyay et al. 2002)

Example 9

Amino Acid Sequences of TGF-Beta 1, -2 and -3
RXXR: cleavage site of the mature (active) part (XX may be anything)
ASPC: the C of this motif is the C for the intermolecular cystine bridge that links the two monomers into a functional dimer
C C C: intramolecular cystein bridges (cystein knot motif) mature protein of TGF-beta 1, 2 and 3 contains 112 amino acids from the end of this listing TGF-beta 1
(SEQ ID NO: 153)
```
MPPSGLRLLLLLLPLLWLLVLTPGRPAAGLSTCKTIDMELVKRKRIE
AIRGQILSKLRLASPPSQGEVPPGPLPEAVLALYNSTRDRVAGESAE
PEPEPEADYYAKEVTRVLMVETHNEIYDKFKQSTHSIYMFFNTSELR
EAVPEPVLLSRAELRLLRLKLKVEQHVELYQKYSNNSWRYLSNRLLA
PSDSPEWLSFDVTGVVRQWLSRGGEIEGFRLSAHCSCDSRDNTLQVD
INGFTTGRRGDLATIHGMNRPFLLLMATPLERAQHLQSSRHRRALDT
NYCFSSTEKNCCVRQLYIDFRKDLGWKWIHEPKGYHANFCLGPCPYI
WSLDTQYSKVLALYNQHNPGASAAPCCVPQALEPLPIVYYVGRKPKV
EQLSNMIVRSCKCS
``` preferred amino acid sequences of TGF-beta1:
1) ALDTNYCFSSTEKNCCVRQL
(SEQ ID NO: 154)
2) YIDFRKDLGWKWIHEPKGYH
(SEQ ID NO: 155)
3) ANFCLGPCPYIWSLDTQYSK
(SEQ ID NO: 156)

-continued

4) VLALYNQHNPGASAAPCCVP
(SEQ ID NO: 157)
5) QALEPLPIVYYVGRKPKVEQ
(SEQ ID NO: 158)
6) LSNMIVRSCKCS
(SEQ ID NO: 159)
7) TEKNCCVRQLYIDFRKDLGW
(SEQ ID NO: 160)
8) KWIHEPKGYHANFCLGPCPY
(SEQ ID NO: 161)
9) WSLDTQYSKVLALYNQHNP
(SEQ ID NO: 162)
10) GASAAPCCVPQALEPLPIVY
(SEQ ID NO: 163)
11) YVGRKPKVEQLSNMIVRSCKCS
(SEQ ID NO: 164)
12) QYSKVLALYNQHNPGASAAPCCVPQALEPLPIVYYVGRKP
(SEQ ID NO: 165)
13) QYSKVLALYNQHNPGASAAPCCVPQALEPLPIVYYVGRKP
          I
    QYSKVLALYNQHNPGASAAPCCVPQALEPLPIVYYVGRKP
(SEQ ID NO: 166)
(dimer of the TGF-beta1 amino acid
sequence No. 12 coupled by an s-s bridge
at the cytosines of the AAPC motif)
14) ALDTNYCFSSTEKNCCVRQLYIDFRKDLGWKWIHEPKGYHANF
    CLGPCPYIWSLDTQYSKVLALYNQHNPGASAAPCCVPQALEPL
    PIVYYVGRKPKVEQLSNMIVRSCKCS
(SEQ ID NO: 167)
15) ALDTNYCFSSTEKNCCVRQLYIDFRKDLGW
(SEQ ID NO: 168)
16) KWIHEPKGYHANFCLGPCPYIWSLDTQYSK
(SEQ ID NO: 169)
17) VLALYNQHNPGASAAPCCVPQALEPLPIVY
(SEQ ID NO: 170)
18) YVGRKPKVEQLSNMIVRSCKCS
(SEQ ID NO: 171)
19) CVRQLYIDFRKDLGWKWIHEPKGYHANFCL
(SEQ ID NO: 172)
20) GPCPYIWSLDTQYSKVLALYNQHNPGASAA
(SEQ ID NO: 173)
21) PCCVPQALEPLPIVYYVGRKPKVEQLSNMI
(SEQ ID NO: 174)

TGF-beta 2
                                        (SEQ ID NO: 175)
MHYCVLSAFLILHLVIVALSLSTCSTLDMDQFMRKRIEAIRGQILSK
LKLTSPPEDYPEPEEVPPEVISIYNSTRDLLQEKASRRAAACERERS
DEEYYAKEVYKIDMPPFFPSENAIPPTFYRPYFRIVRFDVSAMEKNA
SNLVKAEFRVFRLQNPKARVPEQRIELYQILKSKDLTSPTQRYIDSK
VVKTRAEGEWLSFDVTDAVHEWLHHKDRNLGFKISLHCPCCTFVPSN
NYIIPNKSEELEARFAGIDGTSTYTSGDQKTIKSTRKKNSGKTPHLL
LMLLPSYRLESQQTNRRKALDAAYCFRNVQDNCCLRPLYIDFKRDL
GWKWIHEPKGYNANFCAGACPYLWSSDTQHSRVLSLYNTINPEASAS
PCCVSQDLEPLTILYYIGKTPKIEQLSNMIVKSCKCS Preferred amino acid sequences of TGF-beta2
 1) ALDAAYCFRNVQDNCCLRPL
    (SEQ ID NO: 176)
 2) YIDFKRDLGWKWIHEPKGYN
    (SEQ ID NO: 177)
 3) ANFCAGACPYLWSSDTQHSR
    (SEQ ID NO: 178)
 4) VLSLYNTINPEASASPCCVS
    (SEQ ID NO: 179)
 5) QDLEPLTILYYIGKTPKIEQ
    (SEQ ID NO: 180)
 6) LSNMIVKSCKCS
    (SEQ ID NO: 181)
 7) VQDNCCLRPLYIDFKRDLGW
    (SEQ ID NO: 182)
 8) KWIHEPKGYNANFCAGACPY
    (SEQ ID NO: 183)
 9) LWSSDTQHSRVLSLYNTINP
    (SEQ ID NO: 184)
10) EASASPCCVSQDLEPLTILY
    (SEQ ID NO: 185)
11) YIGKTPKIEQLSNMIVKSCKCS
    (SEQ ID NO: 186)
12) QHSRVLSLYNTINPEASASPCCVSQDLEPLTILYYIGKTPK
    (SEQ ID NO: 187)
13) QHSRVLSLYNTINPEASASPCCVSQDLEPLTILYYIGKTPK
    (SEQ ID NO: 188)
              I
    QHSRVLSLYNTINPEASASPCCVSQDLEPLTILYYIGKTPK
    (SEQ ID NO: 188)
    (dimer of the TGF-beta2 amino acid
    sequence No. 12 coupled by an s-s bridge
    at the cytosines of the ASPC motif)
14) ALDAAYCFRNVQDNCCLRPLYIDFKRDLGWKWIHEPKGYNANF
    CAGACPYLWSSDTQHSRVLSLYN
    TINPEASASPCCVSQDLEPLTILYYIGKTPKIEQLSNMIVKSC
    KCS
    (SEQ ID NO: 189)
15) ALDAAYCFRNVQDNCCLRPLYIDFKRDLGW
    (SEQ ID NO: 190)
16) KWIHEPKGYNANFCAGACPYLWSSDTQHSR
    (SEQ ID NO: 191)
17) VLSLYNTINPEASASPCCVSQDLEPLTILY
    (SEQ ID NO: 192)
18) YIGKTPKIEQLSNMIVKSCKCS
    (SEQ ID NO: 193)
19) CLRPLYIDFKRDLGWKWIHEPKGYNANFCA
    (SEQ ID NO: 194)
20) GACPYLWSSDTQHSRVLSLYNTINPEASAS
    (SEQ ID NO: 195)
21) PCCVSQDLEPLTILYYIGKTPKIEQLSNMI
    (SEQ ID NO: 196)

TGF-beta3
                                        (SEQ ID NO: 197)
MKMHLQRALVVLALLNFATVSLSLSTCTTLDFGHIKKKRVEAIRGQI
LSKLRLTSPPEPTVMTHVPYQVLALYNSTRELLEEMHGEREEGCTQE
NTESEYYAKEIHKFDMIQGLAEHNELAVCPKGITSKVFRFNVSSVEK
NRTNLFRAEFRVLRVPNPSSKRNEQRIELFQILRPDEHIAKQRYIGG
KNLPTRGTAEWLSFDVTDTVREWLLRRESNLGLEISIHCPCHTFQPN
GDILENIHEVMEIKFPKGVDNEDDHGRGDLGRLKKQKDHHNPHLILMM
IPPHRLDNPGQGGQRKKRALDAAYCFRNVQDNCCLRPLYIDFKRDLG
WKWIHEPKGYNANFCAGACPYLWSSDTQHSRVLSLYNTINPEASASP
CCVSQDLEPLTILYYIGKTPKIEQLSNMIVKSCKCS preferred amino acid sequences of TGF-beta3:
 1) ALDTNYCFRNLEENCCVRPL
    (SEQ ID NO: 198)
 2) YIDFRQDLGWKWVHEPKGYY
    (SEQ ID NO: 199)
 3) ANFCSGPCPYLRSADTTHST
    (SEQ ID NO: 200)
 4) VLGLYNTLNPEASASPCCVP
    (SEQ ID NO: 201)
 5) QDLEPLTILYYVGRTPKVEQ
    (SEQ ID NO: 202)
 6) LSNMVVKSCKCS
    (SEQ ID NO: 203)
 7  NLEENCCVRPLYIDFRQDLG
    (SEQ ID NO: 204)
 8  WKWVHEPKGYYANFCSGPCP
    (SEQ ID NO: 205)
 9) YLRSADTTHSTVLGLYNTLN
    (SEQ ID NO: 206)
10) PEASASPCCVPQDLEPLTIL
    (SEQ ID NO: 207)
11) YYVGRTPKVEQLSNMVVKSCKCS
    (SEQ ID NO: 208)
12) THSTVLGLYNTLNPEASASPCCVPQDLEPLTILYYVGRTPK
    (SEQ ID NO: 209)
13) THSTVLGLYNTLNPEASASPCCVPQDLEPLTILYYVGRTPK
    (SEQ ID NO: 210)
              I
    THSTVLGLYNTLNPEASASPCCVPQDLEPLTILYYVGRTPK
    (SEQ ID NO: 210)
    (dimer of the TGF-beta3 amino acid
    sequence No.12 coupled by an s-s bridge at
    the cytosines of the ASPC motif)
14) ALDAAYCFRNVQDNCCLRPLYIDFKRDLGWKWIHEPKGYNANF
    CAGACPYLWSSDTQHSRVLSLYNTINPEASASPCCVSQDLEPL
    TILYYIGKTPKIEQLSNMIVKSCKCS
    (SEQ ID NO: 211)
15) ALDAAYCFRNVQDNCCLRPLYIDFKRDLGW
    (SEQ ID NO: 212)
16) KWIHEPKGYNANFCAGACPYLWSSDTQHSR
    (SEQ ID NO: 213)

17) VLSLYNTINPEASASPCCVSQDLEPLTILY
    (SEQ ID NO: 214)
18) YIGKTPKIEQLSNMIVKSCKCS
    (SEQ ID NO: 215)
19) CLRPLYIDFKRDLGWKWIHEPKGYNANFCA
    (SEQ ID NO: 216)
20) GACPYLWSSDTQHSRVLSLYNTINPEASAS
    (SEQ ID NO: 217)
21) PCCVSQDLEPLTILYYIGKTPKIEQLSNMI
    (SEQ ID NO: 218)

Sequenzen:

|  | Seq. Id. No. | Sequences | Length No. | int. Bez. int. |
|---|---|---|---|---|
| TGF-beta 1 | 1 | CGATAGTCTTGCAG | 14 | 1 |
|  | 2 | GTCGATAGTCTTGC | 14 | 2 |
|  | 3 | CTTGGACAGGATCT | 14 | 3 |
|  | 4 | CCAGGAATTGTTGC | 14 | 4 |
|  | 5 | CCTCAATTTCCCCT | 14 | 5 |
|  | 6 | GATGTCCACTTGCA | 14 | 6 |
|  | 7 | CTCCAAATGTAGGG | 14 | 7 |
|  | 8 | ACCTTGCTGTACTG | 14 | 8 |
|  | 9 | GTAGTACACGATGG | 14 | 9 |
|  | 10 | CACGTAGTACACGA | 14 | 10 |
|  | 11 | CATGTTGGACAGCT | 14 | 11 |
|  | 12 | GCACGATCATGTTG | 14 | 12 |
|  | 13 | TGTACTCTGCTTGAAC | 16 | 13 |
|  | 14 | CTGATGTGTTGAAGAACA | 18 | 14 |
|  | 15 | CTCTGATGTGTTGAAG | 16 | 15 |
|  | 16 | GGAAGTCAATGTACAG | 16 | 16 |
|  | 17 | CATGTCGATAGTCTTGCA | 18 | 17 |
|  | 18 | AGCTGAAGCAATAGTTGG | 18 | 18 |
|  | 19 | GTCATAGATTTCGTTGTG | 18 | 19 |
|  | 20 | CTCCACTTTTAACTTGA | 18 | 20 |
|  | 21 | TGCTGTATTTCTGGTACA | 18 | 21 |
| TGF-beta 2 | 22 | CACACAGTAGTGCA | 14 | 1 |
|  | 23 | GCACACAGTAGTGC | 14 | 2 |
|  | 24 | GCTTGCTCAGGATCTGC | 17 | 3 |
|  | 25 | TACTCTTCGTCGCT | 14 | 4 |
|  | 26 | CTTGGCGTAGTACT | 14 | 5 |
|  | 27 | GTAAACCTCCTTGG | 14 | 6 |
|  | 28 | GTCTATTTTGTAAACCTCC | 19 | 7 |
|  | 29 | GCATGTCTATTTTGTAAACC | 20 | 8 |
|  | 30 | CGGCATGTCTATTTTGTA | 18 | 9 |
|  | 31 | GGCATCAAGGTACC | 14 | 10 |
|  | 32 | CTGTAGAAAGTGGG | 14 | 11 |
|  | 33 | ACAATTCTGAAGTAGGGT | 18 | 12 |
|  | 34 | TCACCAAATTGGAAGCAT | 18 | 13 |

-continued

|  | Seq. Id. No. | Sequences | Length | No. int. | Bez. int. |
|---|---|---|---|---|---|
|  | 35 | GCTTTCACCAAATTGGAAGC | 20 | 14 |  |
|  | 36 | CTGGCTTTTGGGTT | 14 | 15 |  |
|  | 37 | TCTGATATAGCTCAATCC | 18 | 16 |  |
|  | 38 | TCCTAGTGGACTTTATAG | 18 | 17 |  |
|  | 39 | TTTTTCCTAGTGGACT | 16 | 18 |  |
|  | 40 | CAATTATCCTGCACATTTC | 19 | 19 |  |
|  | 41 | GCAATTATCCTGCACA | 16 | 20 |  |
|  | 42 | GCAGCAATTATCCTGC | 16 | 21 |  |
|  | 43 | TGGCATTGTACCCT | 14 | 22 |  |
|  | 44 | TGTGCTGAGTGTCT | 14 | 23 |  |
|  | 45 | CCTGCTGTGCTGAGTG | 16 | 24 |  |
|  | 46 | CTTGGGTGTTTTGC | 14 | 25 |  |
|  | 47 | TTTAGCTGCATTTGCAAG | 18 | 26 |  |
|  | 48 | GCCACTTTTCCAAG | 14 | 27 |  |
| TGF-beta 3 | 49 | TCGAGCTTCCCCCA | 14 | 107 | TGF-β3-98-1 |
|  | 50 | CCCCGAGCCCAAGG | 14 | 108 | TGF-β3-98-2 |
|  | 51 | CCCGACGAGCCGG | 13 | 109 | TGF-β3-98-3 |
|  | 52 | ACGCACCAAGGCGA | 14 | 110 | TGF-β3-98-4 |
|  | 53 | CGGGTTGTCGAGCCC | 15 | 111 | TGF-β3-98-5 |
|  | 54 | CGGCAGTGCCCCG | 13 | 112 | TGF-β3-98-6 |
|  | 55 | CGCAATTCTGCTCG | 14 | 113 | TGF-β3-98-7 |
|  | 56 | TTCGTTGTGCTCCC | 14 | 114 | TGF-β3-98-8 |
|  | 57 | ATTCCGACTCGGTG | 14 | 115 | TGF-β3-98-9 |
|  | 58 | ACGTGCGTCATCACCGT | 17 | 116 | TGF-β3-98-10 |
|  | 59 | CCAAGAAGCC | 10 | 117 | TGF-β3-98-11 |
|  | 60 | CCTAATGCCTTCCA | 14 | 118 | TGF-β3-312 |
|  | 61 | TCAGCAGGGCCAGG | 14 | 187 | GF-β-3rwk-1 |
|  | 62 | GCAAAGTTCAGCAGGGC | 17 | 188 | GF-β-3rwk-2 |
|  | 63 | GGCAAAGTTCAGCAGG | 16 | 189 | GF-β-3rwk-3 |
|  | 64 | GTGGCAAAGTTCAGCAGG | 18 | 190 | GF-β-3rwk-4 |
|  | 65 | GTGGCAAAGTTCAG | 14 | 191 | GF-β-3rwk-5 |
|  | 66 | GACCGTGGCAAAGTTCAG | 18 | 192 | GF-β-3rwk-6 |
|  | 67 | AGAGAGGCTGACCGT | 15 | 193 | GF-β-3rwk-7 |
|  | 68 | GAGAGAGAGAGGCTGAC | 17 | 194 | GF-β-3rwk-8 |
|  | 69 | ACAGAGAGAGGCTGA | 15 | 195 | GF-β-3rwk-9 |
|  | 70 | GTGGACAGAGAGAGG | 15 | 196 | GF-β-3rwk-10 |
|  | 71 | CAACTGGACAGAGAGAGG | 18 | 197 | GF-β-3rwk-11 |
|  | 72 | TCTTCTTGATGTGGCC | 16 | 198 | GF-β-3rwk-12 |
|  | 73 | CCCTCTTCTTCTTGATG | 17 | 199 | GF-β-3rwk-13 |

-continued

|     | Seq. Id. No. | Sequences | Length | No. int. | Bez. int. |
|-----|---|---|---|---|---|
|     | 74 | CACCCTCTTCTTCT | 14 | 200 | GF-β-3rwk-14 |
|     | 75 | ATGGATTTCTTTGGCAT | 17 | 201 | GF-β-3rwk-15 |
|     | 76 | GGATTTCTTTGGC | 13 | 202 | GF-β-3rwk-16 |
|     | 77 | AAGTTGGACTCTCTTCTC | 18 | 203. | GF-β-3rwk-17 |
|     | 78 | TAAGTTGGACTCTCTTCT | 18 | 204. | GF-β-3rwk-18 |
| PGE | 79 | TAGGAGTGGTTGAGGC | 16 | 1539 | Prostaglan. Rec. EP3-1 |
|     | 80 | GTGTAGGAGTGGTTGAG | 17 | 1540 | Prostaglan. Rec. EP3-2 |
|     | 81 | CTGTGTAGGAGTGG | 14 | 1541 | Prostaglan. Rec. EP3-3 |
|     | 82 | CCCACATGCCTGTG | 14 | 1542 | Prostaglan. Rec. EP3-4 |
|     | 83 | CGATGAACAACGAG | 14 | 1543 | Prostaglan. Rec. EP3-5 |
|     | 84 | CTGGCGATGAACAACG | 16 | 1544 | Prostaglan. Rec. EP3-6 |
|     | 85 | CGCTGGCGATGAAC | 14 | 1545 | Prostaglan. Rec. EP3-7 |
|     | 86 | GAGCTAGTCCCGTTG | 15 | 1546 | Prostaglan. Rec. EP3-8 |
|     | 87 | GCGAAGAGCTAGTCC | 15 | 1547 | Prostaglan. Rec. EP3-9 |
|     | 88 | CCAGTTATGCGAAGAGC | 17 | 1548 | Prostaglan. Rec. EP3-10 |
|     | 89 | CCCCAGTTATGCGAAG | 16 | 1549 | Prostaglan. Rec. EP3-11 |
| VEGF | 90 | CGGCCGCGGTGTGT | 14 | 119 | VEGF-98-1 |
|     | 91 | CGGGAATGCTTCCGCCG | 17 | 120 | VEGF-98-2 |
|     | 92 | CGGCTCACCGCCTCGGC | 17 | 121 | VEGF-98-3 |
|     | 93 | CACGTCTGCGGATC | 14 | 122 | VEGF-93-4 |
|     | 94 | CCCCGCATCGCATCAGGG | 18 | 123 | VEGF-98-5 |
|     | 95 | CGCCTTGCAACGCG | 14 | 124 | VEGF-98-6 |
|     | 96 | CCGACCGGGGCCGG | 14 | 125 | VEGF-98-7 |
|     | 97 | GTTCATGGTTTCGG | 14 | 126 | VEGF-49 |
|     | 98 | GCAGAAAGTTCATGG | 15 | 127 | VEGF-55 |
|     | 99 | GCTGATAGACATCC | 14 | 128 | VEGF-188 |
|     | 100 | GCGCTGATAGACAT | 14 | 129 | VEGF-190 |
|     | 101 | GTAGCTGCGCTGATAG | 16 | 130 | VEGF-194 |
|     | 102 | CTCGATCTCATCAG | 14 | 131 | VEGF-253 |
|     | 103 | ATGTACTCGATCTCATC | 17 | 132 | VEGF-255 |
|     | 104 | GAAGATGTGACTCGATC | 16 | 133 | VEGF-260 |
|     | 105 | CTTGAAGATGTACTCG | 16 | 134 | VEGF-263 |
|     | 106 | GCATCGCATCAGGG | 14 | 135 | VEGF-292 |
|     | 107 | CCGCATCGCATCAG | 14 | 136 | VEGF-294 |

-continued

| | Seq. Id. No. | Sequences | Length | No. int. | Bez. int. |
|---|---|---|---|---|---|
| | 108 | CATTTGTTGTGCTGTAGG | 18 | 137 | VEGF-422 |
| | 109 | GGTCTGCATTCACATTTG | 18 | 138 | VEGF-434 |
| | 110 | CTTTGGTCTGCATTC | 15 | 139 | VEGF-441 |
| | 111 | CTTTCTTTGGTCTGC | 15 | 140 | VEGF-445 |
| | 112 | GCTCTATCTTTCTTTGG | 17 | 141 | VEGF-450 |
| | 113 | GTCTTGCTCTATCTTTC | 17 | 142 | VEGF-455 |
| | 114 | CTTGTCTTGCTCTATC | 16 | 143 | VEGF-459 |
| | 115 | CATCTGCAAGTACGTTCG | 18 | 144 | VEGF-596 |
| | 116 | CACATCTGCAAGTACGTT | 18 | 145 | VEGF-598 |
| | 117 | GTCACATCTGCAAGTACG | 18 | 146 | VEGF-600 |
| | 118 | CATCTGCAAGTACG | 14 | 147 | VEGF-600-2 |
| | 119 | CACATCTGCAAGTAC | 15 | 148 | VEGF-601 |
| | 120 | GTCACATCTGCAAG | 14 | 149 | VEGF-604 |
| | 121 | CTTGTCACATCTGC | 14 | 150 | VEGF-607 |
| | 122 | GGCTTGTCACATCTGC | 16 | 151 | VEGF-607-2 |
| | 123 | CTCGGCTTGTCACATC | 16 | 152 | VEGF-610 |
| | 124 | CTCCTTCCTCCTGC | 14 | 153 | VEGF-638 |
| | 125 | GCTTGAAGATGTACCTCG | 16 | 154 | VEGF-766 |
| | 126 | CGTTGCTCTCCGACG | 15 | 155 | VEGF-r-1062 |
| IL-10 | 127 | GTAAAACTGGATCATCTC | 16 | 156 | U16720 |
| | 128 | CTTCTTTTCAAGTCTGT | 18 | | |
| | 129 | TGAGCTGTGCATGCCTTC | 18 | | |
| | 130 | AGTCAGGAGGACCAG | 15 | | |
| | 131 | TGGGTGCCCTGGCCT | 15 | | |
| | 132 | CATGTTAGGCAGGTT | 15 | | |
| | 133 | AGGCATCTCGGAGATCT | 17 | | |
| | 134 | AAAGTCTTCACTCTGC | 16 | | |
| | 135 | AACAAGTTGTCCAGCTG | 17 | | |
| | 136 | CATCACCTCCTCCAG | 15 | | |
| | 137 | GGGTCTTCAGGTTCTCCC | 18 | | |
| | 138 | CACGGCCTTGCTCTTGTT | 18 | | |
| | 139 | TTATTAAAGGCATTCTTC | 18 | | |
| | 140 | AAGATGTCAAACTCACTC | 18 | | |
| | 141 | GTAGTTGATGAAGATGTC | 18 | | |
| | 142 | GATTTTGGAGACCTCT | 16 | | |
| | 143 | TCAGCTATCCCAGAGC | 16 | | |
| | 144 | GGCTGGGTCAGCTAT | 15 | | |

| Seq. Id. No. | Sequences | Length No. int.Bez. int. |
|---|---|---|
| 145 | AAATCGTTCACAGAGAAG | 18 |
| 146 | TCTTTCTAAATCGTTCAC | 18 |

The invention claimed is:

1. A pharmaceutical composition comprising a chemotherapeutic agent selected from the group consisting of gemcitabine, temozolomide and dacarbazine, and a TGF-beta antisense oligonucleotide of SEQ ID NO:30, wherein the antisense oligonucleotide reduces the $IC_{50}$ of the cytotoxicity of the chemotherapeutic agent.

2. The pharmaceutical composition according to claim 1, wherein the TGF-beta antisense oligonucleotide reduces the $IC_{50}$ of the chemotherapeutic agent by 5%.

3. The pharmaceutical composition according to claim 1, further comprising a pharmaceutically acceptable carrier, filler, lubricant, diluent, excipient, disintegrate, and/or adjuvant.

4. A method to treat a neoplasm which method comprises administering to a subject in need of such treatment an effective amount of the pharmaceutical composition according to claim 1.

5. The method of claim 4, wherein the neoplastic disease is selected from the group consisting of pancreatic cancer, melanoma, brain tumor, bladder cancer, renal carcinoma, lung cancer, breast cancer, ovary cancer, prostate cancer, colorectal cancer, gastric cancer, endometrial cancer, osteosarcoma, myosarcoma, blood born tumors, leukemias, tumor metastasis, hemangiomas, acoustic neuromas, neurofibromas, trachomas, pyogenic, granulomas, psoriasis, astracytoma, acoustic neuroma, blastoma, Ewing's tumor, craniopharyngioma, ependymoma, medulloblastoma, glioma, hemangioblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, cystadenocarcinoma, embrional carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma, skin cancer, small-cell bronchogenic/lung carcinoma, squamous cell carcinoma, sebaceous gland carcinoma, testicular carcinoma, and uterine cancer.

6. The method of claim 5, wherein the brain tumor is a glioma, an astrocytoma, an oligodendroglioma, an anaplastic oligoastrozytoma, a glioblastoma, a brain metastasis, a myeloma, or a plasmocytoma.

7. The method of claim 4, wherein the pharmaceutical composition is administered orally, intravenously, intracranially, intraperitoneally, intravesically, parenterally, topically, transdermally, subconjunctivally, or sublingually.

8. A method to treat a neoplasm which method comprises administering to a subject in need of such treatment an effective amount of a chemotherapeutic agent selected from the group consisting of gemcitabine, temozolomide and dacarbazine and a TGFβ antisense oligonucleotide of SEQ ID NO:30, wherein the antisense oligonucleotide reduces the $IC_{50}$ of the cytotoxicity of the chemotherapeutic agent wherein the chemotherapeutic agent and the antisense oligonucleotide are administered at the same time, partially timely overlapping, or timely distinct.

* * * * *

SEQUENCE LISTING

<160> NUMBER OF SEQ ID NOS: 218

<210> SEQ ID NO 1
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 1
cgatagtctt gcag                                                       14

<210> SEQ ID NO 2
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 2
gtcgatagtc ttgc                                                       14

<210> SEQ ID NO 3
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 3
cttggacagg atct                                                       14

<210> SEQ ID NO 4
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 4
ccaggaattg ttgc                                                       14

<210> SEQ ID NO 5
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 5
cctcaatttc ccct                                                       14

```
<210> SEQ ID NO 6
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 6
gatgtccact tgca                                                        14

<210> SEQ ID NO 7
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 7
ctccaaatgt aggg                                                        14

<210> SEQ ID NO 8
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 8
accttgctgt actg                                                        14

<210> SEQ ID NO 9
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 9
gtagtacacg atgg                                                        14

<210> SEQ ID NO 10
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 10
cacgtagtac acga                                                        14

<210> SEQ ID NO 11
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 11
catgttggac agct                                                        14
```

```
<210> SEQ ID NO 12
<211> LENGTH: 14
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 12
gcacgatcat gttg                                                        14

<210> SEQ ID NO 13
<211> LENGTH: 16
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 13
tgtactctgc ttgaac                                                      16

<210> SEQ ID NO 14
<211> LENGTH: 18
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 14
ctgatgtgtt gaagaaca                                                    18

<210> SEQ ID NO 15
<211> LENGTH: 16
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 15
ctctgatgtg ttgaag                                                      16

<210> SEQ ID NO 16
<211> LENGTH: 16
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 16
ggaagtcaat gtacag                                                      16

<210> SEQ ID NO 17
<211> LENGTH: 18
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 17
catgtcgata gtcttgca                                                    18

<210> SEQ ID NO 18
<211> LENGTH: 18
```

```
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 18
agctgaagca atagttgg                                                 18

<210> SEQ ID NO 19
<211> LENGTH: 18
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 19
gtcatagatt tcgttgtg                                                 18

<210> SEQ ID NO 20
<211> LENGTH: 18
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 20
ctccactttt aacttgag                                                 18

<210> SEQ ID NO 21
<211> LENGTH: 18
<212> TYPE: DNA
<213> ORGANISM: Artificial Sequence
<220> FEATURE:
<223> OTHER INFORMATION: Synthetically constructed human TGF-beta
      1 antisense oligonucleotide

<400> SEQUENCE: 21
tgctgtattt ctggtaca                                                 18

<210> SEQ ID NO 22
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 22
cacacagtag tgca                                                     14

<210> SEQ ID NO 23
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 23
gcacacagta gtgc                                                     14

<210> SEQ ID NO 24
<211> LENGTH: 17
<212> TYPE: DNA
<213> ORGANISM: Artificial Sequence
```

```
<220> FEATURE:
<223> OTHER INFORMATION: Synthetically constructed human TGF-beta
      2 antisense oligonucleotide

<400> SEQUENCE: 24
gcttgctcag gatctgc                                                  17

<210> SEQ ID NO 25
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 25
tactcttcgt cgct                                                     14

<210> SEQ ID NO 26
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 26
cttggcgtag tact                                                     14

<210> SEQ ID NO 27
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 27
gtaaacctcc ttgg                                                     14

<210> SEQ ID NO 28
<211> LENGTH: 19
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 28
gtctattttg taaacctcc                                                19

<210> SEQ ID NO 29
<211> LENGTH: 20
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 29
gcatgtctat tttgtaaacc                                               20

<210> SEQ ID NO 30
<211> LENGTH: 18
<212> TYPE: DNA
<213> ORGANISM: Artificial Sequence
<220> FEATURE:
<223> OTHER INFORMATION: Synthetically constructed human TGF-beta
```

-continued 2 antisense oligonucleotide

<400> SEQUENCE: 30
cggcatgtct attttgta                                                 18

<210> SEQ ID NO 31
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 31
ggcatcaagg tacc                                                     14

<210> SEQ ID NO 32
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 32
ctgtagaaag tggg                                                     14

<210> SEQ ID NO 33
<211> LENGTH: 18
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 33
acaattctga agtagggt                                                 18

<210> SEQ ID NO 34
<211> LENGTH: 18
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 34
tcaccaaatt ggaagcat                                                 18

<210> SEQ ID NO 35
<211> LENGTH: 20
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 35
gctttcacca aattggaagc                                               20

<210> SEQ ID NO 36
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide -continued

```
<400> SEQUENCE: 36
ctggcttttg ggtt                                                        14

<210> SEQ ID NO 37
<211> LENGTH: 18
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 37
tctgatatag ctcaatcc                                                    18

<210> SEQ ID NO 38
<211> LENGTH: 18
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 38
tcctagtgga ctttatag                                                    18

<210> SEQ ID NO 39
<211> LENGTH: 16
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 39
tttttcctag tggact                                                      16

<210> SEQ ID NO 40
<211> LENGTH: 19
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 40
caattatcct gcacatttc                                                   19

<210> SEQ ID NO 41
<211> LENGTH: 16
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 41
gcaattatcc tgcaca                                                      16

<210> SEQ ID NO 42
<211> LENGTH: 16
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 42
```
gcagcaatta tcctgc     16

<210> SEQ ID NO 43
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 43
tggcattgta ccct     14

<210> SEQ ID NO 44
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 44
tgtgctgagt gtct     14

<210> SEQ ID NO 45
<211> LENGTH: 16
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 45
cctgctgtgc tgagtg     16

<210> SEQ ID NO 46
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 46
cttgggtgtt ttgc     14

<210> SEQ ID NO 47
<211> LENGTH: 18
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 47
tttagctgca tttgcaag     18

<210> SEQ ID NO 48
<211> LENGTH: 14
<212> TYPE: DNA
<213> ORGANISM: Artificial Sequence
<220> FEATURE:
<223> OTHER INFORMATION: Synthetically constructed human TGF-beta
      2 antisense oligonucleotide

<400> SEQUENCE: 48 gccactttc caag     14

```
<210> SEQ ID NO 49
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 49
tcgagcttcc ccca                                                        14

<210> SEQ ID NO 50
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 50
ccccgagccc aagg                                                        14

<210> SEQ ID NO 51
<211> LENGTH: 13
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 51
cccgacgagc cgg                                                         13

<210> SEQ ID NO 52
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 52
acgcaccaag gcga                                                        14

<210> SEQ ID NO 53
<211> LENGTH: 15
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 53
cgggttgtcg agccc                                                       15

<210> SEQ ID NO 54
<211> LENGTH: 13
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 54
cggcagtgcc ccg                                                         13

<210> SEQ ID NO 55
```

```
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 55
cgcaattctg ctcg                                                     14

<210> SEQ ID NO 56
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 56
ttcgttgtgc tccc                                                     14

<210> SEQ ID NO 57
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 57
attccgactc ggtg                                                     14

<210> SEQ ID NO 58
<211> LENGTH: 17
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 58
acgtgcgtca tcaccgt                                                  17

<210> SEQ ID NO 59
<211> LENGTH: 10
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 59
ccaagaagcc                                                          10

<210> SEQ ID NO 60
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 60
cctaatgcct tcca                                                     14

<210> SEQ ID NO 61
<211> LENGTH: 14
<212> TYPE: DNA
```

<213> ORGANISM: Artificial Sequence
<220> FEATURE:
<223> OTHER INFORMATION: Synthetically constructed human TGF-beta
      3 antisense oligonucleotide

<400> SEQUENCE: 61
tcagcagggc cagg                                                         14

<210> SEQ ID NO 62
<211> LENGTH: 17
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 62
gcaaagttca gcagggc                                                      17

<210> SEQ ID NO 63
<211> LENGTH: 16
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 63
ggcaaagttc agcagg                                                       16

<210> SEQ ID NO 64
<211> LENGTH: 18
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 64
gtggcaaagt tcagcagg                                                     18

<210> SEQ ID NO 65
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 65
gtggcaaagt tcag                                                         14

<210> SEQ ID NO 66
<211> LENGTH: 18
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 66
gaccgtggca aagttcag                                                     18

<210> SEQ ID NO 67
<211> LENGTH: 15
<212> TYPE: DNA
<213> ORGANISM: Artificial Sequence
<220> FEATURE:

<223> OTHER INFORMATION: Synthetically constructed human TGF-beta
      3 antisense oligonucleotide

<400> SEQUENCE: 67
agagaggctg accgt                                                    15

<210> SEQ ID NO 68
<211> LENGTH: 17
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 68
gagagagaga ggctgac                                                  17

<210> SEQ ID NO 69
<211> LENGTH: 15
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 69
acagagagag gctga                                                    15

<210> SEQ ID NO 70
<211> LENGTH: 15
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 70
gtggacagag agagg                                                    15

<210> SEQ ID NO 71
<211> LENGTH: 18
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 71
caactggaca gagagagg                                                 18

<210> SEQ ID NO 72
<211> LENGTH: 16
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 72
tcttcttgat gtggcc                                                   16

<210> SEQ ID NO 73
<211> LENGTH: 17
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 73 cctcttctt cttgatg                                                    17

<210> SEQ ID NO 74
<211> LENGTH: 14
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 74
caccctcttc ttct                                                      14

<210> SEQ ID NO 75
<211> LENGTH: 17
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 75
atggatttct ttggcat                                                   17

<210> SEQ ID NO 76
<211> LENGTH: 13
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 76
ggatttcttt ggc                                                       13

<210> SEQ ID NO 77
<211> LENGTH: 18
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 77
aagttggact ctcttctc                                                  18

<210> SEQ ID NO 78
<211> LENGTH: 18
<212> TYPE: DNA
<213> ORGANISM: Artificial Sequence
<220> FEATURE:
<223> OTHER INFORMATION: Synthetically constructed human TGF-beta
      3 antisense oligonucleotide

<400> SEQUENCE: 78
taagttggac tctcttct                                                  18

<210> SEQ ID NO 79
<211> LENGTH: 16
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 79

```
taggagtggt tgaggc                                                       16

<210> SEQ ID NO 80
<211> LENGTH: 17
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 80
gtgtaggagt ggttgag                                                      17

<210> SEQ ID NO 81
<211> LENGTH: 14
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 81
ctgtgtagga gtgg                                                         14

<210> SEQ ID NO 82
<211> LENGTH: 14
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 82
cccacatgcc tgtg                                                         14

<210> SEQ ID NO 83
<211> LENGTH: 14
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 83
cgatgaacaa cgag                                                         14

<210> SEQ ID NO 84
<211> LENGTH: 16
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 84
ctggcgatga acaacg                                                       16

<210> SEQ ID NO 85
<211> LENGTH: 14
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 85
cgctggcgat gaac                                                         14
```

```
<210> SEQ ID NO 86
<211> LENGTH: 15
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 86
gagctagtcc cgttg                                                    15

<210> SEQ ID NO 87
<211> LENGTH: 15
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 87
gcgaagagct agtcc                                                    15

<210> SEQ ID NO 88
<211> LENGTH: 17
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 88
ccagttatgc gaagagc                                                  17

<210> SEQ ID NO 89
<211> LENGTH: 16
<212> TYPE: DNA
<213> ORGANISM: Artificial Sequence
<220> FEATURE:
<223> OTHER INFORMATION: Synthetically constructed human PGE
      antisense oligonucleotide

<400> SEQUENCE: 89
ccccagttat gcgaag                                                   16

<210> SEQ ID NO 90
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 90
cggccgcggt gtgt                                                     14

<210> SEQ ID NO 91
<211> LENGTH: 17
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 91
cgggaatgct tccgccg                                                  17
```

```
<210> SEQ ID NO 92
<211> LENGTH: 17
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 92
cggctcaccg cctcggc                                                     17

<210> SEQ ID NO 93
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 93
cacgtctgcg gatc                                                        14

<210> SEQ ID NO 94
<211> LENGTH: 18
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 94
ccccgcatcg catcaggg                                                    18

<210> SEQ ID NO 95
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 95
cgccttgcaa cgcg                                                        14

<210> SEQ ID NO 96
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 96
ccgaccgggg ccgg                                                        14

<210> SEQ ID NO 97
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 97
gttcatggtt tcgg                                                        14

<210> SEQ ID NO 98
<211> LENGTH: 15
```

```
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 98
gcagaaagtt catgg                                                     15

<210> SEQ ID NO 99
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 99
gctgatagac atcc                                                      14

<210> SEQ ID NO 100
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 100
gcgctgatag acat                                                      14

<210> SEQ ID NO 101
<211> LENGTH: 16
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 101
gtagctgcgc tgatag                                                    16

<210> SEQ ID NO 102
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 102
ctcgatctca tcag                                                      14

<210> SEQ ID NO 103
<211> LENGTH: 17
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 103
atgtactcga tctcatc                                                   17

<210> SEQ ID NO 104
<211> LENGTH: 16
<212> TYPE: DNA
<213> ORGANISM: Artificial Sequence
```

```
<220> FEATURE:
<223> OTHER INFORMATION: Synthetically constructed human VEGF
      antisense oligonucleotide

<400> SEQUENCE: 104
gaagatgtac tcgatc                                                         16

<210> SEQ ID NO 105
<211> LENGTH: 16
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 105
cttgaagatg tactcg                                                         16

<210> SEQ ID NO 106
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 106
gcatcgcatc aggg                                                           14

<210> SEQ ID NO 107
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 107
ccgcatcgca tcag                                                           14

<210> SEQ ID NO 108
<211> LENGTH: 18
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 108
catttgttgt gctgtagg                                                       18

<210> SEQ ID NO 109
<211> LENGTH: 18
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 109
ggtctgcatt cacatttg                                                       18

<210> SEQ ID NO 110
<211> LENGTH: 15
<212> TYPE: DNA
<213> ORGANISM: Artificial Sequence
<220> FEATURE:
<223> OTHER INFORMATION: Synthetically constructed human VEGF
``` antisense oligonucleotide

<400> SEQUENCE: 110
ctttggtctg cattc                                                   15

<210> SEQ ID NO 111
<211> LENGTH: 15
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 111
ctttctttgg tctgc                                                   15

<210> SEQ ID NO 112
<211> LENGTH: 17
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 112
gctctatctt tctttgg                                                 17

<210> SEQ ID NO 113
<211> LENGTH: 17
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 113
gtcttgctct atctttc                                                 17

<210> SEQ ID NO 114
<211> LENGTH: 16
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 114
cttgtcttgc tctatc                                                  16

<210> SEQ ID NO 115
<211> LENGTH: 18
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 115
catctgcaag tacgttcg                                                18

<210> SEQ ID NO 116
<211> LENGTH: 18
<212> TYPE: DNA
<213> ORGANISM: Artificial Sequence
<220> FEATURE:
<223> OTHER INFORMATION: Synthetically constructed human VEGF
      antisense oligonucleotide

```
<400> SEQUENCE: 116
cacatctgca agtacgtt                                            18

<210> SEQ ID NO 117
<211> LENGTH: 18
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 117
gtcacatctg caagtacg                                            18

<210> SEQ ID NO 118
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 118
catctgcaag tacg                                                14

<210> SEQ ID NO 119
<211> LENGTH: 15
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 119
cacatctgca agtac                                               15

<210> SEQ ID NO 120
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 120
gtcacatctg caag                                                14

<210> SEQ ID NO 121
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 121
cttgtcacat ctgc                                                14

<210> SEQ ID NO 122
<211> LENGTH: 16
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 122
```

-continued ggcttgtcac atctgc                                              16

<210> SEQ ID NO 123
<211> LENGTH: 16
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 123
ctcggcttgt cacatc                                              16

<210> SEQ ID NO 124
<211> LENGTH: 14
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 124
ctccttcctc ctgc                                                14

<210> SEQ ID NO 125
<211> LENGTH: 18
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 125
gcttgaagat gtacctcg                                            18

<210> SEQ ID NO 126
<211> LENGTH: 15
<212> TYPE: DNA
<213> ORGANISM: Artificial Sequence
<220> FEATURE:
<223> OTHER INFORMATION: Synthetically constructed human VEGF
      antisense oligonucleotide

<400> SEQUENCE: 126
cgttgctctc cgacg                                               15

<210> SEQ ID NO 127
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 127
gtaaaactgg atcatctc                                            18

<210> SEQ ID NO 128
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 128
cttcttttgc aagtctgt                                            18

```
<210> SEQ ID NO 129
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 129
tgagctgtgc atgccttc                                                18

<210> SEQ ID NO 130
<211> LENGTH: 15
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 130
agtcaggagg accag                                                   15

<210> SEQ ID NO 131
<211> LENGTH: 15
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 131
tgggtgccct ggcct                                                   15

<210> SEQ ID NO 132
<211> LENGTH: 15
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 132
catgttaggc aggtt                                                   15

<210> SEQ ID NO 133
<211> LENGTH: 17
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 133
aggcatctcg gagatct                                                 17

<210> SEQ ID NO 134
<211> LENGTH: 16
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 134
aaagtcttca ctctgc                                                  16

<210> SEQ ID NO 135
```

```
<211> LENGTH: 17
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 135
aacaagttgt ccagctg                                                    17

<210> SEQ ID NO 136
<211> LENGTH: 15
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 136
catcacctcc tccag                                                      15

<210> SEQ ID NO 137
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 137
gggtcttcag gttctccc                                                   18

<210> SEQ ID NO 138
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 138
cacggccttg ctcttgtt                                                   18

<210> SEQ ID NO 139
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 139
ttattaaagg cattcttc                                                   18

<210> SEQ ID NO 140
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 140
aagatgtcaa actcactc                                                   18

<210> SEQ ID NO 141
<211> LENGTH: 18
<212> TYPE: DNA
```

```
<213> ORGANISM: Artificial Sequence
<220> FEATURE:
<223> OTHER INFORMATION: Synthetically constructed human IL-10
      antisense oligonucleotide

<400> SEQUENCE: 141
gtagttgatg aagatgtc                                                 18

<210> SEQ ID NO 142
<211> LENGTH: 16
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 142
gattttggag acctct                                                   16

<210> SEQ ID NO 143
<211> LENGTH: 16
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 143
tcagctatcc cagagc                                                   16

<210> SEQ ID NO 144
<211> LENGTH: 15
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 144
ggctgggtca gctat                                                    15

<210> SEQ ID NO 145
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 145
aaatcgttca cagagaag                                                 18

<210> SEQ ID NO 146
<211> LENGTH: 18
<212> TYPE: DNA
<213> ORGANISM: Artificial Sequence
<220> FEATURE:
<223> OTHER INFORMATION: Synthetically constructed human IL-10
      antisense oligonucleotide

<400> SEQUENCE: 146
tctttctaaa tcgttcac                                                 18

<210> SEQ ID NO 147
<211> LENGTH: 2745
<212> TYPE: DNA
<213> ORGANISM: Artificial Sequence
<220> FEATURE:
```

<223> OTHER INFORMATION: Synthetically constructedantisense mRNA
of human TGF-beta 1

<400> SEQUENCE: 147

```
ctgcagcctt gacctcccag gatcaagtga tcctcccacc ttagcctcca gagtagctgg      60
gaccacaggt gtacattttt taaaagtgtt ttgtagagat agggtctcac tatgttaccc     120
aggctggtct caaatgcctg gattcaagta tcctcccatc tctgcctccc aaaagtgcta     180
ggattacagg cgtgagcacc ccgcctggcc tgaactacta tcttttattg tcttcttcac     240
tatcccccac taaagcaggt tcctggtggg caggaactcc tcccttaacc tctctgggct     300
tgtttcctca acctttaaaa tgggtgttat cagagtccct gccatctcag agtgttgcta     360
tggtgactga atgagttcat taatgtaagg cacttcaaca gtgcccaagg tgctcaataa     420
atagatctaa ctacagtagt gttccccact ggtcccctgt gccttgatgc cgggcaaagg     480
aatagtgcag acaggcagga ggaggcagag agggagagag agggagtggg agtgggggaa     540
cgtcagggat ggagacccca ggcaggcgcc caatgacaca gagatccgca gtcctctctc     600
catctttaat ggggcccag gtgggcttgg ggcacggtgt ccttaaatac agccccatg      660
ggcaaggcag cggggggcggg gcggggtggg gccgggcctg ccggggcggg gcggggcggg     720
gcgggacctc agctgcactt gcaggagcgc acgatcatgt tggacagctg ctccaccttg     780
ggcttgcggc ccacgtagta cacgatgggc agccggtcca gcgcctgcgg cacgcagcac     840
ggcgccgccg aggcgcccgg gttatgctgg ttgtacaggg ccaggaccctt gctgtactgc     900
gtgtccaggc tccaaatgta ggggcagggc ccgaggcaga agttggcatg gtagcccttg     960
ggctcgtgga tccacttcca gccgaggtcc ttgcggaagt caatgtacag ctgccgcacg    1020
cagcagttct tctccgtgga gctgaagcaa tagttggtgt ccaggctcg gcggtgccgg     1080
gagctttgca gatgctgggc cctctccagc ggggtggcca tgagaagcag gaaaggccgg    1140
ttcatgccat gaatggtggc caggtcacct cggcggccgg tagtgaaccc gttgatgtcc    1200
acttgcagtg tgttatccct gctgtcacag gagcagtggg cgctaaggcg aaagccctca    1260
atttcccctc cacggctcaa ccactgccgc acaactccgg tgacatcaaa agataaccac    1320
tctggcgagt cgctgggtgc cagcagccgg ttgctgaggt atcgccagga attgttgctg    1380
tatttctggt acagctccac gtgctgctcc acttttaact tgagcctcct cagcagacgc    1440
agctctgccc gggagagcaa cacgggttca ggtaccgctt ctcggagctc tgatgtgttg    1500
aagaacatat atatgctgtg tgtactctgc ttgaacttgt catagatttc gttgtgggtt    1560
tccaccatta gcacgcgggt gacctccttg gcgtagtagt cggcctcagg ctcgggctcc    1620
ggttctgcac tctccccggc cacccggtcg cgggtgctgt tgtacagggc gagcacggcc    1680
tcgggcagcg ggccgggcgg cacctccccc tggctcgggg ggctggcgag ccgcagcttg    1740
gacaggatct ggccgcggat ggcctcgatg cgcttccgct tcaccagctc catgtcgata    1800
gtcttgcagg tggatagtcc cgcggccggc gggccaggcg tcagcaccag tagccacagc    1860
agcggtagca gcagcggcag cagccgcagc ccggagggcg gcatggggga ggcggcgccc    1920
cccggcactg ccgagagcgc gaacagggct ggtgtggtgg ggaggccccg ccctgcagg     1980
ggctggggt ctcccggcaa aaggtaggag ggcctcgagg gaaagctgag gctcctcagg    2040
gagaagggcg cagtggtgga ggggaggctt ggaccggggg tgtctcagta tcccacggaa    2100
ataacctaga tgggcgcgat ctggtaccag aaggtgggtg gtcttgaata gggatctgt     2160
ggcaggtcgg agagagatcc gtctcctgga ggagaaaggg tctaggatgc gcggggctc     2220
aggagacagg ccggggatga aggcggcgtg caggggtgc gcccgaggtc tggggaaaag    2280
```

| | |
|---|---|
| tctttgcggg aggccgggtc ggcgactccc gagggctggt ccggaatggg ggcgcctgag | 2340 |
| ggacgccgtg taggggggcag ggagggagca agcgtccccg gcggcaaagg gaggcggtct | 2400 |
| ggggtcccca agtcctgcct cctcgcgggg cagcgtcgcg ccaagaggtc cccgcgcctc | 2460 |
| cggctcccag cggcaacgga aaagtctcaa aagtttttt cctcttctcc cgaccagctc | 2520 |
| gtccctcctc ccgctcctcc tccccctcct ccccgcagtg gcggggggcgg cggcggctcg | 2580 |
| tctcagactc tggggcctca ggctgctcct cggcgactcc ttcctccgct ccgggccgag | 2640 |
| gccggccccg cgggcggctc agagccgggg ggggtgcccc ggacggggcg tcccccctgc | 2700 |
| ccccggccgg ggccctcgct gtctggctgc tccgcggagg gaggt | 2745 |

<210> SEQ ID NO 148
<211> LENGTH: 1695
<212> TYPE: DNA
<213> ORGANISM: Artificial Sequence
<220> FEATURE:
<223> OTHER INFORMATION: Synthetically constructedantisense mRNA of human TGF-beta 2

<400> SEQUENCE: 148

| | |
|---|---|
| tttaaaaaaa tttgcttctt gtctctctca cttacaaagt aggtgaaatg tagaataagg | 60 |
| ccttcaactt ttttttgtgtc agatgccagt tttaacaaac agaacacaaa cttccaaagt | 120 |
| gtctgaacta gtaccgcctt ttcaaaaatt ttttaacact gatgaaccaa ggctctctta | 180 |
| tgttttcttg ttacaagcat catcgttgtc gtcgtcatca tcattatcat catcattgtc | 240 |
| attttggtct tgccactttt ccaagaattt tagctgcatt tgcaagactt tacaatcata | 300 |
| ttagaaagct gttcaatctt gggtgttttg ccaatgtagt agagaatggt tagaggttct | 360 |
| aaatcttggg acacgcagca aggagaagca gatgcttctg gatttatggt attatataag | 420 |
| ctcaggaccc tgctgtgctg agtgtctgaa ctccataaat acgggcatgc tccagcacag | 480 |
| aagttggcat tgtacccttt gggttcgtgt atccatttcc accctagatc cctcttgaaa | 540 |
| tcaatgtaaa gtggacgtag gcagcaatta tcctgcacat ttctaaagca ataggccgca | 600 |
| tccaaagcac gcttcttccg ccggttggtc tgttgtgact caagtctgta ggagggcaat | 660 |
| aacattagca ggagatgtgg ggtcttccca ctgttttttt tcctagtgga ctttatagtt | 720 |
| ttctgatcac cactggtata tgtggaggtg ccatcaaatac ctgcaaatct tgcttctagt | 780 |
| tcttcacttt tatttgggat gatgtaatta ttagatggta caaaagtgca gcagggacag | 840 |
| tgtaagctta ttttaaatcc caggttcctg tctttatggt gaagccattc atgaacagca | 900 |
| tcagttacat cgaaggagag ccattcgcct tctgctcttg ttttcacaac tttgctgtcg | 960 |
| atgtagcgct gggttggaga tgttaaatct ttggacttga gaatctgata tagctcaatc | 1020 |
| cgttgttcag gcactctggc ttttgggttc tgcaaacgaa agactctgaa ctctgctttc | 1080 |
| accaaattgg aagcattctt ctccattgct gagacgtcaa atcgaacaat tctgaagtag | 1140 |
| ggtctgtaga aagtgggcgg gatggcattt tcggagggga agaagggcgg catgtctatt | 1200 |
| ttgtaaacct cctggcgta gtactcttcg tcgctcctct cgcgctcgca ggcggccgcc | 1260 |
| ctccggctcg ccttctcctg gagcaagtcc ctggtgctgt tgtagatgga aatcacctcc | 1320 |
| ggggggactt cctcgggctc aggatagtct tctgggggac tggtgagctt cagcttgctc | 1380 |
| aggatctgcc cgcggatcgc ctcgatcctc ttgcgcatga actggtccat atcgagtgtg | 1440 |
| ctgcaggtag acaggctgag cgcgaccgtg accagatgca ggatcagaaa agcgctcagc | 1500 |
| acacagtagt gcatttttta aaaagtggaa aaaaaagtt gttttaaaa gtcagaataa | 1560 |

-continued

```
aaaaaaagaa atcaacaatt ctcaaagtat agatcaagga gagttgtttg gttttttgtt      1620
gttgttgttt gttttttgatg cgaaactttt gcaaacaatc tagtcaatgc ccaacagaaa      1680
aacgtatcct gcttg                                                        1695
```

<210> SEQ ID NO 149
<211> LENGTH: 2529
<212> TYPE: DNA
<213> ORGANISM: Artificial Sequence
<220> FEATURE:
<223> OTHER INFORMATION: Synthetically constructedantisense mRNA
      of human TGF-beta 3

<400> SEQUENCE: 149

```
caggatgccc caaaaatatt tatttataca aagattttga gagtaatatt catacttgtc        60 tttataccte agtctatgcg tctggggcca agtcactgtg tggcacatgt cgagcttccc       120
cgaatgcctc acatgttgtc gcacctgctt ccaggaacac caaatgaaca cagggtcttg       180
gaggggaagt gggggaagaa cccataatgc cccaaccctg catggaacca caatccagaa       240
atgtgcatcc tgacctggaa ggcgtctaac caagtgtcca aggggaaata tgatcgaggg       300
agaggtgaga ggagggaccc agaggcagac aggagagggt tgatttccac cctttcttct       360
gcgttcagca tatccaaaag gcccaataca gttgatgggc caggaactgc atgacctgga       420
ttttctccct gtagtgaccc acgatgttaa ttgatgtaga ggacagtttg caaaagtaat       480
agatttgccc ttaatcccag acagtatgag atacaattct gggactttgt cttcgtaacc       540 tgtcttaaa aaaaaaaaaa aatgcttgcc ttgtataaca taatccagat tccctagagc       600
agatgtggta cagcaatgag caaatccaac ctcagatctg aagtgtcttc cagtctggcc       660
ctgacccagc cattctctgc ccttccttct cccttaggg tagcccaaat cccattgcca       720
cacaacatct caacttacca tccctttcct ctatccccat cccctctgtc tgcgtcacag       780
aaagtctgtg tgttctgaag agttcagcct tcctctaacc aaacccacac tttctttacc       840
accgtgattc tcagagccag caagaaagaa atgttccaaa aggaaacctc catctcagcc       900
atttgcccgg agccgaaggt tgtgggctcc aggcctctca gtgaggtttg ttgcttgtgt       960
gtttcccgag gagcgggcag tcaggcagtg gtggttctct ctcccctctc tctgtcgcac      1020
gtggggtctc agctacattt acaagacttc accaccatgt tggagagctg ctccactttg      1080
ggggtcctcc caacatagta caggatggtc aggggctcca ggtcctgggg cacgcagcaa      1140
ggcgaggcag atgcttcagg gttcagagtg ttgtacagtc ccagcaccgt gctgtgggtt      1200
gtgtctgcac tgcggaggta tgggcaaggg cctgagcaga agttggcata gtagcccta       1260 ggttcatgga cccacttcca gcccagatcc tgtcggaagt caatgtagag ggggcgcaca      1320
cagcagttct cctccaagtt gcggaagcag taattggtgt ccaaagcccg cttcttcctc      1380
tgacccccct ggcccgggtt gtcgagccgg tgtgggggaa tcatcatgag gattagatga      1440
gggttgtggt gatccttctg cttcttgagg cgccccagat ctccacggcc atggtcatcc      1500
tcattgtcca cgccttttgaa tttgatttcc atcacctcgt gaatgttttc caggatatct      1560
ccattgggct gaaaggtgtg acatggacag tgaatgctga tttctagacc taagttggac      1620
tctcttctca acagccactc acgcacagtg tcagtgacat caaaggacag ccactcggca      1680
gtgccccgtg tgggcagatt cttgccaccg atatagcgct gtttggcaat gtgctcatct      1740
ggccgaagga tctggaagag ctcgatcctc tgctcattcc gcttagagct ggggttgggc      1800
acccgcaaga cccggaattc tgctcggaat aggttggttc tattttttctc cactgaggac      1860 acattgaagc ggaaaacctt ggaggtaatt cctttagggc agacagccag ttcgttgtgc      1920
```

| | |
|---|---|
| tccgccagcc cctggatcat gtcgaattta tggatttctt tggcatagta ttccgactcg | 1980 |
| gtgttttcct gggtgcagcc ttcctccctc tccccatgca tctcctccag cagctcccgg | 2040 |
| gtgctgttgt aaagggccag gacctgatag gggacgtggg tcatcaccgt tggctcaggg | 2100 |
| gggctggtga gcctgagctt gctcaagatc tgtcccctaa tggcttccac cctcttcttc | 2160 |
| ttgatgtggc cgaagtccaa ggtggtgcaa gtggacagag agaggctgac cgtggcaaag | 2220 |
| ttcagcaggg ccaggaccac cagagccctt gcaagtgca tcttcatgtg tgagctggga | 2280 |
| agagaggcca gggggacggc aaggcctgga gaggaagaga ccccagcaga cgtgcagaag | 2340 |
| gagggaggaa aaccaggcgg cctccccaga tcccaaagac tgaggcttgg caagaaggtg | 2400 |
| catgaactca ctgcactgcg agagcttcag gacttccagg aagcgctggc aaccctgagg | 2460 |
| acgaagaagc ggactgtgtg ccttgtagcg ctgggattct tgtccatgtg tctaaacagg | 2520 |
| ttttgctgg | 2529 |

<210> SEQ ID NO 150
<211> LENGTH: 1259
<212> TYPE: DNA
<213> ORGANISM: Artificial Sequence
<220> FEATURE:
<223> OTHER INFORMATION: Synthetically constructedantisense mRNA of human IL-10

<400> SEQUENCE: 150

| | |
|---|---|
| tcaccctatg gaaacagctt aaaaacaggt gaaataata aatattgaaa aaaattataa | 60 |
| tatttgggctt ctttctaaat cgttcacaga gaagctcagt aaataaatag aaatgggggt | 120 |
| tgaggtatca gaggtaataa atattctata agagaggtac aataaggttt ctcaaggggc | 180 |
| tgggtcagct atcccagagc cccagatccg attttggaga cctctaattt atgtcctaga | 240 |
| gtctatagag tcgccaccct gatgtctcag tttcgtatct tcattgtcat gtaggcttct | 300 |
| atgtagttga tgaagatgtc aaactcactc atggctttgt agatgccttt ctcttggagc | 360 |
| ttattaaagg cattcttcac ctgctccacg gccttgctct tgttttcaca gggaagaaat | 420 |
| cgatgacagc gccgtagcct cagcctgagg gtcttcaggt tctcccccag ggagttcaca | 480 |
| tgcgccttga tgtctgggtc ttggttctca gcttggggca tcacctcctc caggtaaaac | 540 |
| tggatcatct cagacaaggc ttggcaaccc aggtaaccct taaagtcctc cagcaaggac | 600 |
| tcctttaaca acaagttgtc cagctgatcc ttcatttgaa agaaagtctt cactctgctg | 660 |
| aaggcatctc ggagatctcg aagcatgtta ggcaggttgc ctgggaagtg ggtgcagctg | 720 |
| ttctcagact gggtgccctg gcctgggctg gccctcaccc cagtcaggag gaccaggcaa | 780 |
| cagagcagtg ctgagctgtg catgccttct tttgcaagtc tgtcttgtgg tttggttttg | 840 |
| caagagcaac cccctgatgt gtagaccttc acctctctgt ccccctttta tattgtaagc | 900 |
| tcagggaggc ctcttcattc attaaaaagc cacaatcaag gtttcccggc acaggatttt | 960 |
| ttctgcttag agctcctcct tctctaacct ctctaataaa cttagttttc aatttttgca | 1020 |
| tcgtaagcaa aaatgattgg ttgaacatga acttctgcat tacagctatt tttaggatgg | 1080 |
| gctacctctc ttagaataat ttttttagctt ctcaattaaa aaaagttgat ttcctgggga | 1140 |
| gaacagctgt tctgtccgca gaggccctca gctgtgggtt ctcattcgcg tgttcctagg | 1200 |
| tcacagtgac gtggacaaat tgcccattcc agaatacaat gggattgaga ataattgg | 1259 |

<210> SEQ ID NO 151
<211> LENGTH: 1765
<212> TYPE: DNA

<213> ORGANISM: Artificial Sequence
<220> FEATURE:
<223> OTHER INFORMATION: Synthetically constructedantisense mRNA
      of human Prostaglandin E2 Synthase

<400> SEQUENCE: 151

```
ccatgagatg cctgccatga caggcgccac aaacctttcc tttattgcaa acatgtccca      60
gtcccgggag gcttgggaag agtgggaacc aggggaaccc aggatggga ttccactgaa      120
aacaaaccgt cctgctgtcc tgtcgagggc ccccacccac aggatgtagc catgggacag    180
ccactgaggg tccaggaaga ggggcggcag agcaggagg cagggacagg gaggggtcgc      240
cccagggcag tggcagggct ggaactcgtc cctaacatcc ctgagcccca gcaggtgccc    300
tgtgttagaa gcgagagggc tggtgggggt gcgtggacaa ggggcagaat gatcctgccc    360
ccaaccagta tcgccaggcg ctggcccagt ggccccaggc cctggcagct ggcgtcttcc    420
gctgccttcc ctctgctctg cgcggggaca ttcagtgcgc tggggaggcc tcggtgatgg    480
ccctctccac ccgcaggtac cagggctgga tgtgcgtgtg ctgcatcagg tcatcgaatg    540
catccagccc ctccatcaca cgcagcacgc catacaccgc caaatcagcg agattcggct    600
tctggccccc catgaagggc cggtccttgc ccacagcagc cacccacttg tcagcagcct    660
catagaggtc ctcgcgcacg ttgtcctgga ggcggtgcct gctcttgagt cgcttgctga    720
tgaggtacat ggccgctgca cccatgtact tggccacggc accctccacg gctccgaact    780
tgccctcgcg gacaatgtag tcaaaggacg ccagagcctc ggtgggcgtg cggtacacat    840
tgggggagat caggtgcacc agccagtcgt ccgcccactg ccgccacttc atctcctccg    900
tcctggcctc cttcccacca tacacttgct gggcctcctt ctcgttgagc atgagccagt    960
acttattgcc gaactcggtc acctccttgc cctgctcgtt cacagccttc atggctgggt   1020
agtaggtgat gatctcttcc aggggctgcc ccgacaccag gtaggtcttg agggcgctga   1080
tgatgacaga ggagtcattt agttgttgcg agctttctcc ttcctgggcc accaggatgg   1140
gcacctttct gtaggaggag aacttgatct cagccctgcg cacagggttc acctccacca   1200
cctggtaggg cagggcatgg aagtcgagga aggctcggac cttgctgcag aagggacacg   1260
tcttgtactg gtacagggtc agctgcaggc ggctggacag ggagagctgc gcggctgagc   1320
gctctgcgtg gaggtcctgg gcgcgcaggt gccaccgcgc cgtgtggtac agccccaggg   1380
ctccccccag ggccagcgcc gcagctccca gcagccgcgg gctcccctta cgagctgcag   1440
ccacggggct cgggccgccc gccgcccccg cgaagccagc ccggctctgc gtgggtagca   1500
gcggctgggg gcggcctccc agcctccagg ccaaggcgca cccaccaggc cacagcgccc   1560
gcaccacccg cgcagccggg tccatgttcg ctccgccggc gccgcgggcg ggcgcgcgaa   1620
acgaagacgc cgaggcacgc gcggcgttta aagggccagg actctggcgc ccgcgggtt   1680
ggccggggtg agggcgacgc taagggaacc ctcagcgctc tcgggactgg gcgtgtgccc   1740
ggcgcccaag ttcgaaacgc ccgcc                                          1765
```

<210> SEQ ID NO 152
<211> LENGTH: 990
<212> TYPE: DNA
<213> ORGANISM: Artificial Sequence
<220> FEATURE:
<223> OTHER INFORMATION: Synthetically constructedantisense mRNA
      of human VEGF

<400> SEQUENCE: 152

```
cagtgtgctg gcggccgcgg tgtgtctaca ggaatcccag aaataaaact ctctaatctt      60
```

-continued

```
ccgggctcgg tgatttagca gcaagaaaaa taaaatggcg aatccaattc caagagggac    120
cgtgctgggt cacccgcccg ggaatgcttc cgccggagtc tcgccctccg gacccaaagt    180
gctctgcgca gagtctcctc ttccttcatt tcaggtttct ggattaagga ctgttctgtc    240
gatggtgatg gtgtggtggc ggcagcgtgg tttctgtatc gatcgttctg tatcagtctt    300
tcctggtgag agatctggtt cccgaaaccc tgagggaggc tccttcctcc tgcccggctc    360
accgcctcgg cttgtcacat ctgcaagtac gttcgtttaa ctcaagctgc ctcgccttgc    420
aacgcgagtc tgtgtttttg caggaacatt tacacgtctg cggatcttgt acaaacaaat    480
gctttctccg ctctgagcaa ggcccacagg gattttcttg tcttgctcta tctttctttg    540
gtctgcattc acatttgttg tgctgtagga agctcatctc tcctatgtgc tggccttggt    600
gaggtttgat ccgcataatc tgcatggtga tgttggactc ctcagtgggc acacactcca    660
ggccctcgtc attgcagcag cccccgcatc gcatcagggg cacacaggat ggcttgaaga    720
tgtactcgat ctcatcaggg tactcctgga agatgtccac cagggtctcg attggatggc    780
agtagctgcg ctgatagaca tccatgaact tcaccacttc gtgatgattc tgccctcctc    840
cttctgccat gggtgcagcc tgggaccact tggcatggtg gaggtagagc agcaaggcga    900
ggctccaatg cacccaagac agcagaaagt tcatggtttc ggaggcccga ccggggccgg    960
gccggctcgc gccgggccgc cagcacactg                                      990
```

```
<210> SEQ ID NO 153
<211> LENGTH: 390
<212> TYPE: PRT
<213> ORGANISM: Homo sapiens

<400> SEQUENCE: 153
```

```
Met Pro Pro Ser Gly Leu Arg Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
```

```
                    210                 215                 220
Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
                275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 154
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 154

Ala Leu Asp Thr Asn Tyr Cys Phe Ser Ser Thr Glu Lys Asn Cys Cys
1               5                   10                  15

Val Arg Gln Leu
            20

<210> SEQ ID NO 155
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 155

Tyr Ile Asp Phe Arg Lys Asp Leu Gly Trp Lys Trp Ile His Glu Pro
1               5                   10                  15

Lys Gly Tyr His
            20

<210> SEQ ID NO 156
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 156
```

```
Ala Asn Phe Cys Leu Gly Pro Cys Pro Tyr Ile Trp Ser Leu Asp Thr
1               5                   10                  15

Gln Tyr Ser Lys
            20

<210> SEQ ID NO 157
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 157

Val Leu Ala Leu Tyr Asn Gln His Asn Pro Gly Ala Ser Ala Ala Pro
1               5                   10                  15

Cys Cys Val Pro
            20

<210> SEQ ID NO 158
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 158

Gln Ala Leu Glu Pro Leu Pro Ile Val Tyr Tyr Val Gly Arg Lys Pro
1               5                   10                  15

Lys Val Glu Gln
            20

<210> SEQ ID NO 159
<211> LENGTH: 12
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 159

Leu Ser Asn Met Ile Val Arg Ser Cys Lys Cys Ser
1               5                   10

<210> SEQ ID NO 160
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 160

Thr Glu Lys Asn Cys Cys Val Arg Gln Leu Tyr Ile Asp Phe Arg Lys
1               5                   10                  15

Asp Leu Gly Trp
            20

<210> SEQ ID NO 161
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 1
```

```
<400> SEQUENCE: 161

Lys Trp Ile His Glu Pro Lys Gly Tyr His Ala Asn Phe Cys Leu Gly
  1               5                  10                  15

Pro Cys Pro Tyr
             20

<210> SEQ ID NO 162
<211> LENGTH: 19
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 162

Trp Ser Leu Asp Thr Gln Tyr Ser Lys Val Leu Ala Leu Tyr Asn Gln
  1               5                  10                  15

His Asn Pro

<210> SEQ ID NO 163
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 163

Gly Ala Ser Ala Ala Pro Cys Cys Val Pro Gln Ala Leu Glu Pro Leu
  1               5                  10                  15

Pro Ile Val Tyr
             20

<210> SEQ ID NO 164
<211> LENGTH: 22
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 164

Tyr Val Gly Arg Lys Pro Lys Val Glu Gln Leu Ser Asn Met Ile Val
  1               5                  10                  15

Arg Ser Cys Lys Cys Ser
             20

<210> SEQ ID NO 165
<211> LENGTH: 40
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 165

Gln Tyr Ser Lys Val Leu Ala Leu Tyr Asn Gln His Asn Pro Gly Ala
  1               5                  10                  15

Ser Ala Ala Pro Cys Cys Val Pro Gln Ala Leu Glu Pro Leu Pro Ile
             20                  25                  30

Val Tyr Tyr Val Gly Arg Lys Pro
             35                  40

<210> SEQ ID NO 166
```

```
<211> LENGTH: 40
<212> TYPE: PRT
<213> ORGANISM: Artificial Sequence
<220> FEATURE:
<223> OTHER INFORMATION: Synthetically constructed peptide
      fragments of human TGF-beta 1
<220> FEATURE:
<221> NAME/KEY: DISULFID
<222> LOCATION: (21)
<223> OTHER INFORMATION: intermolecular disulfide bridge with SEQ ID No.
      219

<400> SEQUENCE: 166

Gln Tyr Ser Lys Val Leu Ala Leu Tyr Asn Gln His Asn Pro Gly Ala
 1               5                  10                  15

Ser Ala Ala Pro Cys Cys Val Pro Gln Ala Leu Glu Pro Leu Pro Ile
                20                  25                  30

Val Tyr Tyr Val Gly Arg Lys Pro
                35                  40

<210> SEQ ID NO 167
<211> LENGTH: 112
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 167

Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
                100                 105                 110

<210> SEQ ID NO 168
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 168

Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp
                20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 1
```

```
<400> SEQUENCE: 169

Lys Trp Ile His Glu Pro Lys Gly Tyr His Ala Asn Phe Cys Leu Gly
  1               5                  10                  15

Pro Cys Pro Tyr Ile Trp Ser Leu Asp Thr Gln Tyr Ser Lys
             20                  25                  30

<210> SEQ ID NO 170
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 170

Val Leu Ala Leu Tyr Asn Gln His Asn Pro Gly Ala Ser Ala Ala Pro
  1               5                  10                  15

Cys Cys Val Pro Gln Ala Leu Glu Pro Leu Pro Ile Val Tyr
             20                  25                  30

<210> SEQ ID NO 171
<211> LENGTH: 22
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 171

Tyr Val Gly Arg Lys Pro Lys Val Glu Gln Leu Ser Asn Met Ile Val
  1               5                  10                  15

Arg Ser Cys Lys Cys Ser
             20

<210> SEQ ID NO 172
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 172

Cys Val Arg Gln Leu Tyr Ile Asp Phe Arg Lys Asp Leu Gly Trp Lys
  1               5                  10                  15

Trp Ile His Glu Pro Lys Gly Tyr His Ala Asn Phe Cys Leu
             20                  25                  30

<210> SEQ ID NO 173
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 173

Gly Pro Cys Pro Tyr Ile Trp Ser Leu Asp Thr Gln Tyr Ser Lys Val
  1               5                  10                  15

Leu Ala Leu Tyr Asn Gln His Asn Pro Gly Ala Ser Ala Ala
             20                  25                  30

<210> SEQ ID NO 174
<211> LENGTH: 30
```

```
<212> TYPE: PRT
<213> ORGANISM: Artificial Sequence
<220> FEATURE:
<223> OTHER INFORMATION: Synthetically constructed peptide
      fragments of human TGF-beta 1

<400> SEQUENCE: 174

Pro Cys Cys Val Pro Gln Ala Leu Glu Pro Leu Pro Ile Val Tyr Tyr
  1               5                  10                  15

Val Gly Arg Lys Pro Lys Val Glu Gln Leu Ser Asn Met Ile
             20                  25                  30

<210> SEQ ID NO 175
<211> LENGTH: 413
<212> TYPE: PRT
<213> ORGANISM: Homo sapiens

<400> SEQUENCE: 175

Met His Tyr Cys Val Leu Ser Ala Phe Leu Ile Leu His Leu Val Thr
  1               5                  10                  15

Val Ala Leu Ser Leu Ser Thr Cys Ser Thr Leu Asp Met Asp Gln Phe
             20                  25                  30

Met Arg Lys Arg Ile Glu Ala Ile Arg Gly Gln Ile Leu Ser Lys Leu
         35                  40                  45

Lys Leu Thr Ser Pro Pro Glu Asp Tyr Pro Gly Pro Glu Glu Val Pro
 50                  55                  60

Pro Glu Val Ile Ser Ile Tyr Asn Ser Thr Arg Asp Leu Leu Gln Glu
 65                  70                  75                  80

Lys Ala Ser Arg Arg Ala Ala Ala Cys Glu Arg Glu Arg Ser Asp Glu
                 85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
210                 215                 220

His Cys Pro Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
        275                 280                 285

Tyr Arg Leu Glu Ser Gln Gln Thr Asn Arg Arg Lys Arg Ala Leu Asp
    290                 295                 300

Ala Ala Tyr Cys Phe Arg Asn Val Gln Asp Asn Cys Cys Leu Arg Pro
```

```
                305                 310                 315                 320

Leu Tyr Ile Asp Phe Lys Arg Asp Leu Gly Trp Lys Trp Ile His Glu
                325                 330                 335

Pro Lys Gly Tyr Asn Ala Asn Phe Cys Ala Gly Ala Cys Pro Tyr Leu
                340                 345                 350

Trp Ser Ser Asp Thr Gln His Ser Arg Val Leu Ser Leu Tyr Asn Thr
            355                 360                 365

Ile Asn Pro Glu Ala Ser Ala Ser Pro Cys Cys Val Ser Gln Asp Leu
            370                 375                 380

Glu Pro Leu Thr Ile Leu Tyr Tyr Ile Gly Lys Thr Pro Lys Ile Glu
385                 390                 395                 400

Gln Leu Ser Asn Met Ile Val Lys Ser Cys Lys Cys Ser
                405                 410

<210> SEQ ID NO 176
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 176

Ala Leu Asp Ala Ala Tyr Cys Phe Arg Asn Val Gln Asp Asn Cys Cys
1               5                   10                  15

Leu Arg Pro Leu
            20

<210> SEQ ID NO 177
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 177

Tyr Ile Asp Phe Lys Arg Asp Leu Gly Trp Lys Trp Ile His Glu Pro
1               5                   10                  15

Lys Gly Tyr Asn
            20

<210> SEQ ID NO 178
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 178

Ala Asn Phe Cys Ala Gly Ala Cys Pro Tyr Leu Trp Ser Ser Asp Thr
1               5                   10                  15

Gln His Ser Arg
            20

<210> SEQ ID NO 179
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 2
```

-continued

```
<400> SEQUENCE: 179

Val Leu Ser Leu Tyr Asn Thr Ile Asn Pro Glu Ala Ser Ala Ser Pro
1               5                   10                  15

Cys Cys Val Ser
            20

<210> SEQ ID NO 180
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 180

Gln Asp Leu Glu Pro Leu Thr Ile Leu Tyr Tyr Ile Gly Lys Thr Pro
1               5                   10                  15

Lys Ile Glu Gln
            20

<210> SEQ ID NO 181
<211> LENGTH: 12
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 181

Leu Ser Asn Met Ile Val Lys Ser Cys Lys Cys Ser
1               5                   10

<210> SEQ ID NO 182
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 182

Val Gln Asp Asn Cys Cys Leu Arg Pro Leu Tyr Ile Asp Phe Lys Arg
1               5                   10                  15

Asp Leu Gly Trp
            20

<210> SEQ ID NO 183
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 183

Lys Trp Ile His Glu Pro Lys Gly Tyr Asn Ala Asn Phe Cys Ala Gly
1               5                   10                  15

Ala Cys Pro Tyr
            20

<210> SEQ ID NO 184
<211> LENGTH: 20
<212> TYPE: PRT
<213> ORGANISM: Artificial Sequence
<220> FEATURE:
<223> OTHER INFORMATION: Synthetically constructed peptide
``` fragments of human TGF-beta 2

<400> SEQUENCE: 184

Leu Trp Ser Ser Asp Thr Gln His Ser Arg Val Leu Ser Leu Tyr Asn
1               5                   10                  15

Thr Ile Asn Pro
            20

<210> SEQ ID NO 185
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 185

Glu Ala Ser Ala Ser Pro Cys Cys Val Ser Gln Asp Leu Glu Pro Leu
1               5                   10                  15

Thr Ile Leu Tyr
            20

<210> SEQ ID NO 186
<211> LENGTH: 22
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 186

Tyr Ile Gly Lys Thr Pro Lys Ile Glu Gln Leu Ser Asn Met Ile Val
1               5                   10                  15

Lys Ser Cys Lys Cys Ser
            20

<210> SEQ ID NO 187
<211> LENGTH: 41
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 187

Gln His Ser Arg Val Leu Ser Leu Tyr Asn Thr Ile Asn Pro Glu Ala
1               5                   10                  15

Ser Ala Ser Pro Cys Cys Val Ser Gln Asp Leu Glu Pro Leu Thr Ile
            20                  25                  30

Leu Tyr Tyr Ile Gly Lys Thr Pro Lys
        35                  40

<210> SEQ ID NO 188
<211> LENGTH: 41
<212> TYPE: PRT
<213> ORGANISM: Artificial Sequence
<220> FEATURE:
<223> OTHER INFORMATION: Synthetically constructed peptide
      fragments of human TGF-beta 2
<220> FEATURE:
<221> NAME/KEY: DISULFID
<222> LOCATION: (21)
<223> OTHER INFORMATION: intermolecular disulfide bridge with SEQ ID No.
      220

<400> SEQUENCE: 188

Gln His Ser Arg Val Leu Ser Leu Tyr Asn Thr Ile Asn Pro Glu Ala
1               5                   10                  15

Ser Ala Ser Pro Cys Cys Val Ser Gln Asp Leu Glu Pro Leu Thr Ile
            20                  25                  30

Leu Tyr Tyr Ile Gly Lys Thr Pro Lys
        35                  40

<210> SEQ ID NO 189
<211> LENGTH: 112
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 189

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 190
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 190

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 191

Lys Trp Ile His Glu Pro Lys Gly Tyr Asn Ala Asn Phe Cys Ala Gly
1               5                   10                  15

Ala Cys Pro Tyr Leu Trp Ser Ser Asp Thr Gln His Ser Arg
            20                  25                  30

<210> SEQ ID NO 192
<211> LENGTH: 30
<212> TYPE: PRT
<213> ORGANISM: Artificial Sequence

```
<220> FEATURE:
<223> OTHER INFORMATION: Synthetically constructed peptide
      fragments of human TGF-beta 2

<400> SEQUENCE: 192

Val Leu Ser Leu Tyr Asn Thr Ile Asn Pro Glu Ala Ser Ala Ser Pro
1               5                   10                  15

Cys Cys Val Ser Gln Asp Leu Glu Pro Leu Thr Ile Leu Tyr
            20                  25                  30

<210> SEQ ID NO 193
<211> LENGTH: 22
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 193

Tyr Ile Gly Lys Thr Pro Lys Ile Glu Gln Leu Ser Asn Met Ile Val
1               5                   10                  15

Lys Ser Cys Lys Cys Ser
            20

<210> SEQ ID NO 194
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 194

Cys Leu Arg Pro Leu Tyr Ile Asp Phe Lys Arg Asp Leu Gly Trp Lys
1               5                   10                  15

Trp Ile His Glu Pro Lys Gly Tyr Asn Ala Asn Phe Cys Ala
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 195

Gly Ala Cys Pro Tyr Leu Trp Ser Ser Asp Thr Gln His Ser Arg Val
1               5                   10                  15

Leu Ser Leu Tyr Asn Thr Ile Asn Pro Glu Ala Ser Ala Ser
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 2

<400> SEQUENCE: 196

Pro Cys Cys Val Ser Gln Asp Leu Glu Pro Leu Thr Ile Leu Tyr Tyr
1               5                   10                  15

Ile Gly Lys Thr Pro Lys Ile Glu Gln Leu Ser Asn Met Ile
            20                  25                  30
```

-continued

```
<210> SEQ ID NO 197
<211> LENGTH: 412
<212> TYPE: PRT
<213> ORGANISM: Homo sapiens

<400> SEQUENCE: 197

Met Lys Met His Leu Gln Arg Ala Leu Val Val Ala Leu Leu Asn
  1               5                  10                  15

Phe Ala Thr Val Ser Leu Ser Leu Ser Thr Cys Thr Thr Leu Asp Phe
                 20                  25                  30

Gly His Ile Lys Lys Lys Arg Val Glu Ala Ile Arg Gly Gln Ile Leu
             35                  40                  45

Ser Lys Leu Arg Leu Thr Ser Pro Pro Glu Pro Thr Val Met Thr His
 50                  55                  60

Val Pro Tyr Gln Val Leu Ala Leu Tyr Asn Ser Thr Arg Glu Leu Leu
 65                  70                  75                  80

Glu Glu Met His Gly Glu Arg Glu Gly Cys Thr Gln Glu Asn Thr
                 85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
            115                 120                 125

Ser Lys Val Phe Arg Phe Asn Val Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Ala
    290                 295                 300

Ala Tyr Cys Phe Arg Asn Val Gln Asp Asn Cys Cys Leu Arg Pro Leu
305                 310                 315                 320

Tyr Ile Asp Phe Lys Arg Asp Leu Gly Trp Lys Trp Ile His Glu Pro
                325                 330                 335

Lys Gly Tyr Asn Ala Asn Phe Cys Ala Gly Ala Cys Pro Tyr Leu Trp
            340                 345                 350

Ser Ser Asp Thr Gln His Ser Arg Val Leu Ser Leu Tyr Asn Thr Ile
        355                 360                 365

Asn Pro Glu Ala Ser Ala Ser Pro Cys Cys Val Ser Gln Asp Leu Glu
    370                 375                 380
```

```
Pro Leu Thr Ile Leu Tyr Tyr Ile Gly Lys Thr Pro Lys Ile Glu Gln
385                 390                 395                 400

Leu Ser Asn Met Ile Val Lys Ser Cys Lys Cys Ser
                405                 410

<210> SEQ ID NO 198
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 198

Ala Leu Asp Thr Asn Tyr Cys Phe Arg Asn Leu Glu Glu Asn Cys Cys
1               5                   10                  15

Val Arg Pro Leu
            20

<210> SEQ ID NO 199
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 199

Tyr Ile Asp Phe Arg Gln Asp Leu Gly Trp Lys Trp Val His Glu Pro
1               5                   10                  15

Lys Gly Tyr Tyr
            20

<210> SEQ ID NO 200
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 200

Ala Asn Phe Cys Ser Gly Pro Cys Pro Tyr Leu Arg Ser Ala Asp Thr
1               5                   10                  15

Thr His Ser Thr
            20

<210> SEQ ID NO 201
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 201

Val Leu Gly Leu Tyr Asn Thr Leu Asn Pro Glu Ala Ser Ala Ser Pro
1               5                   10                  15

Cys Cys Val Pro
            20

<210> SEQ ID NO 202
<211> LENGTH: 20
<212> TYPE: PRT
<213> ORGANISM: Artificial Sequence
<220> FEATURE:
```

```
<223> OTHER INFORMATION: Synthetically constructed peptide
      fragments of human TGF-beta 3

<400> SEQUENCE: 202

Gln Asp Leu Glu Pro Leu Thr Ile Leu Tyr Tyr Val Gly Arg Thr Pro
1               5                   10                  15

Lys Val Glu Gln
            20

<210> SEQ ID NO 203
<211> LENGTH: 12
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 203

Leu Ser Asn Met Val Val Lys Ser Cys Lys Cys Ser
1               5                   10

<210> SEQ ID NO 204
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 204

Asn Leu Glu Glu Asn Cys Cys Val Arg Pro Leu Tyr Ile Asp Phe Arg
1               5                   10                  15

Gln Asp Leu Gly
            20

<210> SEQ ID NO 205
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 205

Trp Lys Trp Val His Glu Pro Lys Gly Tyr Tyr Ala Asn Phe Cys Ser
1               5                   10                  15

Gly Pro Cys Pro
            20

<210> SEQ ID NO 206
<211> LENGTH: 20
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 206

Tyr Leu Arg Ser Ala Asp Thr Thr His Ser Thr Val Leu Gly Leu Tyr
1               5                   10                  15

Asn Thr Leu Asn
            20

<210> SEQ ID NO 207
<211> LENGTH: 20
<212> TYPE: PRT
```

```
<213> ORGANISM: Artificial Sequence
<220> FEATURE:
<223> OTHER INFORMATION: Synthetically constructed peptide
      fragments of human TGF-beta 3

<400> SEQUENCE: 207

Pro Glu Ala Ser Ala Ser Pro Cys Cys Val Pro Gln Asp Leu Glu Pro
  1               5                  10                  15

Leu Thr Ile Leu
            20

<210> SEQ ID NO 208
<211> LENGTH: 23
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 208

Tyr Tyr Val Gly Arg Thr Pro Lys Val Glu Gln Leu Ser Asn Met Val
  1               5                  10                  15

Val Lys Ser Cys Lys Cys Ser
            20

<210> SEQ ID NO 209
<211> LENGTH: 41
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 209

Thr His Ser Thr Val Leu Gly Leu Tyr Asn Thr Leu Asn Pro Glu Ala
  1               5                  10                  15

Ser Ala Ser Pro Cys Cys Val Pro Gln Asp Leu Glu Pro Leu Thr Ile
             20                  25                  30

Leu Tyr Tyr Val Gly Arg Thr Pro Lys
         35                  40

<210> SEQ ID NO 210
<211> LENGTH: 41
<212> TYPE: PRT
<213> ORGANISM: Artificial Sequence
<220> FEATURE:
<223> OTHER INFORMATION: Synthetically constructed peptide
      fragments of human TGF-beta 3
<220> FEATURE:
<221> NAME/KEY: DISULFID
<222> LOCATION: (21)
<223> OTHER INFORMATION: intermolecular disulfide bridge to SEQ ID No.
      221

<400> SEQUENCE: 210

Thr His Ser Thr Val Leu Gly Leu Tyr Asn Thr Leu Asn Pro Glu Ala
  1               5                  10                  15

Ser Ala Ser Pro Cys Cys Val Pro Gln Asp Leu Glu Pro Leu Thr Ile
             20                  25                  30

Leu Tyr Tyr Val Gly Arg Thr Pro Lys
         35                  40

<210> SEQ ID NO 211
<211> LENGTH: 112
<212> TYPE: PRT
<213> ORGANISM: Artificial Sequence
```

```
<220> FEATURE:
<223> OTHER INFORMATION: Synthetically constructed peptide
      fragments of human TGF-beta 3

<400> SEQUENCE: 211

Ala Leu Asp Ala Ala Tyr Cys Phe Arg Asn Val Gln Asp Asn Cys Cys
  1               5                  10                  15

Leu Arg Pro Leu Tyr Ile Asp Phe Lys Arg Asp Leu Gly Trp Lys Trp
             20                  25                  30

Ile His Glu Pro Lys Gly Tyr Asn Ala Asn Phe Cys Ala Gly Ala Cys
         35                  40                  45

Pro Tyr Leu Trp Ser Ser Asp Thr Gln His Ser Arg Val Leu Ser Leu
     50                  55                  60

Tyr Asn Thr Ile Asn Pro Glu Ala Ser Ala Ser Pro Cys Cys Val Ser
 65                  70                  75                  80

Gln Asp Leu Glu Pro Leu Thr Ile Leu Tyr Tyr Ile Gly Lys Thr Pro
             85                  90                  95

Lys Ile Glu Gln Leu Ser Asn Met Ile Val Lys Ser Cys Lys Cys Ser
            100                 105                 110

<210> SEQ ID NO 212
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 212

Ala Leu Asp Ala Ala Tyr Cys Phe Arg Asn Val Gln Asp Asn Cys Cys
  1               5                  10                  15

Leu Arg Pro Leu Tyr Ile Asp Phe Lys Arg Asp Leu Gly Trp
             20                  25                  30

<210> SEQ ID NO 213
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 213

Lys Trp Ile His Glu Pro Lys Gly Tyr Asn Ala Asn Phe Cys Ala Gly
  1               5                  10                  15

Ala Cys Pro Tyr Leu Trp Ser Ser Asp Thr Gln His Ser Arg
             20                  25                  30

<210> SEQ ID NO 214
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 214

Val Leu Ser Leu Tyr Asn Thr Ile Asn Pro Glu Ala Ser Ala Ser Pro
  1               5                  10                  15

Cys Cys Val Ser Gln Asp Leu Glu Pro Leu Thr Ile Leu Tyr
             20                  25                  30

<210> SEQ ID NO 215
```

-continued

```
<211> LENGTH: 22
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 215

Tyr Ile Gly Lys Thr Pro Lys Ile Glu Gln Leu Ser Asn Met Ile Val
 1               5                  10                  15

Lys Ser Cys Lys Cys Ser
            20

<210> SEQ ID NO 216
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 216

Cys Leu Arg Pro Leu Tyr Ile Asp Phe Lys Arg Asp Leu Gly Trp Lys
 1               5                  10                  15

Trp Ile His Glu Pro Lys Gly Tyr Asn Ala Asn Phe Cys Ala
            20                  25                  30

<210> SEQ ID NO 217
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 217

Gly Ala Cys Pro Tyr Leu Trp Ser Ser Asp Thr Gln His Ser Arg Val
 1               5                  10                  15

Leu Ser Leu Tyr Asn Thr Ile Asn Pro Glu Ala Ser Ala Ser
            20                  25                  30

<210> SEQ ID NO 218
<211> LENGTH: 30
<212> TYPE: PRT
<213> ORGANISM: Artificial Sequence
<220> FEATURE:
<223> OTHER INFORMATION: Synthetically constructed peptide
      fragments of human TGF-beta 3

<400> SEQUENCE: 218

Pro Cys Cys Val Ser Gln Asp Leu Glu Pro Leu Thr Ile Leu Tyr Tyr
 1               5                  10                  15

Ile Gly Lys Thr Pro Lys Ile Glu Gln Leu Ser Asn Met Ile
            20                  25                  30
```